(12) United States Patent
Serrano-Wu et al.

(10) Patent No.: US 10,329,257 B2
(45) Date of Patent: Jun. 25, 2019

(54) COMPOSITIONS AND METHODS FOR TREATING TUBERCULOSIS

(71) Applicant: The Broad Institute, Inc., Cambridge, MA (US)

(72) Inventors: Michael H. Serrano-Wu, Belmont, MA (US); Chao Fang, Cambridge, MA (US)

(73) Assignee: The Broad Institute, Inc., Cambridge, MA (US)

( * ) Notice: Subject to any disclaimer, the term of this patent is extended or adjusted under 35 U.S.C. 154(b) by 0 days.

(21) Appl. No.: 15/751,968

(22) PCT Filed: Aug. 12, 2016

(86) PCT No.: PCT/US2016/046676
§ 371 (c)(1),
(2) Date: Feb. 12, 2018

(87) PCT Pub. No.: WO2017/027768
PCT Pub. Date: Feb. 16, 2017

(65) Prior Publication Data
US 2018/0237394 A1 Aug. 23, 2018

Related U.S. Application Data

(60) Provisional application No. 62/220,579, filed on Sep. 18, 2015, provisional application No. 62/204,854, filed on Aug. 13, 2015.

(51) Int. Cl.
| | | |
|---|---|---|
| *C07D 215/04* | (2006.01) |
| *C07D 401/02* | (2006.01) |
| *C07D 401/04* | (2006.01) |
| *C07D 401/14* | (2006.01) |
| *C07D 405/02* | (2006.01) |
| *C07D 413/14* | (2006.01) |
| *C07D 215/12* | (2006.01) |
| *A61K 31/47* | (2006.01) |
| *C07D 215/48* | (2006.01) |
| *C07D 413/04* | (2006.01) |
| *C07D 215/14* | (2006.01) |
| *C07D 401/06* | (2006.01) |
| *C07D 407/04* | (2006.01) |
| *C07D 407/14* | (2006.01) |
| *C07D 409/04* | (2006.01) |
| *C07D 409/14* | (2006.01) |
| *A61P 31/06* | (2006.01) |
| *C07D 405/04* | (2006.01) |
| *C07D 405/14* | (2006.01) |

(52) U.S. Cl.
CPC ............ *C07D 215/12* (2013.01); *A61K 31/47* (2013.01); *A61P 31/06* (2018.01); *C07D 215/04* (2013.01); *C07D 215/14* (2013.01); *C07D 215/48* (2013.01); *C07D 401/02* (2013.01); *C07D 401/04* (2013.01); *C07D 401/06* (2013.01); *C07D 401/14* (2013.01); *C07D 405/02* (2013.01); *C07D 405/04* (2013.01); *C07D 405/14* (2013.01); *C07D 407/04* (2013.01); *C07D 407/14* (2013.01); *C07D 409/04* (2013.01); *C07D 409/14* (2013.01); *C07D 413/04* (2013.01)

(58) Field of Classification Search
CPC .. C07D 215/04; C07D 401/02; C07D 401/04; C07D 401/14; C07D 405/02; C07D 413/14
See application file for complete search history.

(56) References Cited

U.S. PATENT DOCUMENTS 8,138,347 B2 * 3/2012 Knight ................ C07D 285/24
544/105

FOREIGN PATENT DOCUMENTS

| IN | 2002DE00628 | 3/2005 |
| WO | WO-2008/142384 A1 | 11/2008 |
| WO | WO-2011/163610 A2 | 12/2011 |

OTHER PUBLICATIONS

International Search Report and Written Opinion for International Application No. PCT/US2016/046676 dated Nov. 16, 2016.

* cited by examiner

*Primary Examiner* — Laura L Stockton
(74) *Attorney, Agent, or Firm* — David P. Halstead; Foley Hoag LLP

(57) ABSTRACT

The present invention provides compounds for the treatment of a bacterial infection. Additionally, the present invention provides compositions and methods for using these compounds and compositions in the treatment of a bacterial infection in a subject.

20 Claims, No Drawings

COMPOSITIONS AND METHODS FOR TREATING TUBERCULOSIS

CROSS-REFERENCE TO RELATED APPLICATIONS

This application is a U.S. national phase of International Patent Application No. PCT/US2016/046676, filed Aug. 12, 2016, the contents of which are herein incorporated by reference in their entirety. International Patent Application No. PCT/US2016/046676 claims the benefit of priority of U.S. Patent Application Ser. Nos. 62/204,854, filed Aug. 13, 2015, and 62/220,579, filed Sep. 18, 2015.

BACKGROUND

Tuberculosis (TB) is a disease caused by the bacterium *Mycobacterium tuberculosis* (Mtb), and is spread from person to person through the air. It is estimated that one-third of world's population are latently infected by Mtb. Despite the availability of effective anti-TB drugs, such as isoniazide and rifampin, TB is still one of the world's deadliest diseases. According to World Health Organization, there were 9.4 million new TB cases and 1.7 million people died from TB in 2009. [Global tuberculosis control: WHO report 2010.WHO//HTM/TB/2010.7]. Development of new agents that reduce the duration and complexity of current therapies, as well as effectively kill emerging resistant mutants, multi-drug resistant TB and extensively drug resistant TB, would have a major impact on TB therapy and healthcare in countries where tuberculosis is prevalent.

SUMMARY

In one aspect, the invention provides compounds represented by general formula (I) or a pharmaceutically acceptable salt thereof:

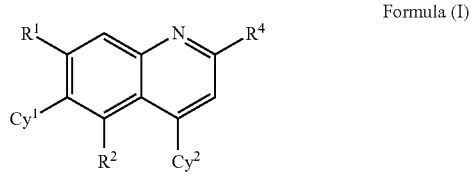

Formula (I)

wherein, independently for each occurrence,
$R^1$ is lower alkyl;
$R^2$ is lower alkyl;
$R^4$ is selected from hydrogen, acyl, alkyl, alkoxy, amino, alkylamino, dialkylamino, sulfonamide, —C(O)OR$^5$, —C(O)R$^7$, —C(O)NR$^5$R$^6$, —C(O)NHS(O$_2$)R$^7$, or —S(O$_2$)R$^7$, or a solubilizing group, preferably —C(O)NR$^5$R$^6$;
$R^5$ is hydrogen, alkyl, cycloalkyl, or heterocyclyl, preferably alkyl or cycloalkyl;
$R^6$ is hydrogen, hydroxyl, alkyl or cycloalkyl, preferably hydrogen; or
$R^5$ and $R^6$ together with the nitrogen to which they are attached form a heterocyclyl;
$R^7$ is alkyl, cycloalkyl, heterocyclyl, aryl or heteroaryl;
$Cy^1$ is selected from cycloalkyl (preferably cycloalkenyl), heterocyclyl (preferably heterocycloalkenyl), aryl (preferably phenyl), and heteroaryl; and
$Cy^2$ is selected from cycloalkyl (preferably cycloalkenyl), heterocyclyl (preferably heterocycloalkenyl), aryl (preferably phenyl), heteroaryl, and heterocyclyl.

DETAILED DESCRIPTION

In one aspect, the invention provides compounds represented by formula (I) or a pharmaceutically acceptable salt thereof:

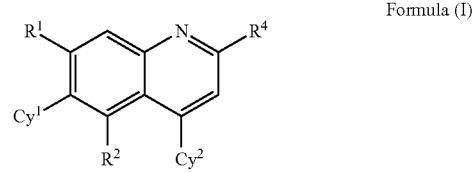

Formula (I)

wherein, independently for each occurrence,
$R^1$ is lower alkyl;
$R^2$ is lower alkyl;
$R^4$ is selected from hydrogen, acyl, alkyl, alkoxy, alkylamino, amino, dialkylamino, sulfonamido, —C(O)OR$^5$, —C(O)R$^7$, —C(O)NR$^5$R$^6$, —C(O)NHS(O$_2$)R$^7$, —S(O$_2$)R$^7$, and a solubilizing group, preferably —C(O)NR$^5$R$^6$;
$R^5$ is hydrogen, alkyl, cycloalkyl, or heterocyclyl, preferably alkyl or cycloalkyl;
$R^6$ is hydrogen, hydroxyl, alkyl or cycloalkyl, preferably hydrogen; or
$R^5$ and $R^6$ together with the nitrogen to which they are attached form a heterocyclyl;
$R^7$ is alkyl, cycloalkyl, heterocyclyl, aryl or heteroaryl;
$Cy^1$ is selected from cycloalkyl (preferably cycloalkenyl), heterocyclyl (preferably heterocycloalkenyl), aryl (preferably phenyl), and heteroaryl; and
$Cy^2$ is selected from cycloalkyl (preferably cycloalkenyl), heterocyclyl (preferably heterocycloalkenyl), aryl (preferably phenyl), heteroaryl, and heterocyclyl.

In certain embodiments, $Cy^1$ is selected from:

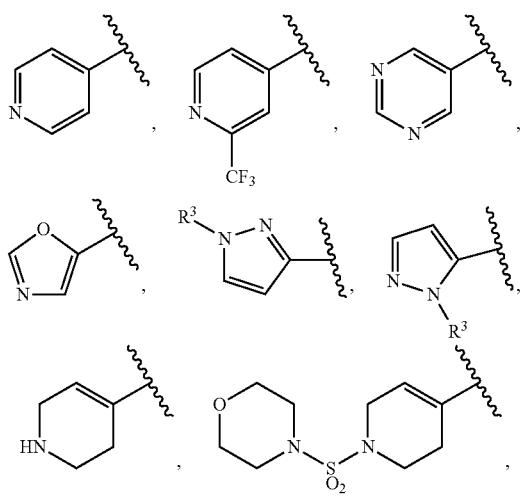

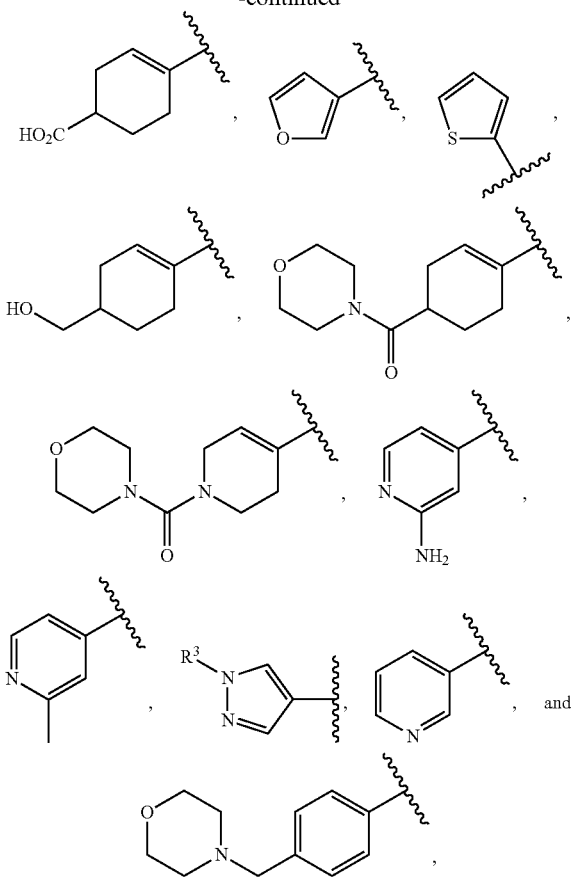

wherein R³ is H or methyl.

In certain embodiments, Cy¹ is selected from:

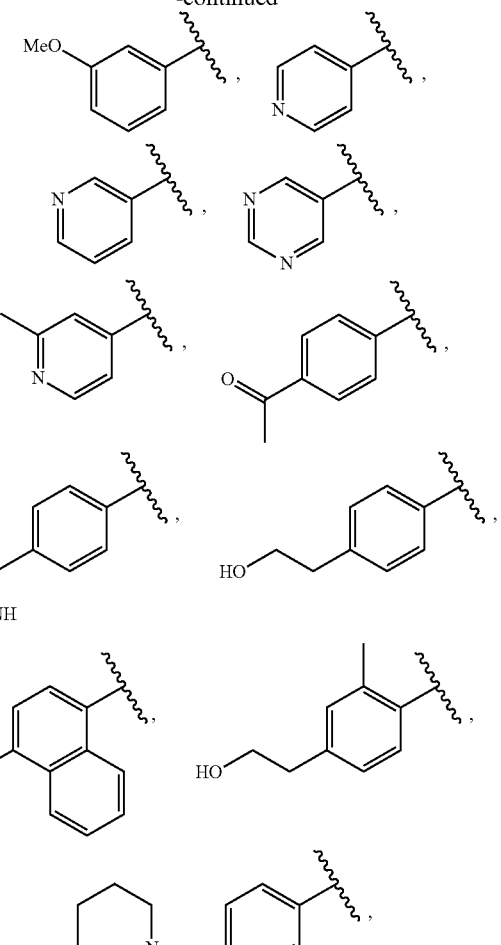

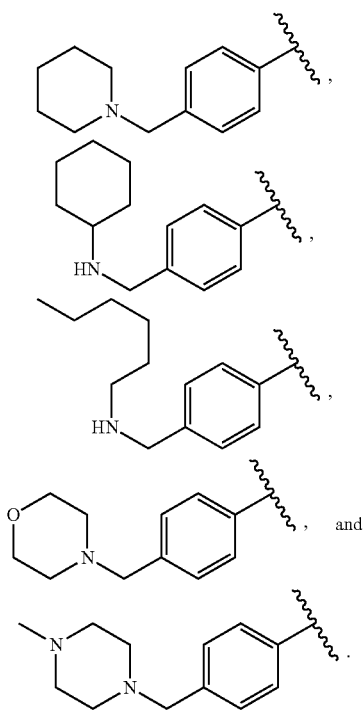

In certain embodiments, Cy¹ is selected from substituted or unsubstituted phenyl (e.g., alkylphenyl, (hydroxyalkyl)-phenyl, halophenyl, haloalkylphenyl, alkoxyphenyl, acyl-phenyl, (carbamoyl)-phenyl, (heterocyclylalkyl)-phenyl, (cycloalkylaminoalkyl)-phenyl, (aminoalkyl)-phenyl, heterocyclylphenyl, or (heterocyclylalkyl)-phenyl), furyl, thienyl, pyridinyl (e.g., aminopyridinyl, haloalkylpyridinyl, or alkylpyridinyl), pyrimidinyl, naphthyl (e.g., alkylnaphthyl), oxazolyl, pyrazolyl (e.g., alkylpyrazolyl), piperidinyl, heterocycloalkenyl (e.g., tetrahydropyridinyl, such as (heterocyclylsulfonyl)-tetrahydropyridinyl or (heterocyclylcarbonyl)-tetrahydropyridinyl, preferably attached via an alkenyl carbon of the heterocycloalkene), cycloalkenyl (e.g., cyclohexyl, such as carboxycyclohexenyl, (hydroxyalkyl)-cyclohexenyl, (heterocyclylalkyl)-cyclohexenyl, or (heterocyclylcarbonyl)-cyclohexenyl, preferably attached via an alkenyl carbon of the cycloalkene), and imidazolyl (e.g., methylimidazolyl).

In certain preferred embodiments, $Cy^1$ is a nitrogen-containing heteroaryl or heterocyclyl ring (e.g., substituted or unsubstituted). In certain such embodiments, $Cy^1$ is a six-membered ring having a nitrogen atom at the 4-position relative to the attachment to the quinoline core, e.g., a 4-pyridyl group. In embodiments wherein $Cy^1$ is a nitrogen-containing heterocyclyl ring, the ring is preferably unsaturated at the carbon attached to the quinoline core.

In other preferred embodiments, $Cy^1$ is a phenyl ring substituted at the 4-position relative to the attachment to the quinoline core, which substituent preferably contains a nitrogen atom, most preferably a basic nitrogen-containing group, e.g., a nitrogen-containing heteroalkyl or an amine-substituted alkyl, or the substituent comprises a substituted or unsubstituted nitrogen-containing heterocyclyl (e.g., morpholino) or heteroaryl ring and/or a ring substituted with an amine substituent. In certain such embodiments, the $pK_a$ of the conjugate acid of the basic nitrogen-containing group is about 6 or higher, or even about 8 or higher.

In certain embodiments, $Cy^2$ is selected from:

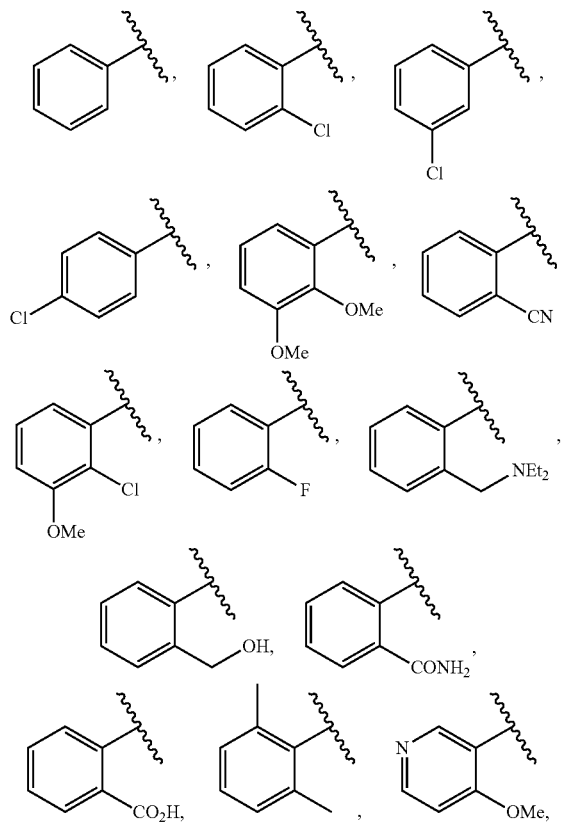

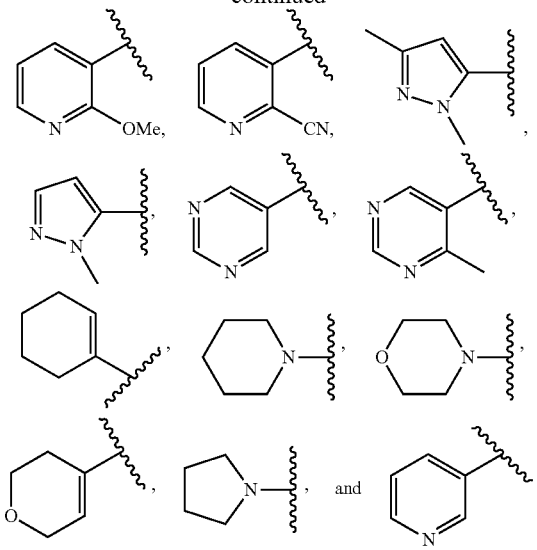

In certain embodiments, $Cy^2$ is selected from substituted or unsubstituted phenyl (e.g., halophenyl, alkoxyphenyl, dialkoxyphenyl, alkoxy, halophenyl, cyanophenyl, aminoalkylphenyl, (hydroxyalkyl)-phenyl, carboxamidophenyl, carboxyphenyl, or dialkylphenyl), pyridinyl (e.g., alkoxypyridinyl or cyanopyridinyl), pyrazolyl (e.g., alkylpyrazolyl or dialkylpyrazolyl), pyrimidinyl (e.g., methylpyrimidinyl), cycloalkenyl (e.g., cyclohexenyl), piperidinyl, morpholino, heterocycloalkenyl (e.g., dihydropyranyl), and pyrrolidinyl.

In certain preferred embodiments, $Cy^2$ is an ortho-substituted phenyl ring, e.g., substituted at an ortho-position with a halogen, alkyl, hydroxyl, alkoxy, etc.

In certain preferred embodiments, $R^4$ is a secondary amide group (e.g., —C(C=O)—NHR, where R is a non-hydrogen substituent). In certain such embodiments, the secondary amide is substituted with an alkyl, cycloalkyl, or heterocyclyl substituent, e.g., optionally substituted with one or more hydroxyl or amino substituents.

In certain embodiments, $R^4$ is selected from:

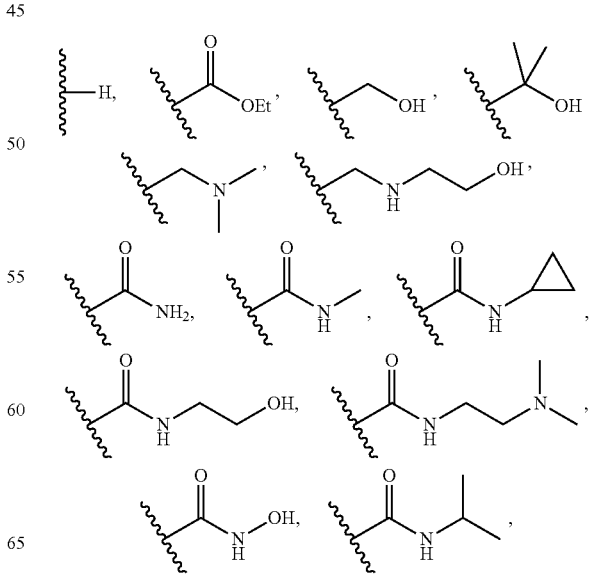

In some embodiments, $Cy^1$ is

[morpholinomethylphenyl] or [pyridin-4-yl].

In some embodiments, $Cy^2$ is

[phenyl], [2-chlorophenyl], or [2-fluorophenyl].

In some embodiments, $R^4$ is

—H or —C(O)NH—.

In certain other embodiments, $R^4$ is not H.

In some embodiments, $R^4$ is a solubilizing group.

In certain embodiments, the solubilizing group increases the water-solubility of the corresponding compound lacking the solubilizing group at least about 5-fold, preferably at least about 10-fold, more preferably at least about 20-fold and most preferably at least about 50-fold.

In certain embodiments, the solubilizing group is a moiety of the formula: $-(CH_2)_n-R^{100}-N(R^{101})(R^{101})$, wherein: n is selected from 0, 1 and 2; $R^{100}$ is selected from a bond, —C(O)—, and —O(CH_2)_n$; and each $R^{101}$ is independently selected from:

a. hydrogen;
b. $C_1$-$C_4$ straight or branched alkyl, wherein said alkyl is optionally substituted with halo, CN, OH, O—($C_1$-$C_4$ straight or branched alkyl), $N(R_1')(R_1')$, or =O;
c.

[ring with $Z_{24}$, $Z_{25}$, $Z_{26}$, $Z_{27}$, $Z_{28}$];

d.

[ring with $Z_{20}$, $Z_{21}$, $Z_{22}$, $Z_{23}$];

e.

[diazepane ring with $R_1'$];

f. both $R^{101}$ moieties are taken together with the nitrogen atom to which they are bound to form a ring of the structure

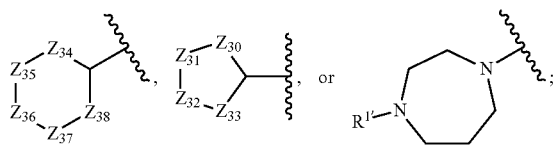

and
g. both $R^{101}$ moieties are taken together with the nitrogen atom to which they are bound to form a 5-membered heteroaryl ring containing 1 to 3 additional N atoms, wherein said heteroaryl ring is optionally substituted with $R_1$'; wherein:

each Z is independently selected from —O—, —S—, —$NR_1$'— and —$C(R^{50})(R^{50})$—, wherein: at least three of $Z_{20}$, $Z_{21}$, $Z_{22}$, and $Z_{23}$ are —$C(R^{50})(R^{50})$—; at least three of $Z_{24}$, $Z_{25}$, $Z_{26}$, $Z_{27}$, and $Z_{28}$ are —$C(R^{50})(R^{50})$—; at least four of $Z_{30}$, $Z_{31}$, $Z_{32}$, and $Z_{33}$ are —$C(R^{50})(R^{50})$—; and at least four of $Z_{34}$, $Z_{35}$, $Z_{36}$, $Z_{37}$, and $Z_{38}$ are —$C(R^{50})(R^{50})$—;

each $R_1$' is independently selected from hydrogen and a $C_1$-$C_3$ straight or branched alkyl optionally substituted with one or more substituent independently selected from halo, —CN, —OH, —$OCH_3$, —$NH_2$, —$NH(CH_3)$, —$N(CH_3)_2$, and =O;

each $R^{50}$ is independently selected from $R_1$', halo, CN, OH, O—($C_1$-$C_4$ straight or branched alkyl), $N(R_1')(R_1')$, =$CR_1$', $SR_1$', =$NR_1$', =$NOR_1$', and =O;

any two suitable non-cyclic $R^{50}$ are optionally bound to one another directly or via a $C_1$ to $C_2$ alkylene, alkenylene or alkanediylidene bridge to produce a bicyclic fused or spiro ring; and any

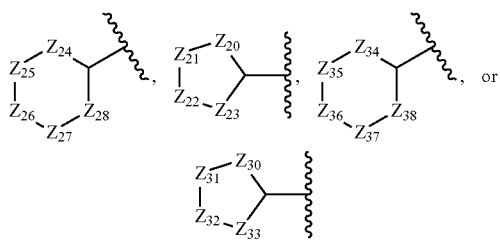

ring structure is optionally benzofused or fused to a monocyclic heteroaryl to produce a bicyclic ring.

For clarity, the term "$C_1$ to $C_2$ alkylene, alkenylene or alkanediylidene bridge" means the multivalent structures —$CH_2$—, —$CH_2$—$CH_2$—, —CH=, =CH—, —CH=CH—, or =CH—CH=. The two $R^{50}$ moieties that are optionally bound to one another can be either on the same carbon atom or different carbon atoms. The former produces a spiro bicyclic ring, while the latter produces a fused bicyclic ring. It will be obvious to those of skill in the art that when two $R^{50}$ are bound to one another to form a ring (whether directly or through one of the recited bridges), one or more terminal hydrogen atoms on each $R^{50}$ will be lost. Accordingly, a "suitable non-cyclic $R^{50}$" moiety available for forming a ring is a non-cyclic $R^{50}$ that comprises at least one terminal hydrogen atom.

In certain embodiments, the solubilizing group is a moiety of the formula: —$(CH_2)_n$—O—$R^{101}$, wherein n and $R^{101}$ are as defined above.

In certain embodiments, the solubilizing group is a moiety of the formula: —$(CH_2)_n$—C(O)—$R_1$', wherein n and $R_1$' are as defined above.

In certain embodiments, a solubilizing group is selected from —$(CH_2)_n$—$R^{102}$, wherein n is 0, 1 or 2, preferably 2; and $R^{102}$ is selected from

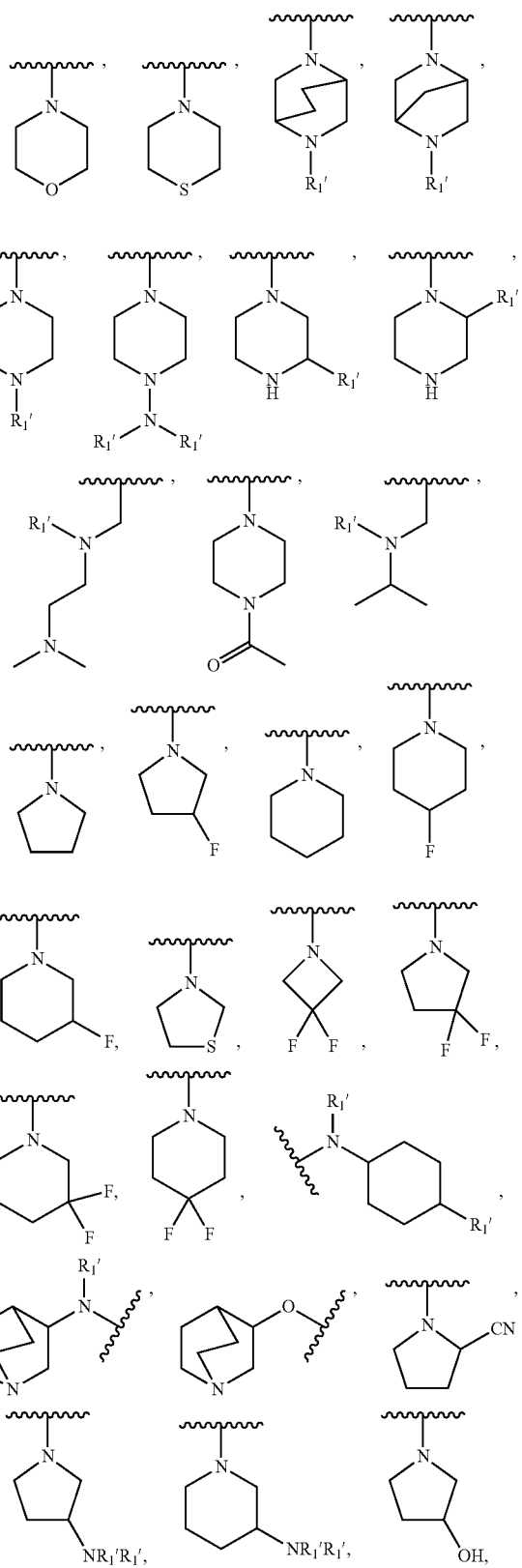

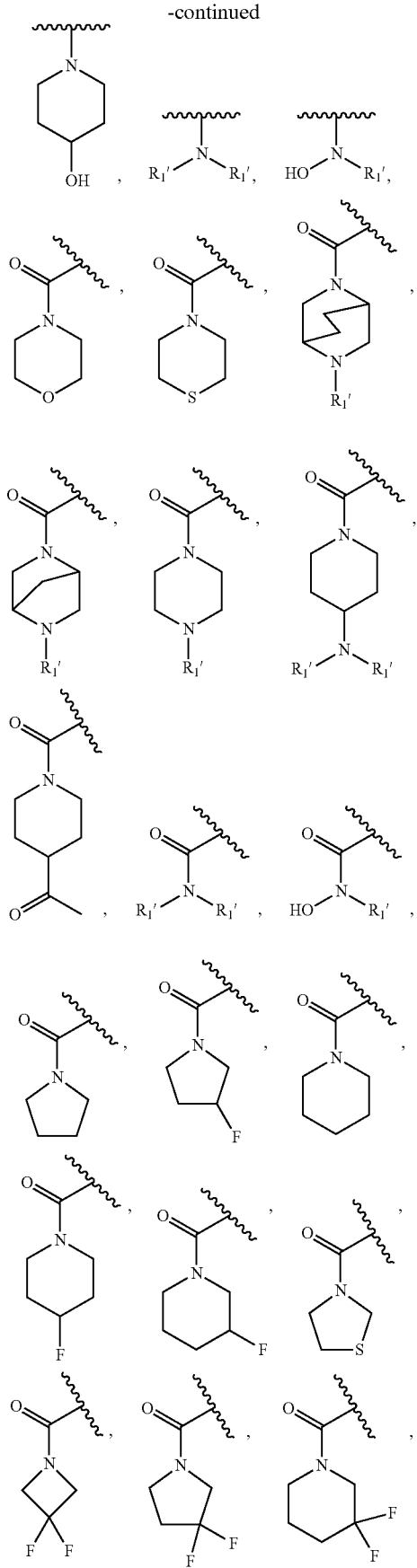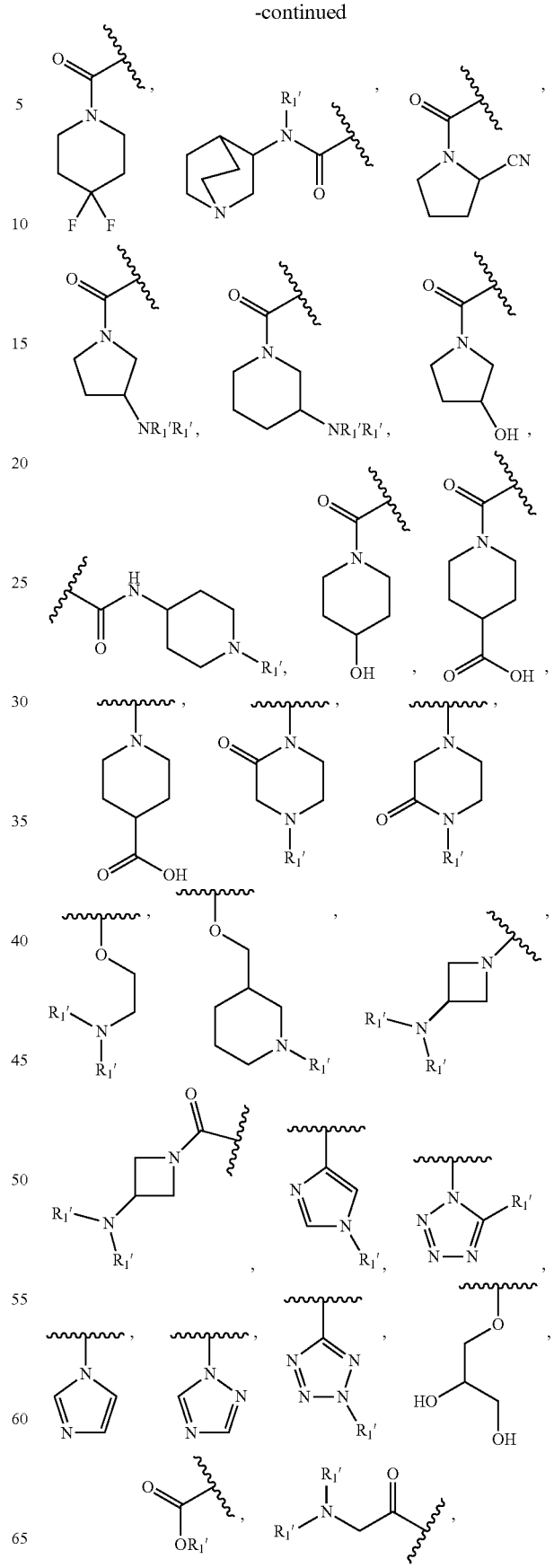

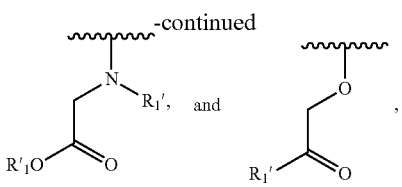

wherein $R_1'$ groups are as defined above.

In certain embodiments, a solubilizing group is selected from 2-dimethylaminoethylcarbamoyl, piperazin-1-ylcarbonyl, piperazinylmethyl, dimethylaminomethyl, 4-methylpiperazin-1-ylmethyl, 4-aminopiperidin-1-yl-methyl, 4-fluoropiperidin-1-yl-methyl, morpholinomethyl, pyrrolidin-1-ylmethyl, 2-oxo-4-benzylpiperazin-1-ylmethyl, 4-benzylpiperazin-1-ylmethyl, 3-oxopiperazin-1-ylmethyl, piperidin-1-ylmethyl, piperazin-1-ylethyl, 2,3-dioxopropylaminomethyl, thiazolidin-3-ylmethyl, 4-acetylpiperazin-1-ylmethyl, 4-acetylpiperazin-1-yl, morpholino, 3,3-difluoro-azetidin-1-ylmethyl, 2H-tetrazol-5-ylmethyl, thiomorpholin-4-ylmethyl, 1-oxothiomorpholin-4-ylmethyl, 1,1-dioxothiomorpholin-4-ylmethyl, 1H-imidazol-1-ylmethyl, 3,5-dimethylpiperazin-1ylmethyl, 4-hydroxypiperidin-1-ylmethyl, N-methyl(1-acetylpiperidin-4-yl)-aminomethyl, N-methylquinuclidin-3-ylaminomethyl, 1H-1,2,4-triazol-1-ylmethyl, 1-methylpiperidin-3-yl-oxymethyl, and 4-fluoropiperidin-1-yl.

To the extent not included within any of the definitions set forth above, the term "solubilizing group" also includes moieties disclosed as being attached to the 7-position of 1-cyclopropyl-6-fluoro-1,4-dihydro-4-oxoquinoline-3-carboxylic acid (ciprofloxacin) and its derivatives, as disclosed in PCT publications WO 2005/026165, WO 2005/049602, and WO 2005/033108, and European Patent publications EP 0343524, EP 0688772, EP 0153163, EP 0159174; as well as "water-solubilizing groups" described in United States patent publication 2006/0035891. The disclosure of each of these patent publications is incorporated herein by reference.

In some embodiments, $R^1$ and $R^2$ are methyl.

In one aspect, the invention provides a pharmaceutical composition comprising a compound as disclosed herein.

In certain embodiments, the pharmaceutical composition further comprises one or more pharmaceutically acceptable excipients.

In one aspect, the invention provides a compound or composition, as disclosed herein, for treating a bacterial infection.

In one aspect, the invention provides a method of treating a bacterial infection, such as a mycobacterial infection, in a subject, comprising administering to the subject a compound or composition as disclosed herein. In some embodiments, the subject is a mammal.

The compounds disclosed herein can be used treating a *mycobacterium* infection, in particular infection caused by resistant strains of *mycobacterium tuberculosis*. Compounds of Formula I are useful for the treatment of mycobacterial diseases, particularly those caused by pathogenic mycobacteria.

In some embodiments, the mycobacterial infection is caused by *Mycobacterium abscessus, Mycobacterium avium* complex, *Mycobacterium goodii, Mycobacterium leprae, Mycobacterium lepraemurium, Mycobacterium lepromatosis, Mycobacterium mucogenicum, Mycobacterium neoaurum, Mycobacterium triplex*, or *Mycobacterium tuberculosis* complex.

The invention further relates to conjoint therapy using compounds of Formula I with other antibacterial agents, in particular anti-mycobacterial agents. The compounds of Formula I can be combined with antibacterial agents such as rifampicin, rifampin, isoniazid, pyrazinamide, amikacin, ethionamide, moxifloxacin, ethambutol, streptomycin, para-aminosalicylic acid, cycloserine, capreomycin, kanamycin, thiacetazone, PA-824, quinolones/fluoroquinolones such as for example ofloxacin, ciprofloxacin, sparfloxacin; macrolides such as for example clarithromycin, clofazimine, amoxycillin with clavulanic acid, rifamycins, rifabutin, rifapentine.

The invention further relates to the use of a compound of Formula I in the manufacture of a medicament. In some embodiments, the compound or composition, as disclosed herein, is administered orally, nasally, buccally, sublingually, intramuscularly, intravenously, transmucosally, rectally, topically, transdermally, subcutaneously, or by inhalation.

Compounds

Compounds of the invention include compounds of Formula I as disclosed above and their salts (including pharmaceutically acceptable salts). Such compounds are suitable for the compositions and methods disclosed herein.

Definitions

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl"

group. An alkyl group with two open valences is sometimes referred to as an alkylene group, such as methylene, ethylene, propylene and the like.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF$_3$, —CN and the like. Exemplary substituted alkyls are described below. Cycloalkyls can be further substituted with alkyls, alkenyls, alkoxys, alkylthios, aminoalkyls, carbonyl-substituted alkyls, —CF$_3$, —CN, and the like.

The term "C$_{x-y}$" when used in conjunction with a chemical moiety, such as, acyl, acyloxy, alkyl, alkenyl, alkynyl, or alkoxy is meant to include groups that contain from x to y carbons in the chain. For example, the term "C$_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-tirfluoroethyl, etc. C$_0$ alkyl indicates a hydrogen where the group is in a terminal position, a bond if internal. The terms "C$_{2-y}$alkenyl" and "C$_{2-y}$alkynyl" refer to substituted or unsubstituted unsaturated aliphatic groups analogous in length and possible substitution to the alkyls described above, but that contain at least one double or triple bond respectively. As applied to heteroalkyls, "C$_{x-y}$" indicates that the group contains from x to y carbons and heteroatoms in the chain. As applied to carbocyclic structures, such as aryl and cycloalkyl groups, "C$_{x-y}$" indicates that the ring comprises x to y carbon atoms. As applied to heterocyclic structures, such as heteroaryl and heterocyclyl groups, "C$_{x-y}$" indicates that the ring contains from x to y carbons and heteroatoms. As applied to groups, such as aralkyl and heterocyclylalkyl groups, that have both ring and chain components, "C$_{x-y}$" indicates that the ring and the chain together contain from x to y carbon atoms and, as appropriate heteroatoms.

The term "alkylamino", as used herein, refers to an amino group substituted with at least one alkyl group and may be represented by the general formula alkylNR$^{10}$—, wherein each R$^{10}$ independently represent a hydrogen or hydrocarbyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

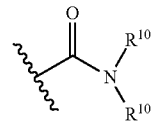

wherein each R$^{10}$ independently represent a hydrogen or hydrocarbyl group, or two R$^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

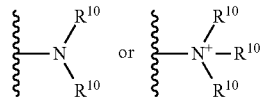

wherein each R$^{10}$ independently represents a hydrogen or a hydrocarbyl group, or two R$^{10}$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

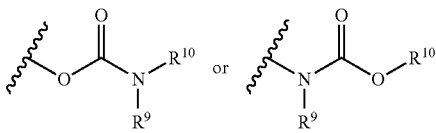

wherein R$^9$ and R$^{10}$ independently represent hydrogen or a hydrocarbyl group, such as an alkyl group, or R$^9$ and R$^{10}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0] octane, 4,5,6,7-tetrahydro-1H-indene and bicyclo[4.1.0] hept-3-ene. "Carbocycles" may be substituted at any one or more positions capable of bearing a hydrogen atom.

A "cycloalkyl" group is a substituted or unsubstituted cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group —OCO$_2$—R$^{10}$, wherein R$^{10}$ represents a hydrocarbyl group.

The term "carboxy", as used herein, refers to a group represented by the formula —CO$_2$H.

The term "ester", as used herein, refers to a group —C(O)OR$^{10}$ wherein R$^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent. In analogy with alkyl groups, heteroalkyl groups with two open valences are sometimes referred to as heteroalkylene groups. Preferably, the heteroatoms in heteroalkyl groups are selected from O and N.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to, aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl sub stituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7. When a polycyclic substituent is attached through an aryl or heteroaryl ring, that substituent may be referred to herein as an aryl or heteroaryl group, while if the polycyclic substituent is attached through a cycloalkyl or heterocyclyl group, that substituent may be referred to herein as a cycloalkyl or heterocyclyl group. By way of example, a 1,2,3,4-tetrahydronaphthalen-1-yl group would be a cycloalkyl group, while a 1,2,3,4-tetrahydronaphthalen-5-yl group would be an aryl group.

The term "silyl" refers to a silicon moiety with three hydrocarbyl moieties attached thereto.

The term "substituted" refers to moieties having substituents replacing a hydrogen on one or more carbons or heteroatoms of the moiety. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds.

In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

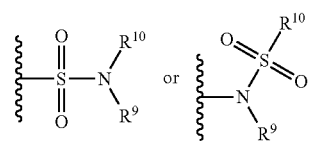

wherein $R^9$ and $R^{10}$ independently represents hydrogen or hydrocarbyl, such as alkyl, or $R^9$ and $R^{10}$ taken together with the intervening atom(s) complete a heterocycle having from 4 to 8 atoms in the ring structure.

The term "sulfoxide" is art-recognized and refers to the group —S(O)—$R^{10}$, wherein $R^{10}$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—$R^{10}$, wherein $R^{10}$ represents a hydrocarbyl.

The term "thioalkyl", as used herein, refers to an alkyl group substituted with a thiol group.

The term "thioester", as used herein, refers to a group —C(O)S$R^{10}$ or —SC(O)$R^{10}$ wherein $R^{10}$ represents a hydrocarbyl.

The term "thioether", as used herein, is equivalent to an ether, wherein the oxygen is replaced with a sulfur.

The term "urea" is art-recognized and may be represented by the general formula

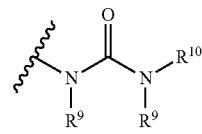

wherein $R^9$ and $R^{10}$ independently represent hydrogen or a hydrocarbyl, such as alkyl, or either occurrence of $R^9$ taken together with $R^{10}$ and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxylprotecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "prodrug" is intended to encompass compounds which, under physiologic conditions, are converted into the therapeutically active agents of the present invention (e.g., a compound of formula I). A common method for making a prodrug is to include one or more selected moieties which are hydrolyzed under physiologic conditions to reveal the desired molecule. In other embodiments, the prodrug is converted by an enzymatic activity of the host animal. For example, esters or carbonates (e.g., esters or carbonates of alcohols or carboxylic acids) are preferred prodrugs of the present invention. In certain embodiments, some or all of the compounds of formula I in a formulation represented above can be replaced with the corresponding suitable prodrug, e.g., wherein a hydroxyl in the parent compound is presented as an ester or a carbonate or carboxylic acid present in the parent compound is presented as an ester.

Pharmaceutical Compositions

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation of pharmaceutical composition can be a selfemulsifying drug delivery system or a selfmicroemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in microencapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatible with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals.

A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

In certain embodiments, compounds of the invention may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, an individual who receives such treatment can benefit from a combined effect of different therapeutic compounds.

This invention includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

The invention now being generally described, it will be more readily understood by reference to the following examples which are included merely for purposes of illustration of certain aspects and embodiments of the present invention, and are not intended to limit the invention.

EXEMPLIFICATION

Synthetic Protocols
Chemistry Material and Methods.

Unless otherwise noted, all reagents and solvents were purchased from commercial sources and used without further purification. The NMR spectra were obtained using a Bruker 300 or 400 MHz spectrometer. All $^1$H NMR spectra are reported in δ units (ppm) and were referenced to the peak for NMR solvents (CDCl$_3$, MeOD, d6-DMSO). Coupling constants (J) are reported in hertz. Column chromatography was performed utilizing 60 Å mesh silica gel on a Teledyne ISCO Combiflash Rf. All test compounds reported here had a purity ≥90% as determined by tandem liquid chromatography/Mass Spectrometry (LCMS) with UV absorption monitored at λ=210 nm. LCMS was performed on a Waters 2795 separations module and 3100 mass detector, with a Poroshell 120 EC-C18 column. Mobile phase A consisted of 0.01% formic acid in water and mobile phase B consisted of 0.01% formic acid in acetonitrile. The gradient ran from 5% to 95% mobile phase B over 7.5 min at 1.75 mL/min.

Example 1

Preparation of Compounds 2 and 13

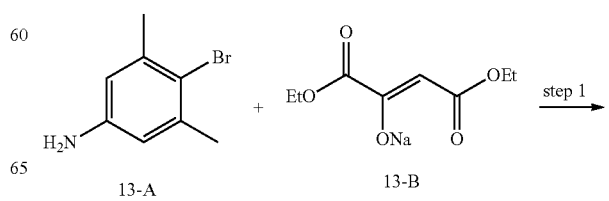

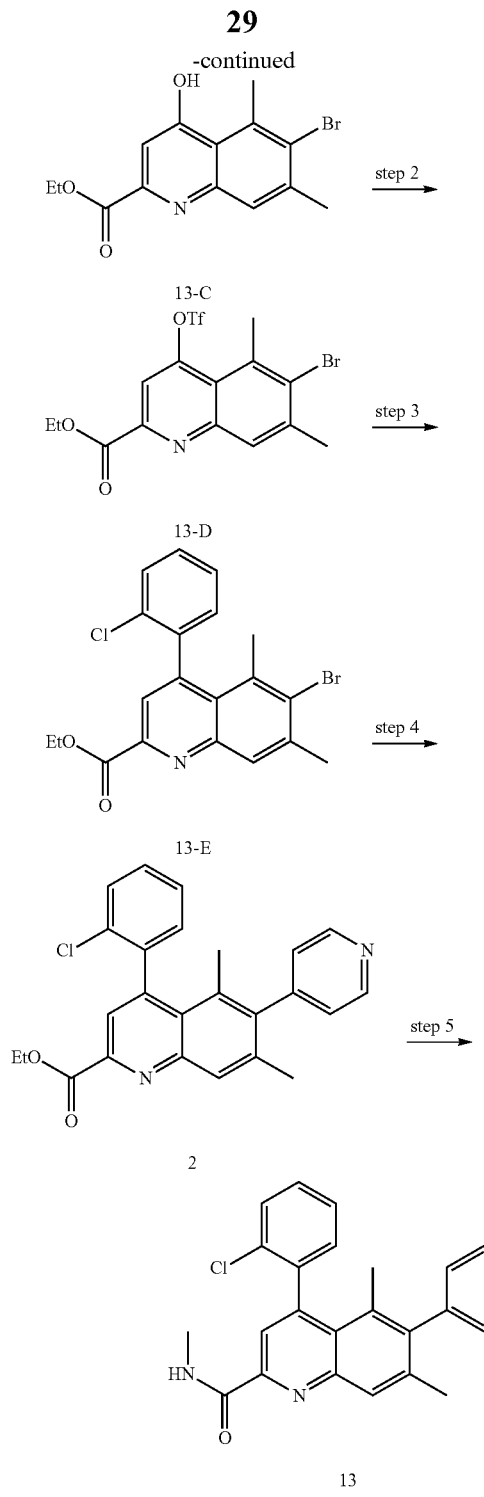

NMR (400 MHz, DMSO-$d_6$) δ 11.80 (s, 1H), 7.78 (s, 1H), 6.57 (s, 1H), 4.41 (q, J=7.1 Hz, 2H), 2.98 (s, 3H), 2.45 (s, 3H), 1.36 (t, J=7.1 Hz, 3H). LCMS (M+H)$^+$: 324.15, 326.15.

Step 2: To a solution of 13-C (1.8 g, 5.55 mmol) in DCM (19 mL) was slowly added Et$_3$N (2.4 mL, 16.66 mmol) and trifluoromethanesulfonic anhydride (1.4 mL, 8.33 mmol) at 0° C. The reaction mixture was then warmed to rt, and stirred overnight. 20 mL H$_2$O was added to the reaction mixture, and the separated organic layer was then concentrated to an oil-like residue, which was used for next step without further purification.

Step 3: The solution of 13-D (2.53 g, 5.55 mmol), 2-chlorophenylboronic acid (0.521 g, 3.33 mmol), and Et$_3$N (2.4 mL, 16.66 mmol) in dioxane (11 mL) was degassed with nitrogen for 5 min before Pd(PPh$_3$)$_4$ (0.641 g, 0.555 mmol) was added. The reaction mixture was heated to 100° C. for 2 h before the solvent was removed, and the residue was purified by column (silica gel, 50% EtOAc in hexanes) to afford 13-E: 1.4 g, 60% yield. 1H NMR (400 MHz, Chloroform-d) δ 8.10 (d, J=1.3 Hz, 1H), 7.85 (s, 1H), 7.47-7.41 (m, 1H), 7.34 (dtd, J=16.0, 7.4, 1.6 Hz, 2H), 7.24-7.20 (m, 1H), 4.48 (qd, J=7.1, 1.8 Hz, 2H), 2.63-2.52 (s, 3H), 2.16 (s, 3H), 1.41 (t, J=7.1 Hz, 3H). LCMS (M+H)$^+$: 418.13.

Step 4: The solution of 13-E (0.21 g, 0.50 mmol), Na$_2$CO$_3$ (0.1 g, 1.00 mmol) and 4-pyridylboronic acid (0.09 g, 0.75 mmol) in dioxane (2.2 mL) and H$_2$O (0.25 mL) was degassed for 5 min before XPhos-Pd-G3 (0.042 mg, 0.05 mmol) was added. The reaction mixture was heated to 70° C. and stirred for 2 h. The reaction mixture was directly purified by column (silica gel, EtOAc) yield 2: 0.125 g, 60% yield. $^1$H NMR (400 MHz, Chloroform-d) δ 8.70 (t, J=5.4 Hz, 2H), 8.22 (s, 1H), 7.94 (s, 1H), 7.51-7.45 (m, 1H), 7.37 (dddd, J=11.3, 6.7, 4.2, 2.9 Hz, 3H), 7.16 (dt, J=5.3, 1.1 Hz, 1H), 7.13-7.07 (m, 1H), 4.58 (qd, J=7.1, 1.8 Hz, 2H), 2.19 (d, J=1.0 Hz, 3H), 1.74 (s, 3H), 1.50 (t, J=7.1 Hz, 3H). LCMS (M+H)$^+$: 417.31.

Step 5: To a solution of 2 (0.253 g, 0.61 mmol) in MeOH (0.6 mL) was added MeNH$_2$ (0.094 g, 40% aq. solution, 3.03 mmol), and the reaction mixture was stirred overnight at rt. HPLC purification of the reaction mixture afforded 13: 0.17 g, 70% yield. $^1$H NMR (300 MHz, Chloroform-d) δ 8.70 (t, J=4.6 Hz, 2H), 8.29 (q, J=5.1 Hz, 1H), 8.07 (d, J=1.7 Hz, 1H), 7.99 (s, 1H), 7.50-7.41 (m, 1H), 7.40-7.30 (m, 3H), 7.13 (dd, J=16.4, 5.1 Hz, 2H), 3.14 (dd, J=5.3, 1.7 Hz, 3H), 2.19 (s, 3H), 1.74 (d, J=1.8 Hz, 3H). LCMS (M+H)$^+$: 402.28.

Example 2

Preparation of Compound 3

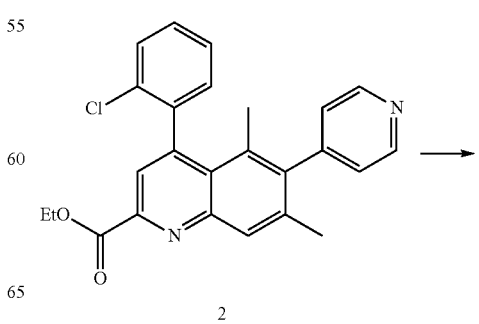

Step 1: Under Dean-Stark trap, the solution of 4-bromo-3,5-dimethylaniline (7.5 g, 37.5 mmol), diethyl oxaloacetate sodium salt (7.88 g, 37.5 mmol) and p-toluenesulfonic acid (6.46 g, 37.5 mmol) in toluene (75 mL) was heated to reflux for overnight. The solvent was slowly removed under vacuum, and the crude product was then dissolved in Ph$_2$O (20 mL). The resulting dark brown mixture was heated to 250° C. for 1 h. After 1 h, 200 mL H$_2$O was added to the reaction mixture, and the suspension was filtered. The solid collected was then washed with Et$_2$O, dried overnight to yield 13-C without further purification (10 g, 83% yield). $^1$H

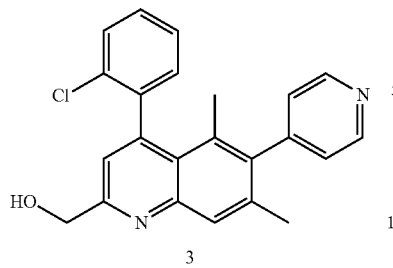

3

To a solution of 2 (15 mg, 0.036 mmol) in THF (0.36 mL) was added LiAlH$_4$ (1.4 mg, 0.036 mmol), and the mixture was stirred for 30 min at rt before it was quenched with H$_2$O. The suspension was then purified by column (silica gel, EtOAc) to yield 3: 7 mg, 52% yield. 1H NMR (400 MHz, Chloroform-d) δ 8.70 (t, J=5.2 Hz, 2H), 7.99 (s, 1H), 7.50-7.44 (m, 1H), 7.41-7.29 (m, 3H), 7.16 (ddd, J=5.1, 1.9, 0.9 Hz, 1H), 7.11 (ddd, J=5.2, 1.8, 0.9 Hz, 1H), 7.08 (s, 1H), 4.96 (d, J=4.2 Hz, 2H), 4.41 (s, 1H), 2.19 (d, J=0.9 Hz, 3H), 1.72 (s, 3H). LCMS (M+H)$^+$: 375.22.

Example 3

Preparation of Compound 4

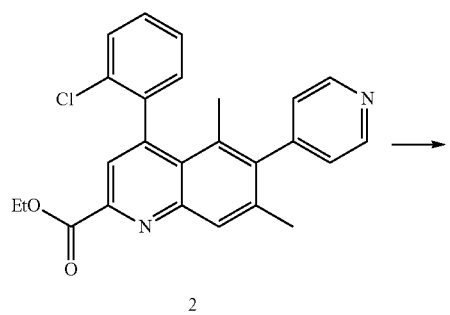

To a solution of 2 (27 mg, 0.065 mmol) in THF (0.65 mL) at −20° C. was added MeMgBr (0.10 mL, 3M solution, 0.32 mmol), and the reaction mixture was stirred for 1 h at −20° C. After warming to rt, the reaction mixture was directly purified by column (siliga gel, EtOAc) to yield 4: 9 mg, 35% yield. 1H NMR (400 MHz, Chloroform-d) δ 8.61 (d, J=5.4 Hz, 2H), 7.90 (s, 1H), 7.42-7.37 (m, 1H), 7.33-7.21 (m, 3H), 7.13 (s, 1H), 7.08-7.03 (m, 1H), 7.03-6.96 (m, 1H), 2.09 (s, 3H), 1.62 (s, 3H), 1.55 (s, 6H). LCMS (M+H)$^+$: 403.35.

Example 4

Preparation of Compounds 5 and 6

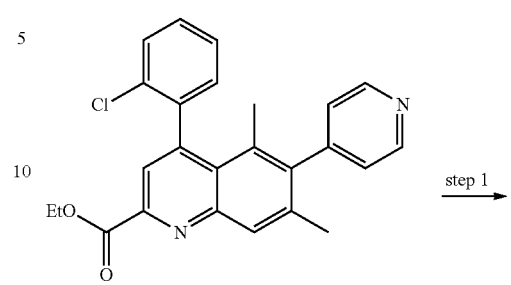

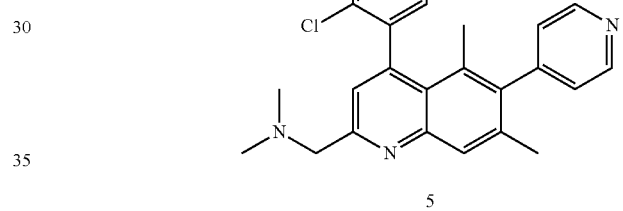

Step 1: To a solution of 2 (44 mg, 0.11 mmol) in DCM (1.1 mL) at −78° C. was added DIBAL-H (0.056 mL, 0.32 mmol) dropwise, and the mixture was stirred for 2 h at −78° C. before it was quenched with sat. Na$_2$S$_2$O$_3$ solution. The suspension was then filtered through a pad of silica gel to produce the crude aldehyde 5-A: 24 mg, 61% yield.

Step 2: To a solution of 5-A (24 mg, 0.064 mmol) in DCE (1.3 mL) was added dimethylamine (0.13 mL, 0.26 mmol), and the mixture was stirred for 30 min at rt before NaBH(OAc)$_3$ (55 mg, 0.26 mmol) was added. The reaction mixture was stirred overnight at rt, and then directly purified by HPLC to yield 5: 5 mg, 19% yield. 1H NMR (400 MHz, Chloroform-d) δ 8.59 (td, J=5.0, 0.8 Hz, 2H), 7.91 (s, 1H), 7.38-7.33 (m, 1H), 7.29-7.22 (m, 4H), 7.04 (dddd, J=19.2, 5.1, 1.8, 0.9 Hz, 2H), 3.72 (s, 2H), 2.28 (s, 6H), 2.08 (d, J=0.9 Hz, 3H), 1.63 (s, 3H). LCMS (M+H)$^+$: 402.32.

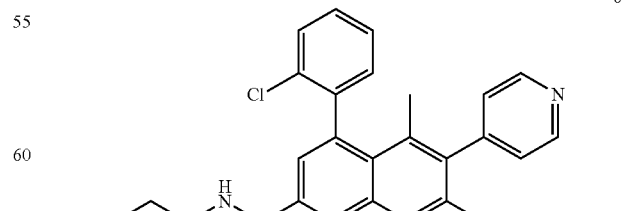

Compound 6 was prepared using similar method as 5. 1H NMR (400 MHz, Methanol-d4) δ 8.63 (td, J=5.1, 0.9 Hz, 2H), 7.94 (s, 1H), 7.53-7.48 (m, 1H), 7.47-7.38 (m, 3H), 7.33 (s, 1H), 7.27 (dddd, J=7.9, 5.1, 1.9, 0.9 Hz, 2H), 4.11

(s, 2H), 3.71 (t, J=5.5 Hz, 2H), 2.84 (t, J=5.5 Hz, 2H), 2.20-2.12 (m, 3H), 1.72 (s, 3H). LCMS (M+H)+: 418.33.

Example 5

Preparation of Compounds 7-9

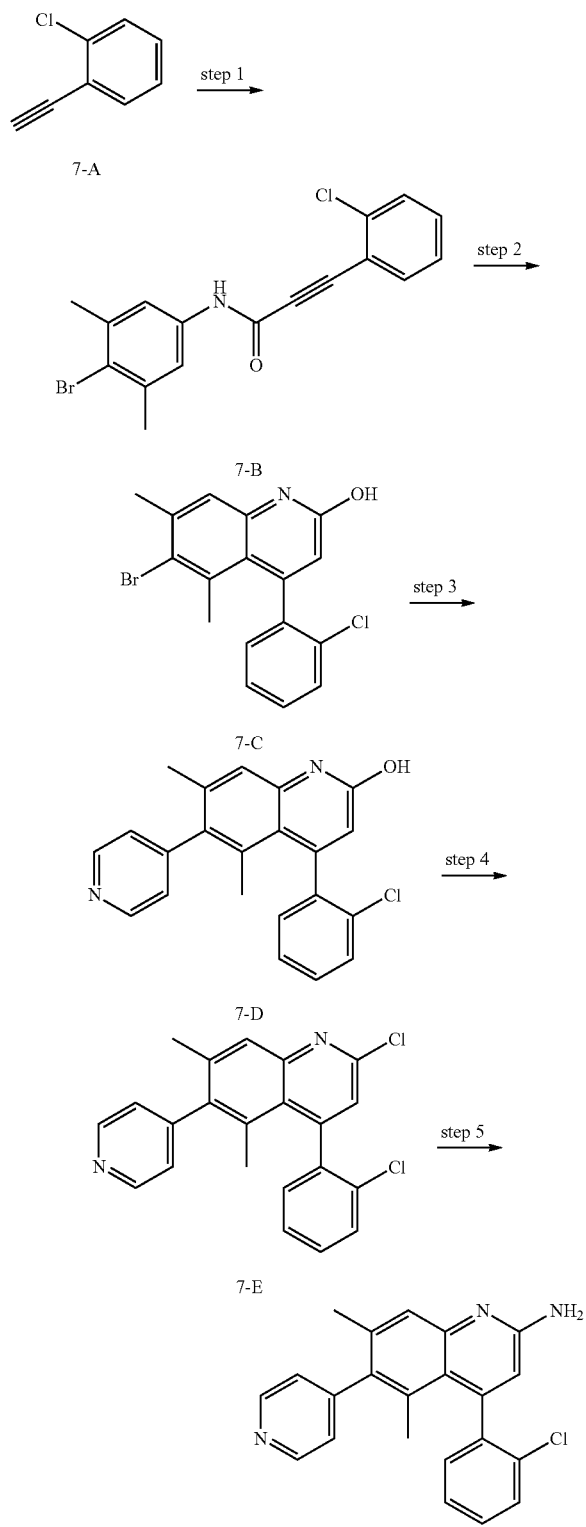

Step 1: To a solution of 1-chloro-2-ethynylbenzene (4.5 g, 32.9 mmol) in THF (66 mL) was added BuLi (22.7 mL, 1.6 M, 36.2 mmol) at −78° C., and the mixture was stirred for 1 h at −78° C. Powered dry ice (7.25 g, 165 mmol) was then added, and the mixture was allowed to warm to rt, and stirred for 1 h. The reaction was quenched with sat. aq. NaCl, acidified with 1N HCl, extracted with EtOAc. The combined organic layers were washed with water, sat. aq. NaCl, dried over $Na_2SO_4$ and concentrated under vacuum to give 3-(2-chlorophenyl)propiolic acid (6 g, 100 yield), which was used in the next step directly.

To a solution of 3-(2-chlorophenyl)propiolic acid (6 g, 33.2 mmol) in DCM (100 mL) was added 4-bromo-3,5-dimethylaniline (6.65 g, 33.2 mmol), EDCI (9.55 g, 49.8 mmol), HOBt (7.63 g, 49.8 mmol), $iPr_2EtN$ (11.6 mL, 66.4 mmol) and DMAP (0.41 g, 3.32 mmol), and the reaction mixture was stirred for overnight at rt. The reaction mixture was then washed with 1N HCl, 1N NaOH, $H_2O$ followed by sat. NaCl, dried over $Na_2SO_4$, filtered and concentrated. The residue was purified by column (Silica gel) to give 7-B: 5.1 g, 42% yield. 1H NMR (300 MHz, DMSO-d6) δ 10.93 (s, 1H), 7.76 (dd, J=7.6, 1.8 Hz, 1H), 7.65 (dd, J=8.0, 1.3 Hz, 1H), 7.55 (td, J=7.8, 1.8 Hz, 1H), 7.50-7.39 (m, 3H), 2.34 (s, 6H).

Step 2: The solution of 7-B (5.1 g, 14.1 mmol) in trifluoromethanesulfonic acid (20 mL) was heated to 70° C. and stirred overnight. The reaction mixture was poured into the ice, and the resulting suspension was filtered to collect solid, which was washed with $Et_2O$ and hexanes to give 7-C: 4.8 g, 94% yield. 1H NMR (300 MHz, DMSO-d6) δ 12.01 (s, 1H), 7.73-7.34 (m, 4H), 7.28 (s, 1H), 6.23 (s, 1H), 2.43 (s, 3H), 1.92 (s, 3H).

Step 3: The mixture of 7-C (2.0 g, 5.51 mmol), 4-pyridyl-boronic acid (1.36 g, 11.0 mmol), $Na_2CO_3$ (2.34 g, 22.1 mmol) in dioxane (50 mL) and $H_2O$ (5 mL) were degassed for 5 min before XPhos-Pd-G2 (0.117 g, 0.138 mmol) was added. The reaction mixture was heated to 100° C. and stirred for 3 d under nitrogen. The mixture was purified by column (silica gel) to yield 7-D: 0.92 g, 46% yield. 1H NMR (300 MHz, DMSO-d6) δ 11.99 (s, 1H), 8.60 (d, J=4.7 Hz, 2H), 7.59-7.49 (m, 1H), 7.48-7.39 (m, 3H), 7.25 (s, 1H), 7.19-7.10 (m, 2H), 6.20 (d, J=1.7 Hz, 1H), 1.97 (d, J=4.5 Hz, 3H), 1.41 (s, 3H).

Step 4: The solution of 7-D (0.92 g, 2.55 mmol) in $POCl_3$ (10 mL) was heated to reflux for 5 h before it was cooled to rt. The reaction mixture was slowly poured into ice water, and then basified with 2M NaOH to pH=8. The mixture was then extracted with $CH_2Cl_2$, and the organic layer was dried over $Na_2SO_4$, filtered, and concentrated. The residue was then purified by column (silica gel) to yield 7-E: 0.13 g, 13% yield. 1H NMR (300 MHz, DMSO-d6) δ 8.99 (d, J=6.0 Hz, 2H), 8.04-7.89 (m, 3H), 7.60 (dq, J=5.6, 1.9 Hz, 1H), 7.57-7.46 (m, 3H), 7.42 (s, 1H), 2.14 (s, 3H), 1.60 (s, 3H).

Step 5: The mixture of 7-E (20 mg, 0.053 mmol), acetamide (125 mg, 2.11 mmol) and $K_2CO_3$ (36 mg, 0.26 mmol) was heated to 200° C. before it was purified by HPLC to yield 7: 5.2 mg, 27% yield. 1H NMR (400 MHz, Chloroform-d) δ 8.64 (t, J=5.0 Hz, 2H), 7.61 (s, 1H), 7.48-7.27 (m, 4H), 7.21-6.87 (m, 2H), 6.54 (s, 1H), 5.73 (s, 2H), 2.09 (s, 3H), 1.59 (s, 3H). LCMS (M+H)+: 360.27.

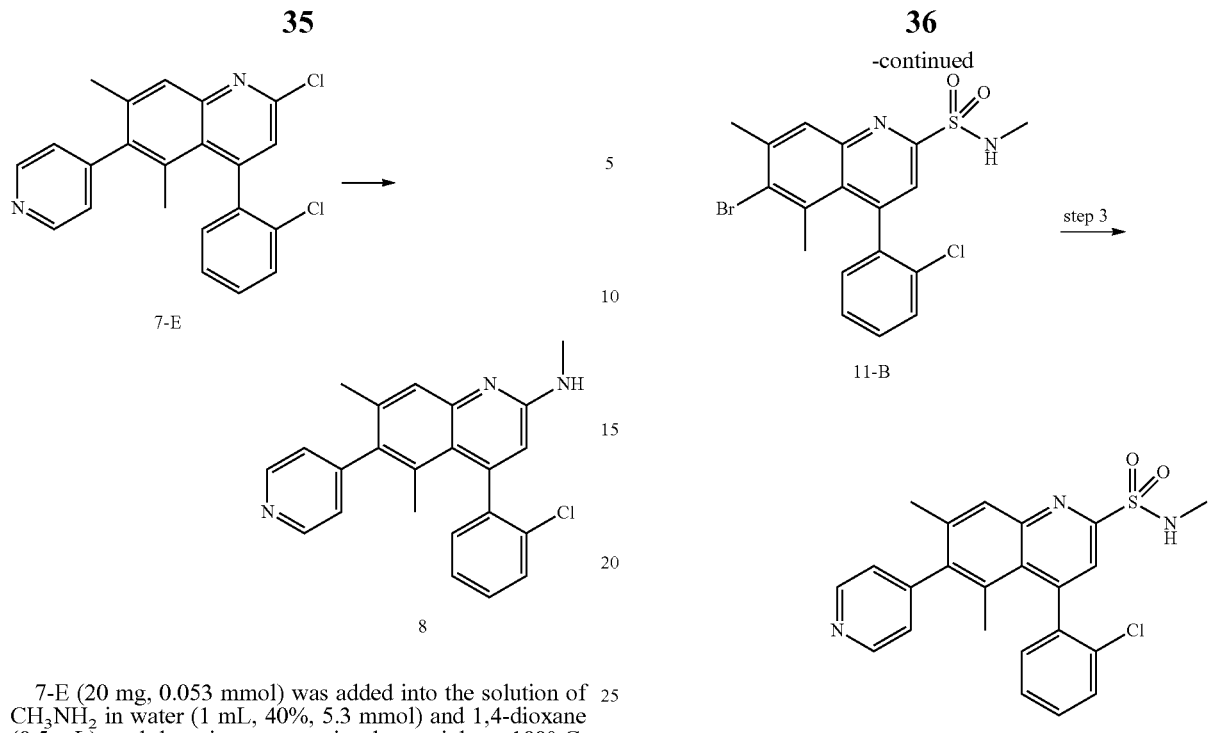

7-E

8

7-E (20 mg, 0.053 mmol) was added into the solution of CH$_3$NH$_2$ in water (1 mL, 40%, 5.3 mmol) and 1,4-dioxane (0.5 mL), and the mixture was stirred overnight at 100° C. The mixture was then purified by flash column (silica gel) to yield 8: 17 mg, 86% yield). 1H NMR (300 MHz, Methanol-d4) δ 8.55 (ddd, J=5.0, 3.0, 1.0 Hz, 2H), 7.58 (s, 1H), 7.54-7.27 (m, 4H), 7.25-7.10 (m, 2H), 6.46 (s, 1H), 3.04 (s, 3H), 2.06 (d, J=0.9 Hz, 3H), 1.56 (s, 3H). LCMS (M+H)$^+$: 374.32.

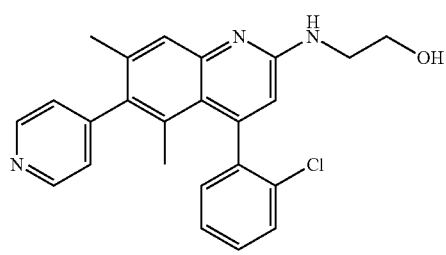

9

9 was prepared using similar method as 8: 1H NMR (300 MHz, Methanol-d4) δ 8.56 (ddd, J=4.8, 3.4, 1.0 Hz, 2H), 7.50 (s, 1H), 7.49-7.25 (m, 4H), 7.25-7.13 (m, 2H), 6.53 (s, 1H), 3.81 (t, J=5.3 Hz, 2H), 3.63 (t, J=5.3 Hz, 2H), 2.06 (s, 3H), 1.57 (s, 3H). LCMS (M+H)$^+$: 431.36.

Example 6

Preparation of Compound 11

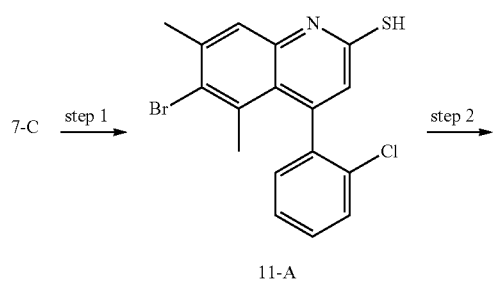

11-B

11

Step 1: The solution of 7-C (300 mg, 0.83 mmol) and Lawesson's reagent (669 mg, 1.65 mmol) in dioxane (10 mL) was heated at 100° C. for 3 h. The mixture was purified directly by flash column (silica gel) to give 11-A as yellow solid: 250 mg. 1H NMR (400 MHz, Chloroform-d) δ 12.65 (s, 1H), 7.88-7.27 (m, 5H), 7.26-7.06 (m, 1H), 2.57 (s, 3H), 2.10 (s, 3H).

Step 2: The solution of 11-A (225 mg, 0.59 mmol) and HCl (1.8 mL, 12 M, 21.4 mmol) in DCM (1.7 mL) was cooled to −10° C. before NaClO solution (2.8 mL, 12%, 3.56 mmol) was added dropwise. After the addition, a pre-cooled solution of MeNH$_2$ (6.22 mL, 40%, 71.3 mmol) was added, and the mixture was stirred for 30 min at 0° C. The reaction mixture was extracted with DCM, and the combined organic layer was dried over Na$_2$SO$_4$, filtered, and concentrated. The residue was purified by column (silica gel) to yield 11-B: 50 mg, 19% yield. 1H NMR (300 MHz, Chloroform-d) δ 8.04 (t, J=1.1 Hz, 1H), 7.82 (d, J=1.4 Hz, 1H), 7.56-7.49 (m, 1H), 7.42 (dtd, J=13.3, 7.3, 1.8 Hz, 2H), 7.33-7.23 (m, 1H), 5.27 (q, J=5.3 Hz, 1H), 2.88 (d, J=5.2 Hz, 3H), 2.64 (dd, J=12.8, 1.0 Hz, 3H), 2.21 (d, J=19.9 Hz, 3H).

Step 3: The solution of 11-B (50 mg, 0.11 mmol), Na$_2$CO$_3$ (48 mg, 0.46 mmol), 4-pyridylboronic acid (21 mg, 0.17 mmol) in dioxane (2 mL) and H$_2$O (0.2 mL) was degassed with nitrogen for 5 min before Xphos-Pd-G2 (9 mg, 0.01 mmol) was added. The reaction mixture was heated to 50° C. for 6 h before it was directly purified by column (silica gel) to yield 11: 10 mg, 20% yield. 1H NMR (400 MHz, Chloroform-d) δ 8.70 (t, J=4.8 Hz, 2H), 8.07 (s, 1H), 7.80 (s, 1H), 7.46 (dd, J=7.2, 1.9 Hz, 1H), 7.43-7.28 (m, 3H), 7.20-7.01 (m, 2H), 5.16 (q, J=5.3 Hz, 1H), 2.88 (d, J=5.3 Hz, 3H), 2.18 (s, 3H), 1.73 (s, 3H). LCMS (M+H)$^+$: 438.31.

Example 7

Preparation of Compounds 12-17, 21-29, 33-35, 37-46

Preparation of compounds 12-17, 21-29, 33-35 followed similar method as described for compound 13 in example 1.

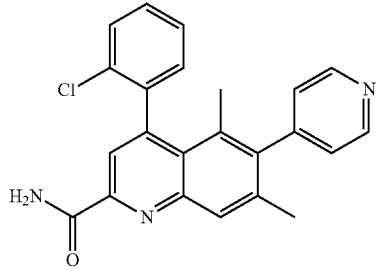
12

10% yield. $^1$H NMR (300 MHz, Chloroform-d) δ 8.71 (t, J=4.8 Hz, 2H), 8.12 (s, 1H), 8.07 (s, 1H), 8.02 (s, 1H), 7.40-7.30 (m, 3H), 7.20-7.07 (m, 2H), 2.20 (d, J=1.0 Hz, 3H), 1.76 (s, 3H). LCMS (M+H)$^+$: 388.25.

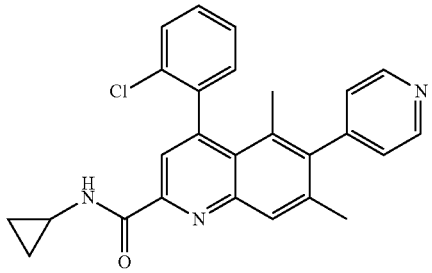
14

56% yield. $^1$H NMR (400 MHz, Chloroform-d) δ 8.63 (s, 2H), 8.27-8.16 (m, 1H), 7.98 (s, 1H), 7.90 (s, 1H), 7.42-7.33 (m, 1H), 7.33-7.21 (m, 3H), 7.12-7.00 (m, 2H), 2.94 (tq, J=7.5, 3.9 Hz, 1H), 2.10 (d, J=1.0 Hz, 3H), 1.65 (s, 3H), 0.93-0.80 (m, 2H), 0.69 (td, J=4.5, 4.0, 2.9 Hz, 2H). LCMS (M+H)$^+$: 428.28.

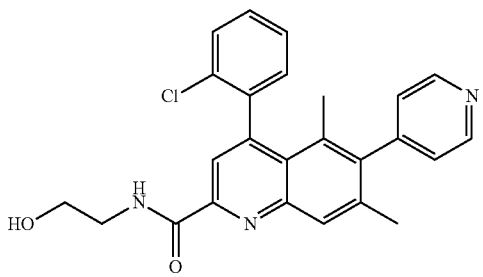
15

48% yield. $^1$H NMR (400 MHz, Chloroform-d) δ 8.66 (t, J=5.9 Hz, 1H), 8.05 (s, 1H), 8.00 (s, 1H), 7.47-7.41 (m, 1H), 7.40-7.27 (m, 3H), 3.97-3.87 (m, 2H), 3.75 (td, J=5.8, 4.2 Hz, 2H), 2.18 (s, 3H), 1.73 (s, 3H). LCMS (M+H)$^+$: 432.34.

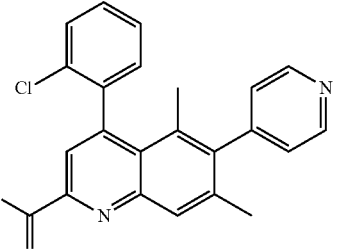
16

70% yield. $^1$H NMR (400 MHz, Chloroform-d) δ 8.74-8.66 (m, 2H), 8.55 (t, J=5.3 Hz, 1H), 8.06 (s, 1H), 8.04 (s, 1H), 7.48-7.42 (m, 1H), 7.40-7.30 (m, 3H), 7.14 (ddt, J=21.8, 4.5, 1.1 Hz, 2H), 3.67 (qd, J=6.2, 1.9 Hz, 2H), 2.65 (t, J=6.2 Hz, 2H), 2.38 (s, 6H), 2.20 (d, J=1.0 Hz, 3H), 1.75 (s, 3H). LCMS (M+H)$^+$: 459.32.

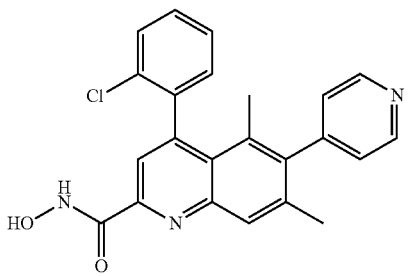
17

35% yield. $^1$H NMR (400 MHz, Chloroform-d) δ 10.42 (s, 1H), 8.72-8.57 (m, 3H), 7.91 (s, 1H), 7.89 (s, 1H), 7.40-7.33 (m, 1H), 7.32-7.20 (m, 4H), 7.13-7.03 (m, 3H), 2.10 (d, J=1.0 Hz, 3H), 1.65 (s, 3H). LCMS (M+H)$^+$: 404.24.

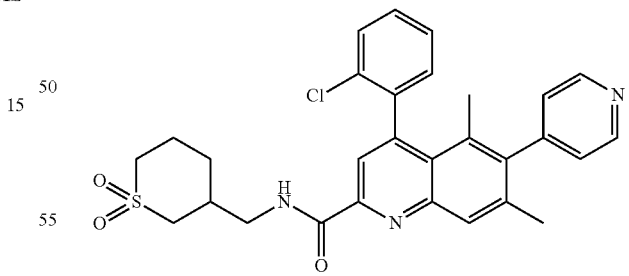
21

87% yield. 1H NMR (400 MHz, Chloroform-d) δ 8.71 (t, J=5.2 Hz, 2H), 8.49-8.41 (m, 1H), 8.03 (s, 1H), 8.02 (t, J=1.0 Hz, 1H), 7.49-7.43 (m, 1H), 7.41-7.31 (m, 3H), 7.20-7.07 (m, 2H), 3.70-3.50 (m, 2H), 3.29-3.20 (m, 1H), 3.13-3.04 (m, 1H), 2.98-2.80 (m, 2H), 2.65-2.50 (m, 1H), 2.21 (s, 3H), 2.19-2.00 (m, 2H), 1.75 (s, 3H), 1.45-1.27 (m, 1H). LCMS (M+H)$^+$: 534.32.

22

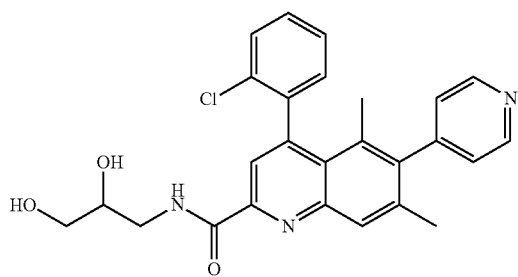

87% yield. 1H NMR (400 MHz, Chloroform-d) δ 8.71 (m, 3H), 8.04 (s, 1H), 8.02-7.98 (m, 1H), 7.48-7.41 (m, 1H), 7.40-7.30 (m, 3H), 7.13 (dddd, J=21.8, 5.1, 1.8, 0.9 Hz, 2H), 4.05-3.95 (m, 1H), 3.83-3.66 (m, 5H), 2.18 (s, 3H), 1.74 (s, 3H). LCMS (M+H)+: 462.35.

23

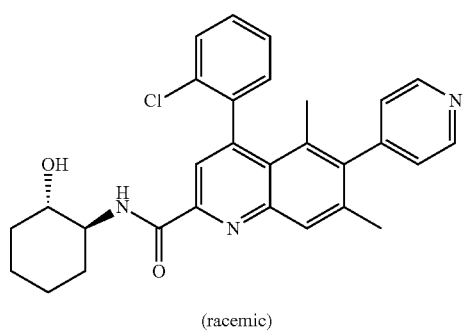

(racemic)

53% yield. 1H NMR (400 MHz, Chloroform-d) δ 8.72 (t, J=5.5 Hz, 2H), 8.31 (d, J=7.7 Hz, 1H), 8.07 (d, J=1.0 Hz, 1H), 8.05-7.99 (m, 1H), 7.49-7.43 (m, 1H), 7.41-7.32 (m, 3H), 7.22-7.10 (m, 2H), 3.93 (ddt, J=9.5, 3.8, 1.8 Hz, 1H), 3.62 (ddd, J=10.3, 6.4, 3.7 Hz, 1H), 3.47 (s, 1H), 2.21 (s, 3H), 2.17 (dq, J=4.6, 2.2 Hz, 2H), 1.84 (dt, J=12.7, 3.0 Hz, 2H), 1.76 (s, 3H), 1.61-1.26 (m, 5H). LCMS (M+H)+: 486.34.

24

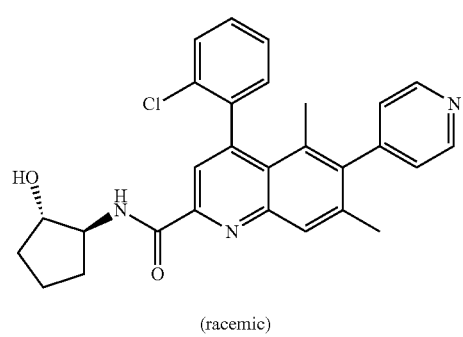

(racemic)

94% yield. 1H NMR (400 MHz, Chloroform-d) δ 8.72 (t, J=5.3 Hz, 2H), 8.38 (d, J=4.8 Hz, 1H), 8.06 (s, 1H), 8.04-7.99 (m, 1H), 7.49-7.43 (m, 1H), 7.41-7.32 (m, 3H), 7.20-7.09 (m, 2H), 4.52 (s, 1H), 4.23 (qd, J=6.6, 3.2 Hz, 1H), 4.17-4.07 (m, 1H), 2.44-2.30 (m, 1H), 2.20 (s, 3H), 2.17-2.09 (m, 1H), 2.02-1.78 (m, 4H), 1.76 (s, 3H). LCMS (M+H)+: 472.34.

25

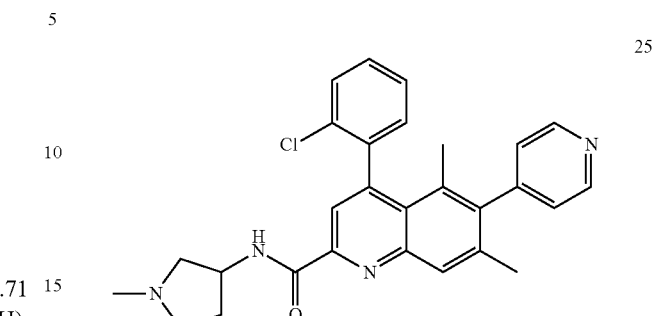

27% yield. 1H NMR (400 MHz, Chloroform-d) δ 8.75-8.66 (m, 2H), 8.55 (d, J=8.4 Hz, 1H), 8.04 (m, 2H), 7.50-7.43 (m, 1H), 7.41-7.31 (m, 3H), 7.14 (m, 2H), 4.77 (dt, J=7.4, 3.9 Hz, 1H), 3.03 (s, 1H), 2.83 (dd, J=35.1, 8.7 Hz, 2H), 2.55-2.34 (m, 5H), 2.20 (s, 3H), 1.94 (q, J=5.1, 4.5 Hz, 1H), 1.75 (s, 3H). LCMS (M+H)+: 471.36.

26

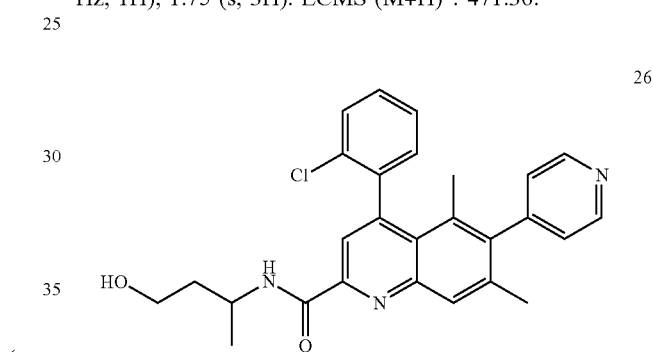

87% yield. 1H NMR (400 MHz, Chloroform-d) δ 8.72 (t, J=5.4 Hz, 2H), 8.23-8.16 (m, 1H), 8.06 (d, J=1.8 Hz, 1H), 8.03 (s, 1H), 7.49-7.42 (m, 1H), 7.41-7.32 (m, 3H), 7.19-7.08 (m, 2H), 4.49 (dtt, J=8.7, 4.7, 1.4 Hz, 1H), 3.76-3.62 (m, 3H), 2.21 (s, 3H), 2.04 (ddd, J=14.5, 8.0, 3.6 Hz, 1H), 1.79-1.74 (s, 3H), 1.61 (ddd, J=14.0, 8.3, 3.1 Hz, 1H), 1.47 (d, J=6.6 Hz, 3H). LCMS (M+H)+: 460.34.

27

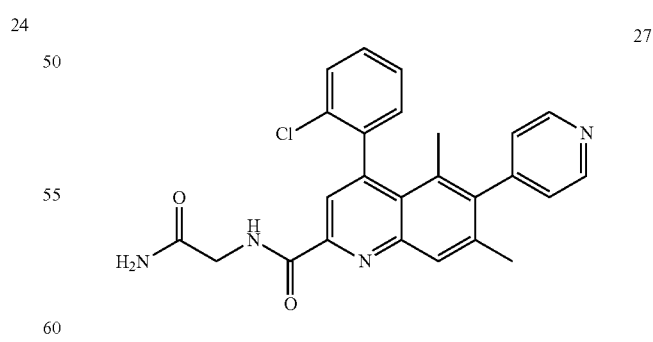

94% yield. 1H NMR (400 MHz, Chloroform-d) δ 8.88 (t, J=6.0 Hz, 1H), 8.71 (t, J=5.3 Hz, 2H), 8.04 (d, J=1.7 Hz, 2H), 7.50-7.42 (m, 1H), 7.42-7.31 (m, 3H), 7.14 (dddd, J=21.9, 5.2, 1.8, 0.9 Hz, 2H), 6.38 (s, 1H), 5.73 (s, 1H), 4.29 (d, J=5.9 Hz, 2H), 2.20 (d, J=1.0 Hz, 3H), 1.75 (s, 3H). LCMS (M+H)+: 445.36.

28

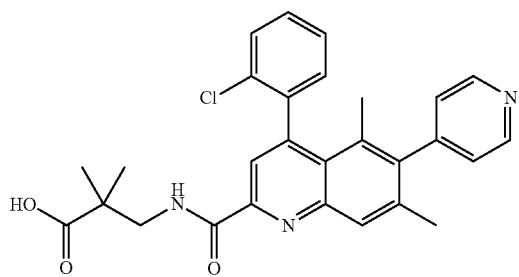

10% yield. 1H NMR (400 MHz, Chloroform-d) δ 8.81 (t, J=6.7 Hz, 1H), 8.74 (t, J=4.7 Hz, 2H), 8.07 (s, 1H), 8.02 (s, 1H), 7.48-7.42 (m, 1H), 7.40-7.31 (m, 3H), 7.16 (m, 2H), 3.80-3.67 (m, 2H), 2.14 (d, J=1.0 Hz, 3H), 1.75 (s, 3H), 1.40 (s, 6H). LCMS (M+H)$^+$: 488.35.

29

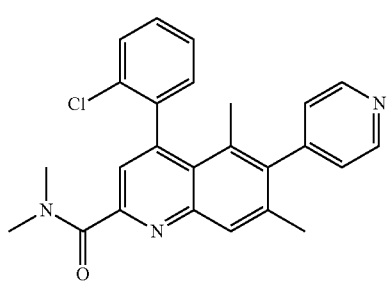

37% yield. 1H NMR (300 MHz, Chloroform-d) δ 8.72 (s, 2H), 8.05-7.99 (m, 1H), 7.50 (s, 1H), 7.48-7.43 (m, 1H), 7.42-7.32 (m, 3H), 7.19 (t, J=6.6 Hz, 2H), 3.25 (s, 3H), 3.22 (s, 3H), 2.19 (s, 3H), 1.73 (s, 3H). LCMS (M+H)$^+$: 416.33.

33

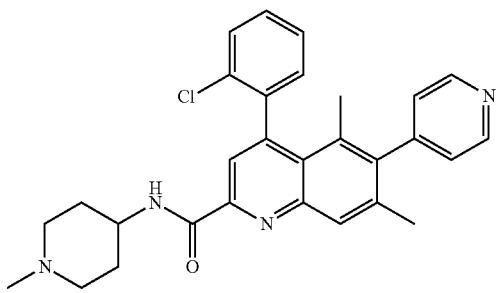

76% yield. 1H NMR (400 MHz, Chloroform-d) δ 8.72 (s, 2H), 8.20 (d, J=8.3 Hz, 1H), 8.05 (d, J=3.9 Hz, 2H), 7.49-7.43 (m, 1H), 7.41-7.30 (m, 3H), 7.19-7.08 (m, 2H), 4.07 (dt, J=9.6, 4.4 Hz, 1H), 2.96-2.83 (m, 2H), 2.36 (s, 3H), 2.26 (d, J=11.6 Hz, 1H), 2.20 (s, 3H), 2.16-2.06 (m, 2H), 1.84-1.77 (m, 1H), 1.75 (s, 3H). LCMS (M+H)$^+$: 485.31.

34

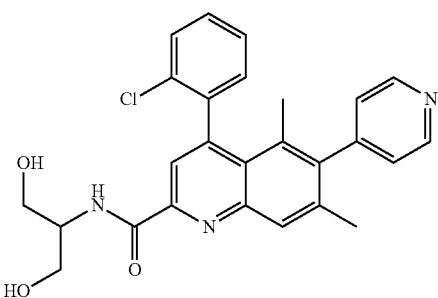

83% yield. 1H NMR (400 MHz, Chloroform-d) δ 8.89 (d, J=7.6 Hz, 1H), 8.72 (s, 2H), 8.05 (m, 2H), 7.48-7.44 (m, 1H), 7.41-7.30 (m, 3H), 7.14 (m, 2H), 4.26 (dt, J=7.6, 4.4 Hz, 1H), 4.13-3.97 (m, 5H), 3.13 (s, 2H), 2.18 (s, 3H), 1.74 (s, 3H). LCMS (M+H)$^+$: 462.30.

35

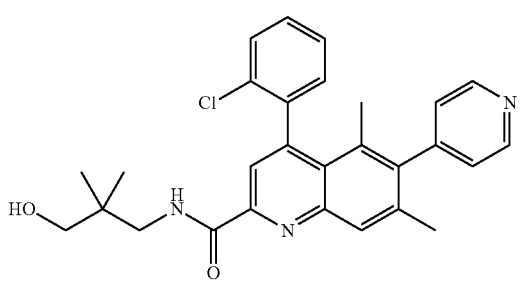

74% yield. 1H NMR (400 MHz, Chloroform-d) δ 8.71 (t, J=5.4 Hz, 2H), 8.64 (s, 1H), 8.06 (s, 1H), 8.04-7.99 (m, 1H), 7.49-7.43 (m, 1H), 7.42-7.32 (m, 3H), 7.14 (dddd, J=22.4, 5.1, 1.8, 0.9 Hz, 2H), 4.13 (s, 1H), 3.43 (dd, J=7.1, 3.2 Hz, 2H), 3.33-3.22 (m, 2H), 2.20 (d, J=1.0 Hz, 3H), 1.76 (s, 3H), 1.04 (d, J=1.2 Hz, 6H). LCMS (M+H)$^+$: 474.44.

37

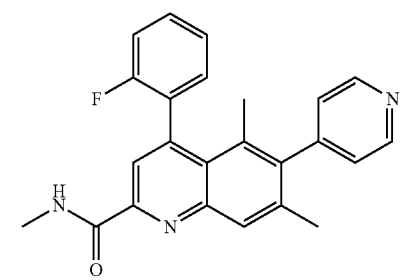

87% yield. 1H NMR (400 MHz, Chloroform-d) δ 8.75-8.66 (m, 2H), 8.30-8.22 (m, 1H), 8.14 (s, 1H), 7.99 (d, J=1.2 Hz, 1H), 7.42 (dddd, J=8.2, 7.1, 5.2, 1.9 Hz, 1H), 7.36 (td, J=7.5, 1.8 Hz, 1H), 7.24 (td, J=7.5, 1.1 Hz, 1H), 7.18 (ddd, J=5.1, 1.8, 0.9 Hz, 1H), 7.16-7.07 (m, 2H), 3.14 (d, J=5.1 Hz, 3H), 2.19 (d, J=1.0 Hz, 3H), 1.81 (s, 3H). LCMS (M+H)$^+$: 386.32.

38

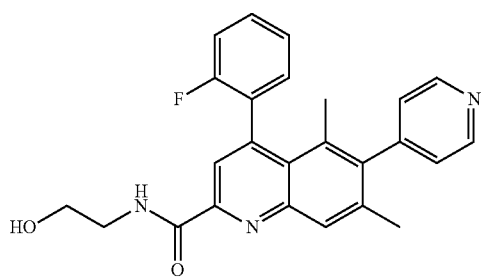

39% yield. 1H NMR (400 MHz, Chloroform-d) δ 8.70 (m, 2H), 8.64 (s, 1H), 8.11 (s, 1H), 7.99 (s, 1H), 7.37 (m, 2H), 7.14 (m, 4H), 3.93 (m, 2H), 3.74 (m, 2H), 2.18 (s, 3H), 1.79 (s, 3H). LCMS (M+H)$^+$: 416.42.

39

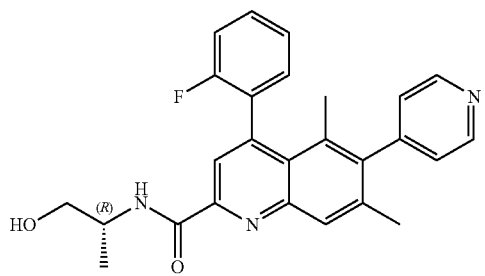

1H NMR (400 MHz, Chloroform-d) δ 8.68 (t, J=5.5 Hz, 2H), 8.37 (d, J=7.7 Hz, 1H), 8.09 (s, 1H), 8.00 (s, 1H), 7.35 (m, 2H), 7.14 (m, 4H), 4.34 (m, 1H), 3.80 (m, 2H), 3.28 (br, 1H), 2.16 (s, 3H), 1.77 (s, 3H), 1.39 (dd, J=6.8, 2.3 Hz, 3H). LCMS (M+H)$^+$: 430.38.

40

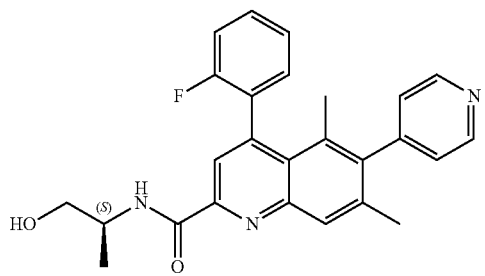

1H NMR (400 MHz, Chloroform-d) δ 8.71 (s, 2H), 8.35 (d, J=7.5 Hz, 1H), 8.11 (s, 1H), 8.02 (s, 1H), 7.37 (m, 2H), 7.18 (m, 5H), 4.33 (m, 1H), 3.79 (m, 2H), 2.85 (br, 1H), 2.18 (s, 3H), 1.79 (s, 3H), 1.41 (dd, J=6.9, 1.9 Hz, 3H). LCMS (M+H)$^+$: 430.38.

41

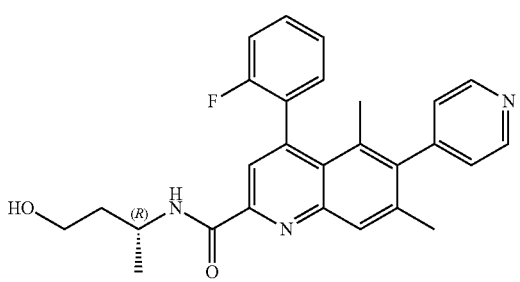

54% yield. 1H NMR (400 MHz, Chloroform-d) δ 8.72 (t, J=5.6 Hz, 2H), 8.18 (d, J=8.6 Hz, 1H), 8.13 (s, 1H), 8.03 (d, J=1.1 Hz, 1H), 7.47-7.33 (m, 2H), 7.26 (tt, J=7.4, 1.4 Hz, 1H), 7.20-7.09 (m, 3H), 4.57-4.42 (m, 1H), 3.76-3.60 (m, 3H), 2.21 (d, J=1.0 Hz, 3H), 2.10-1.96 (m, 1H), 1.82 (d, J=1.2 Hz, 3H), 1.47 (dd, J=6.7, 1.4 Hz, 3H). LCMS (M+H)$^+$: 444.52.

42

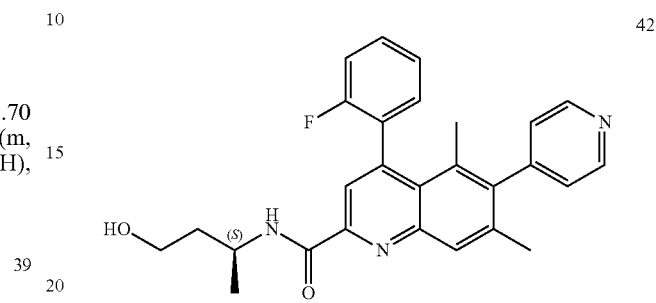

54% yield. 1H NMR (400 MHz, Chloroform-d) δ 8.72 (t, J=5.7 Hz, 2H), 8.18 (d, J=9.0 Hz, 1H), 8.13 (s, 1H), 8.06-8.00 (m, 1H), 7.47-7.33 (m, 2H), 7.26 (tt, J=7.5, 1.4 Hz, 1H), 7.20-7.08 (m, 3H), 4.56-4.41 (m, 1H), 3.78-3.60 (m, 3H), 2.21 (d, J=0.9 Hz, 3H), 2.04 (d, J=3.3 Hz, 1H), 1.82 (d, J=1.1 Hz, 3H), 1.47 (dd, J=6.8, 1.4 Hz, 3H). LCMS (M+H)$^+$: 444.47.

43

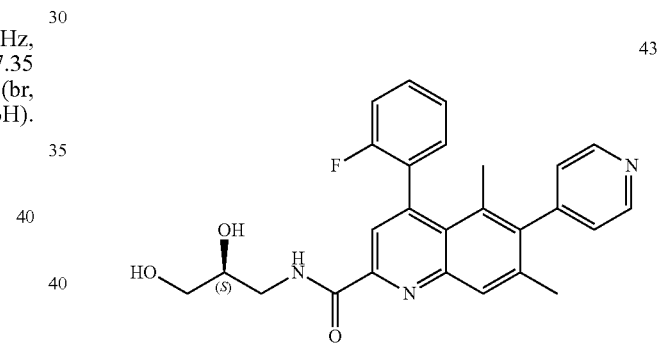

81% yield. 1H NMR (400 MHz, Chloroform-d) δ 8.72 (ddd, J=6.0, 5.0, 0.9 Hz, 2H), 8.68 (s, 1H), 8.11 (s, 1H), 8.01 (d, J=1.1 Hz, 1H), 7.42 (s, 1H), 7.39-7.32 (m, 1H), 7.26 (dd, J=7.5, 1.1 Hz, 1H), 7.20-7.07 (m, 3H), 3.99 (d, J=5.1 Hz, 1H), 3.83-3.66 (m, 4H), 2.20 (d, J=1.0 Hz, 3H), 1.81 (s, 4H). LCMS (M+H)$^+$: 446.48.

44

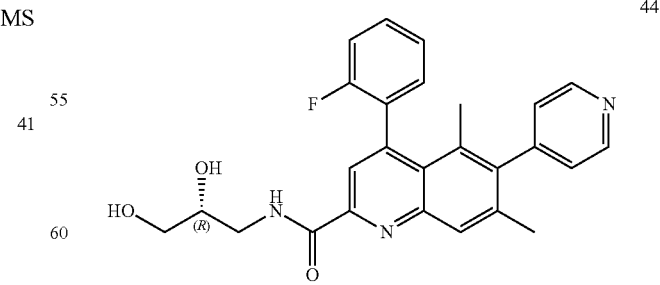

72% yield. 1H NMR (400 MHz, Chloroform-d) δ 8.72 (ddd, J=6.0, 5.0, 0.9 Hz, 2H), 8.67 (s, 1H), 8.11 (s, 1H), 8.01 (d, J=1.1 Hz, 1H), 7.47-7.39 (m, 1H), 7.36 (td, J=7.5, 1.9 Hz, 1H), 7.28-7.22 (m, 1H), 7.20-7.07 (m, 3H), 3.99 (t, J=5.1

Hz, 1H), 3.83-3.72 (m, 2H), 3.72-3.66 (m, 2H), 2.20 (d, J=1.0 Hz, 3H), 1.81 (s, 3H). LCMS (M+H)+: 446.48.

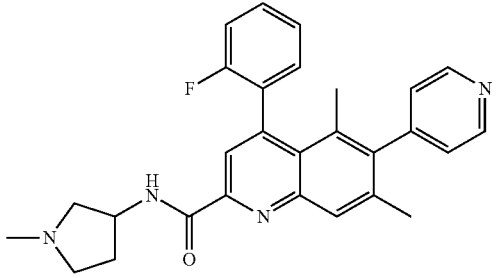

45

55% yield. 1H NMR (400 MHz, Chloroform-d) δ 8.71 (t, J=5.6 Hz, 2H), 8.55 (d, J=8.4 Hz, 1H), 8.11 (s, 1H), 8.03 (s, 1H), 7.42 (dddd, J=8.2, 7.1, 5.2, 1.8 Hz, 1H), 7.35 (td, J=7.5, 1.9 Hz, 1H), 7.24 (td, J=7.5, 1.1 Hz, 1H), 7.20-7.06 (m, 3H), 4.84-4.69 (m, 1H), 3.03 (td, J=8.6, 3.8 Hz, 2H), 2.87 (dt, J=10.2, 3.4 Hz, 1H), 2.76 (dd, J=10.1, 6.8 Hz, 1H), 2.46 (s, 3H), 2.43-2.34 (m, 1H), 2.20 (d, J=0.9 Hz, 3H), 2.00-1.85 (m, 1H), 1.80 (s, 3H). LCMS (M+H)+: 455.49.

46

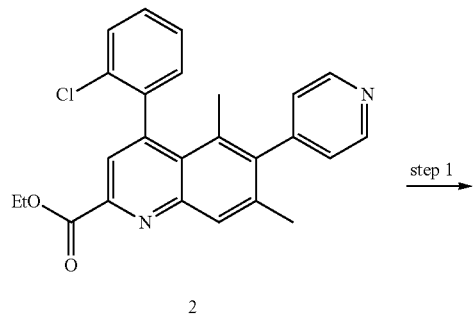

49% yield. 1H NMR (400 MHz, Chloroform-d) δ 8.71 (ddd, J=6.1, 5.0, 0.9 Hz, 2H), 8.19 (d, J=8.4 Hz, 1H), 8.12 (s, 1H), 8.06-8.01 (m, 1H), 7.47-7.32 (m, 2H), 7.24 (td, J=7.5, 1.1 Hz, 1H), 7.20-7.07 (m, 3H), 4.16-3.94 (m, 1H), 2.90 (dd, J=11.1, 4.5 Hz, 2H), 2.35 (s, 3H), 2.28-2.21 (m, 2H), 2.20 (d, J=1.0 Hz, 3H), 2.15-1.99 (m, 4H), 1.80 (s, 3H), 1.79-1.70 (m, 2H). LCMS (M+H)+: 469.49.

Example 8

Preparation of Compounds 18-20, 30-32

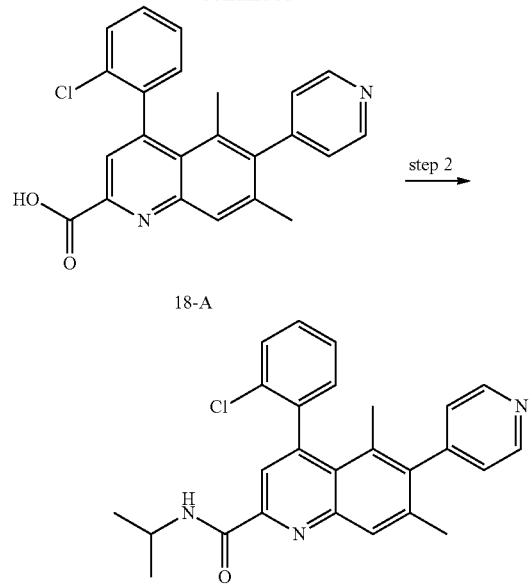

Step 1: To a solution of 2 (260 mg, 0.62 mmol) in THF (3 mL) was added 1M NaOH solution (1.2 mL), and the mixture was stirred for 2 h at rt. The mixture was acidified with HCl (1M) to pH 3. The precipitate was filtered, washed with water and ethyl ether to afford a solid, which was then azeotroped with toluene to yield 18-A: 170 mg, 70% yield.

Step 2: To a solution of 18-A (20 mg, 0.051 mmol) in DCM (1 mL) was added 2-propylamine (0.008 mL, 0.10 mmol), EDCI (15 mg, 0.077 mmol) and DMAP (6.3 mg, 0.051 mmol), and the reaction mixture was stirred overnight at rt. After completion, the reaction mixture was directly purified by column (silica gel) to yield 18: 9.8 mg, 44% yield. 1H NMR (300 MHz, Methanol-d4) δ 8.64 (d, J=5.5 Hz, 2H), 8.10 (d, J=2.6 Hz, 1H), 7.87 (d, J=1.0 Hz, 1H), 7.61-7.34 (m, 4H), 7.27 (dq, J=4.2, 1.8 Hz, 2H), 4.45-4.11 (m, 1H), 2.19 (q, J=1.4 Hz, 3H), 1.86-1.61 (m, 3H), 1.50-1.24 (m, 6H).

Compounds 19-20, 30-32 were prepared using similar method as 18.

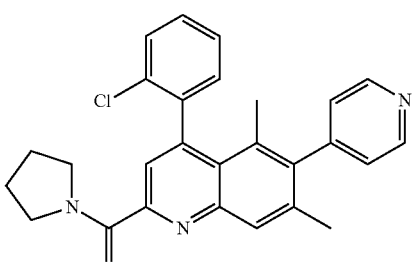

45% yield. 1H NMR (300 MHz, Methanol-d4) δ 8.64 (t, J=4.4 Hz, 2H), 8.01 (s, 1H), 7.60-7.34 (m, 5H), 7.28 (td, J=4.6, 4.1, 2.2 Hz, 2H), 3.87 (tq, J=8.5, 4.7 Hz, 2H), 3.79-3.62 (m, 2H), 2.18 (d, J=1.0 Hz, 3H), 2.12-1.89 (m, 4H), 1.73 (s, 3H). LCMS (M+H)+: 442.33.

47

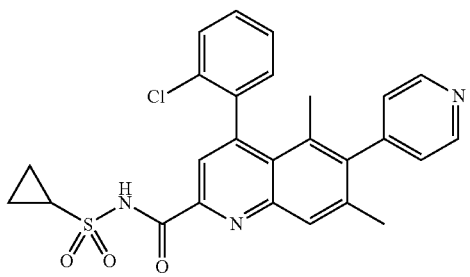

11% yield. 1H NMR (300 MHz, Methanol-d4) δ 8.71-8.46 (m, 2H), 8.08 (s, 1H), 7.80 (s, 1H), 7.57-7.27 (m, 4H), 7.19 (td, J=4.1, 2.1 Hz, 2H), 3.15-2.98 (m, 1H), 2.11 (d, J=1.0 Hz, 3H), 1.65 (s, 3H), 1.35-1.00 (m, 7H). LCMS (M+H)+: 492.18.

30

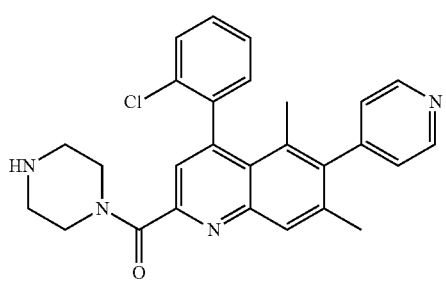

26% yield. 1H NMR (300 MHz, Methanol-d4) δ 8.65 (s, 2H), 7.99 (s, 1H), 7.67-7.36 (m, 5H), 7.28 (dd, J=5.2, 3.2 Hz, 2H), 3.88 (d, J=5.6 Hz, 2H), 3.67 (d, J=13.0 Hz, 2H), 3.03 (d, J=19.9 Hz, 3H), 2.19 (s, 3H), 1.74 (s, 3H). LCMS (M+H)+: 457.31.

31

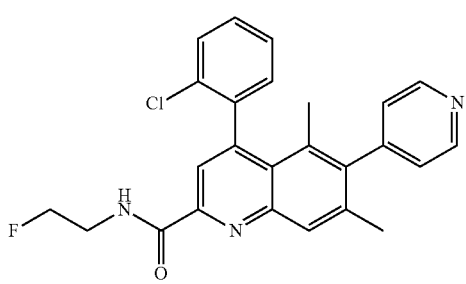

44% yield. 1H NMR (300 MHz, Methanol-d4) δ 8.73-8.58 (m, 2H), 8.11 (s, 1H), 7.88 (s, 1H), 7.59-7.34 (m, 4H), 7.33-7.21 (m, 2H), 4.72 (t, J=5.1 Hz, 1H), 4.56 (t, J=5.1 Hz, 1H), 3.85 (t, J=5.1 Hz, 1H), 3.76 (t, J=5.1 Hz, 1H), 2.19 (s, 3H), 1.73 (s, 3H). LCMS (M+H)+: 434.30.

32

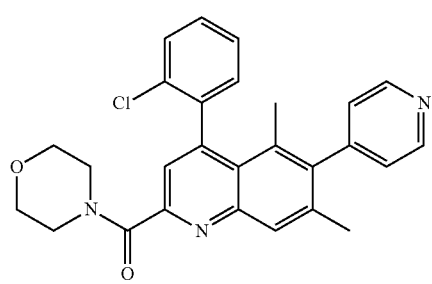

18% yield. 1H NMR (300 MHz, Methanol-d4) δ 8.65 (dd, J=5.3, 3.7 Hz, 2H), 8.02 (d, J=15.8 Hz, 2H), 7.60-7.38 (m, 5H), 7.28 (td, J=3.6, 2.9, 2.0 Hz, 2H), 3.84 (q, J=2.1 Hz, 4H), 3.79-3.60 (m, 6H), 3.49 (ddd, J=21.7, 5.6, 3.8 Hz, 2H), 2.19 (d, J=0.9 Hz, 3H), 1.74 (s, 3H). LCMS (M+H)+: 458.29.

Example 9

Preparation of Compounds 1, 47-65

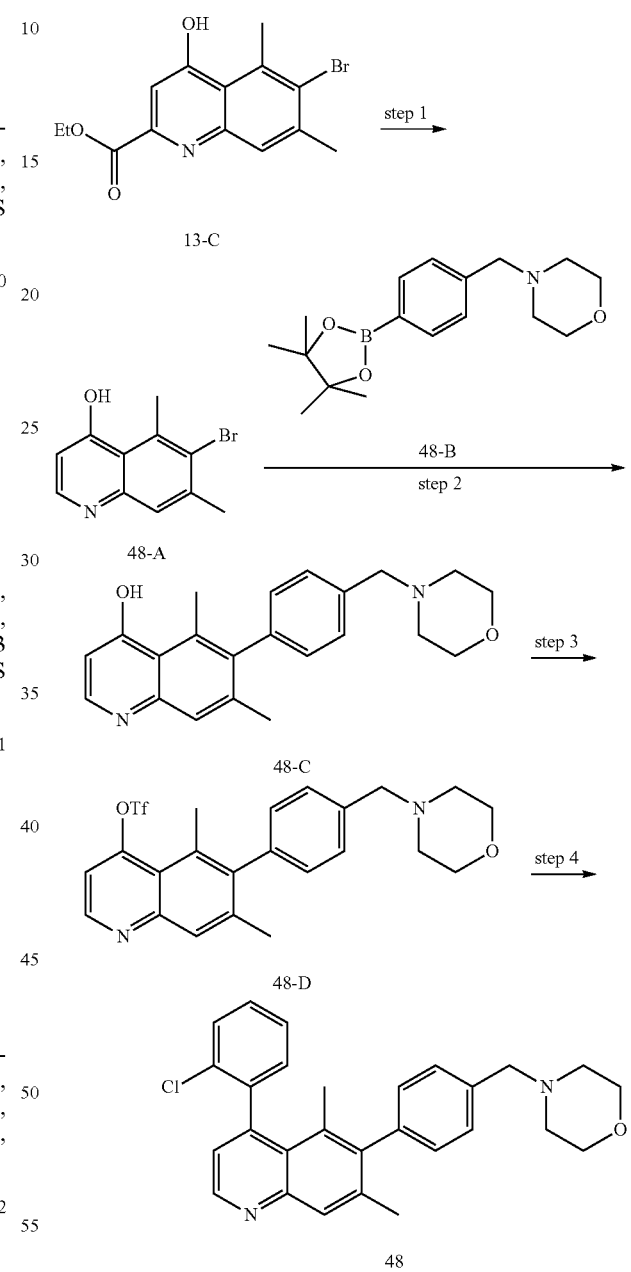

Step 1: To a solution of 13-C (2.0 g, 6.17 mmol) in THF (6 mL) was added NaOH (12.3 mL, 2.5 M, 30.8 mmol), and the mixture was stirred for 1 h at rt before it was acidified to pH=2. The suspension was then filtered, and the solid collected was dried overnight to yield the corresponding acid: 1.64 g, 90% yield. LCMS (M−H)—: 294.14, 296.14. The acid obtained above (1.64 g, 5.54 mmol) was then dissolved in 11 mL Ph₂O, and the mixture was heated to 250° C., and stirred for 1 h. After LCMS indicated completion, the reaction mixture was cooled to rt, and filtered to collect the product 48-A as dark brown solid: 1.05 g, 75% yield. 1H NMR (400 MHz, Methanol-d4) δ 7.85 (d, J=7.2 Hz, 1H), 7.38-7.30 (m, 1H), 6.31 (d, J=7.2 Hz, 1H), 3.09 (s, 3H), 2.55 (d, J=0.9 Hz, 3H).

Step 2: The solution of 48-A (478 mg, 1.90 mmol), 48-B (747 mg, 2.47 mmol), Na$_2$CO$_3$ (603 mg, 5.69 mmol) in dioxane (5.7 mL) and H$_2$O (0.6 mL) was degassed with nitrogen for 5 min before XPhos-Pd-G2 (75 mg, 0.095 mmol) was added. The reaction mixture was heated to 80° C., and stirred for 2 h. After cooling to rt, the exact solvent was removed under vacuum, and the residue was purified by column (silica gel, 25% MeOH in DCM) to yield 48-C: 329 mg, 50% yield. 1H NMR (400 MHz, Chloroform-d) δ 10.94 (s, 1H), 7.61 (d, J=7.3 Hz, 1H), 7.45-7.37 (m, 2H), 7.27 (s, 1H), 7.11-7.03 (m, 2H), 6.32 (d, J=7.2 Hz, 1H), 3.82-3.72 (m, 4H), 3.59 (s, 2H), 2.70 (s, 3H), 2.53 (t, J=4.8 Hz, 4H), 2.04 (s, 3H).

Step 3: To a solution of 48-C (329 mg, 0.94 mmol) in DCM (4.7 mL) was added Et$_3$N (0.41 mL, 2.83 mmol) followed by Tf$_2$O (0.24 mL, 1.42 mmol) at 0° C., and the reaction mixture was then warmed to rt, and stirred for 3 h. Due to the product being unstable, the mixture was then filtered through a short pad of silica gel to yield 48-D: 300 mg, 66% yield. LCMS: (M+H): 481.35.

Step 4: The solution of 48-C (35 mg, 0.073 mmol), 2-chlorophenylboronic acid (23 mg, 0.146 mmol) and Et$_3$N (0.42 mL, 0.291 mmol) in dioxane (0.4 mL) was degassed for 5 min before Pd(PPh$_3$)$_4$ (17 mg, 0.015 mmol) was added, and the reaction mixture was heated to 100° C., and stirred for overnight. The reaction mixture was purified by column (silica gel) to yield 48: 18 mg, 56% yield. $^1$H NMR (300 MHz, Chloroform-d) δ 8.88 (d, J=4.4 Hz, 1H), 7.97 (s, 1H), 7.47-7.41 (m, 1H), 7.40-7.27 (m, 5H), 7.16-7.03 (m, 3H), 3.78-3.69 (m, 4H), 3.58 (s, 2H), 2.57-2.40 (m, 4H), 2.18 (d, J=1.0 Hz, 3H), 1.70 (s, 3H).

Compounds 1, 47, 49-65 were prepared using similar method as 48.

1

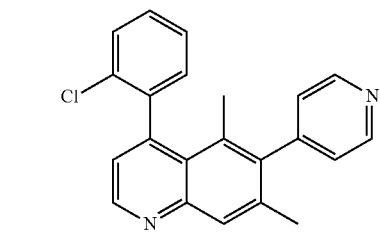

$^1$H NMR (400 MHz, Chloroform-d) δ 8.93 (d, J=4.4 Hz, 1H), 8.70 (s, 2H), 8.01 (s, 1H), 7.50-7.44 (m, 1H), 7.42-7.29 (m, 3H), 7.18 (d, J=4.4 Hz, 1H), 7.17-7.07 (m, 2H), 2.19 (d, J=1.0 Hz, 3H), 1.72 (s, 3H). LCMS (M+H)$^+$: 345.24.

47

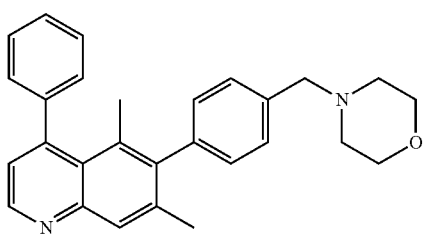

$^1$H NMR (400 MHz, Chloroform-d) δ 8.76 (d, J=4.4 Hz, 1H), 7.88 (s, 1H), 7.28 (dt, J=14.1, 6.5 Hz, 7H), 7.19 (s, 1H), 7.12 (d, J=4.3 Hz, 1H), 7.01 (d, J=7.4 Hz, 2H), 3.71-3.59 (m, 4H), 3.47 (s, 2H), 2.45-2.32 (m, 4H), 2.11 (s, 3H). LCMS (M+H)$^+$: 409.26.

49

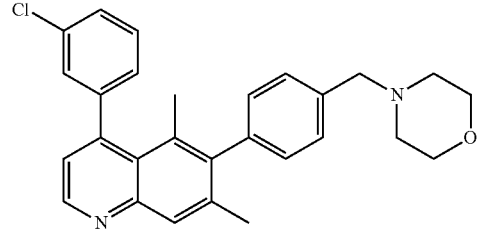

24% yield. 1H NMR (400 MHz, Chloroform-d) δ 8.87 (d, J=4.3 Hz, 1H), 7.98 (s, 1H), 7.45-7.32 (m, 5H), 7.25 (dt, J=6.7, 1.8 Hz, 1H), 7.19 (d, J=4.3 Hz, 1H), 7.11 (td, J=9.1, 2.1 Hz, 2H), 3.77 (t, J=4.8 Hz, 4H), 3.59 (s, 2H), 2.52 (m, 4H), 2.21 (d, J=1.0 Hz, 3H), 1.73 (s, 3H). LCMS (M+H)$^+$: 443.35.

50

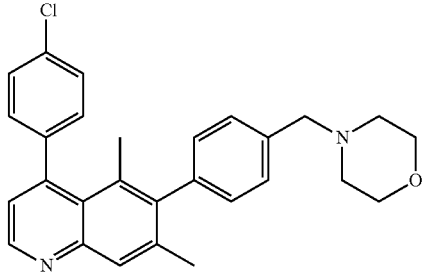

29% yield. 1H NMR (400 MHz, Chloroform-d) δ 8.86 (d, J=4.4 Hz, 1H), 7.98 (s, 1H), 7.45-7.35 (m, 4H), 7.32-7.29 (m, 2H), 7.18 (d, J=4.3 Hz, 1H), 7.13-7.06 (m, 2H), 3.77 (t, J=4.7 Hz, 4H), 3.59 (s, 2H), 2.52 (m, 4H), 2.21 (d, J=0.9 Hz, 3H), 1.71 (s, 3H). LCMS (M+H)$^+$: 443.35.

51

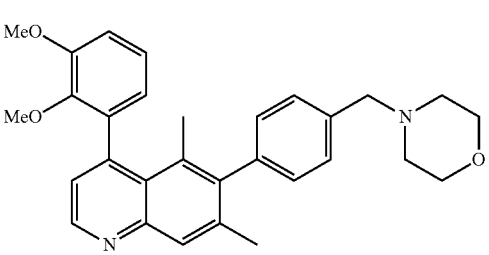

15% yield. $^1$H NMR (300 MHz, Chloroform-d) δ 8.88 (d, J=4.5 Hz, 1H), 7.97 (s, 1H), 7.40-7.30 (m, 2H), 7.23 (d, J=4.4 Hz, 1H), 7.15-7.01 (m, 3H), 6.95 (dd, J=8.3, 1.5 Hz, 1H), 6.79 (dd, J=7.6, 1.6 Hz, 1H), 3.90 (s, 3H), 3.75 (t, J=4.7 Hz, 4H), 3.61 (s, 2H), 3.55 (s, 3H), 2.54 (t, J=4.8 Hz, 4H), 2.17 (s, 3H), 1.76 (s, 3H). LCMS (M+H)$^+$: 469.11.

51

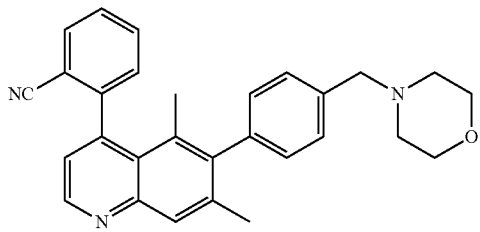

52

27% yield. ¹H NMR (300 MHz, Chloroform-d) δ 8.91 (d, J=4.3 Hz, 1H), 7.99 (s, 1H), 7.76 (ddd, J=7.6, 1.4, 0.6 Hz, 1H), 7.64 (td, J=7.7, 1.4 Hz, 1H), 7.54-7.41 (m, 2H), 7.37 (ddd, J=7.7, 3.7, 1.6 Hz, 2H), 7.20 (d, J=4.3 Hz, 1H), 7.15-7.02 (m, 2H), 3.82-3.67 (m, 4H), 3.54 (s, 2H), 2.47 (t, J=4.7 Hz, 4H), 2.19 (d, J=1.0 Hz, 3H). LCMS (M+H)⁺: 434.32.

53

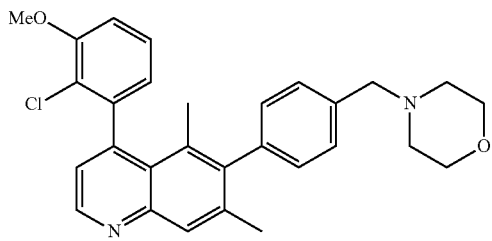

65% yield. 1H NMR (300 MHz, Chloroform-d) δ 8.89 (d, J=4.4 Hz, 1H), 7.97 (s, 1H), 7.39-7.31 (m, 2H), 7.27 (m, 1H), 7.15 (d, J=4.4 Hz, 1H), 7.12-7.03 (m, 2H), 6.94 (ddd, J=15.4, 8.0, 1.4 Hz, 2H), 3.94 (s, 3H), 3.73 (t, J=4.7 Hz, 4H), 3.57 (s, 2H), 2.50 (t, J=4.7 Hz, 4H), 2.20-2.15 (m, 3H). LCMS (M+H)⁺: 473.43.

54

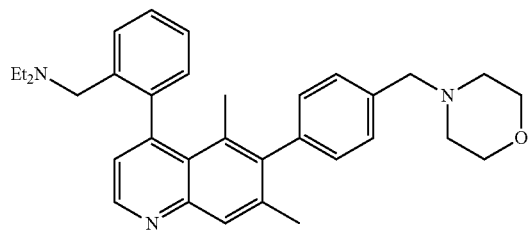

51% yield. ¹H NMR (300 MHz, Chloroform-d) δ 8.83 (d, J=4.4 Hz, 1H), 7.95 (d, J=4.1 Hz, 1H), 7.59-7.52 (m, 1H), 7.39-7.29 (m, 3H), 7.25-7.20 (m, 1H), 7.19-7.13 (m, 1H), 7.12 (d, J=4.4 Hz, 1H), 7.08-6.98 (m, 2H), 3.72 (t, J=4.7 Hz, 5H), 3.53 (s, 2H), 3.34-3.10 (m, 2H), 2.46 (t, J=4.7 Hz, 5H), 2.40-2.22 (m, 4H), 2.17 (d, J=1.1 Hz, 4H), 0.77 (t, J=7.1 Hz, 6H). LCMS (M+H)⁺: 494.40.

55

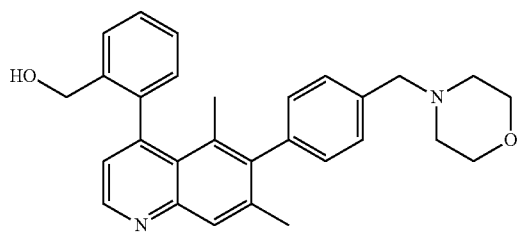

29% yield. ¹H NMR (300 MHz, Chloroform-d) δ 8.83 (d, J=4.3 Hz, 1H), 7.95 (s, 1H), 7.61-7.50 (m, 1H), 7.42 (td, J=7.5, 1.5 Hz, 1H), 7.39-7.29 (m, 3H), 7.23 (dd, J=7.6, 1.5 Hz, 1H), 7.16 (d, J=4.3 Hz, 1H), 7.08-7.00 (m, 2H), 4.40 (d, J=2.3 Hz, 2H), 3.74 (t, J=4.7 Hz, 4H), 3.58 (s, 2H), 2.50 (s, 4H), 2.17 (d, J=0.9 Hz, 3H), 1.62 (s, 3H). LCMS (M+H)⁺: 439.29.

56

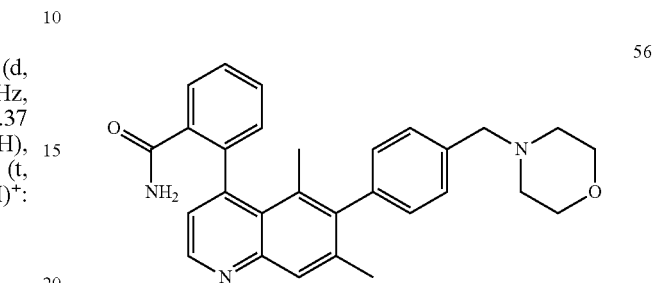

10% yield. ¹H NMR (300 MHz, Chloroform-d) δ 8.85 (d, J=4.4 Hz, 1H), 7.96 (s, 1H), 7.88-7.76 (m, 1H), 7.52-7.44 (m, 2H), 7.40-7.31 (m, 2H), 7.19 (d, J=4.3 Hz, 1H), 7.07 (td, J=8.7, 2.1 Hz, 2H), 3.72 (t, J=4.7 Hz, 4H), 3.53 (s, 2H), 2.46 (t, J=4.8 Hz, 4H), 2.18 (d, J=1.0 Hz, 3H), 1.69 (s, 3H). LCMS (M+H)⁺: 452.30.

57

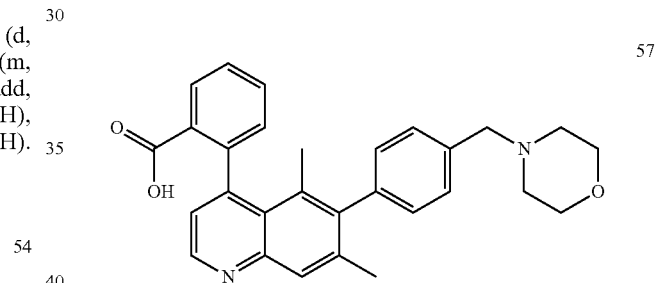

33% yield. ¹H NMR (300 MHz, Chloroform-d) δ 8.78 (d, J=4.5 Hz, 1H), 8.13-8.03 (m, 1H), 7.89 (s, 1H), 7.50-7.39 (m, 3H), 7.19 (d, J=4.5 Hz, 1H), 7.14 (td, J=6.3, 2.5 Hz, 2H), 6.98 (ddt, J=7.6, 5.5, 3.2 Hz, 2H), 6.54 (d, J=7.8 Hz, 1H), 3.65 (q, J=4.6 Hz, 4H), 3.58 (d, J=3.2 Hz, 2H), 2.59 (d, J=11.3 Hz, 5H), 2.00 (s, 3H). LCMS (M+H)⁺: 453.12.

58

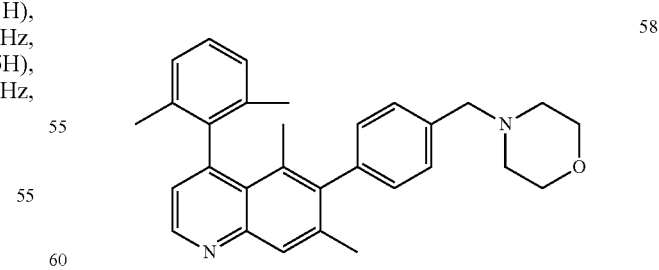

8% yield. ¹H NMR (300 MHz, Chloroform-d) δ 8.88 (d, J=4.4 Hz, 1H), 7.96 (s, 1H), 7.38-7.31 (m, 2H), 7.17 (dd, J=8.4, 6.5 Hz, 1H), 7.10-7.01 (m, 5H), 3.72 (t, J=4.7 Hz, 4H), 3.53 (s, 2H), 2.45 (q, J=5.4, 5.0 Hz, 4H), 2.17 (d, J=1.0 Hz, 3H), 1.94 (s, 6H). LCMS (M+H)⁺: 437.33.

59

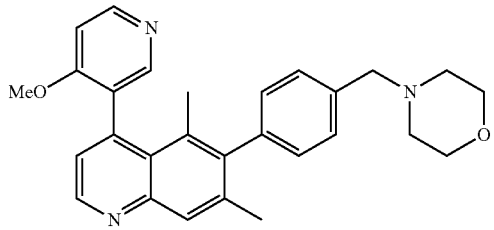

41% yield. ¹H NMR (300 MHz, Chloroform-d) δ 8.88 (d, J=4.4 Hz, 1H), 8.55 (d, J=5.8 Hz, 1H), 8.32 (s, 1H), 7.98 (s, 1H), 7.52-7.35 (m, 2H), 7.21-7.06 (m, 3H), 6.90 (d, J=5.8 Hz, 1H), 3.84 (t, J=4.7 Hz, 5H), 3.81 (s, 3H), 2.73 (s, 4H), 2.17 (d, J=1.2 Hz, 4H), 1.72 (s, 3H). LCMS (M+H)⁺: 440.21.

60

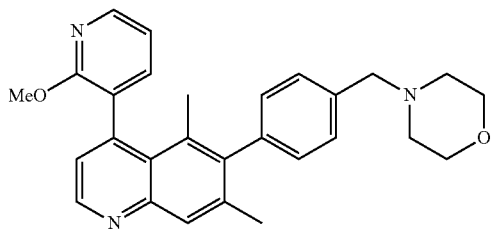

39% yield. ¹H NMR (300 MHz, Chloroform-d) δ 8.85 (d, J=4.4 Hz, 1H), 8.21 (dd, J=5.1, 1.9 Hz, 1H), 7.95 (s, 1H), 7.47 (dd, J=7.2, 1.9 Hz, 1H), 7.37 (dq, J=6.7, 2.2 Hz, 2H), 7.13 (d, J=4.3 Hz, 1H), 7.07 (td, J=8.8, 2.2 Hz, 2H), 6.97 (dd, J=7.2, 5.0 Hz, 1H), 3.87 (s, 3H), 3.77-3.66 (m, 4H), 3.54 (s, 2H), 2.52-2.41 (m, 4H), 2.18 (d, J=1.0 Hz, 3H), 1.72 (s, 3H). LCMS (M+H)⁺: 439.98.

61

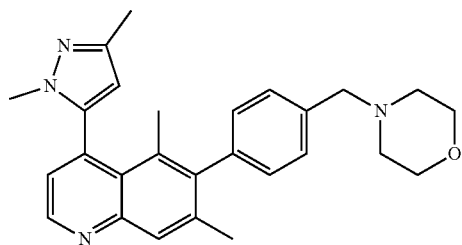

78% yield. ¹H NMR (300 MHz, Chloroform-d) δ 8.89 (d, J=4.3 Hz, 1H), 7.96 (s, 1H), 7.40 (d, J=7.6 Hz, 2H), 7.24 (d, J=4.3 Hz, 1H), 7.13-7.03 (m, 2H), 6.12 (s, 1H), 3.81-3.66 (m, 5H), 3.56 (s, 2H), 3.46 (s, 3H), 2.50 (q, J=4.8 Hz, 5H), 2.19 (d, J=1.0 Hz, 3H), 1.74 (s, 3H). LCMS (M+H)⁺: 427.25.

62

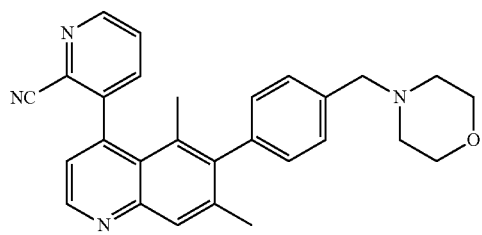

9% yield. ¹H NMR (300 MHz, Chloroform-d) δ 8.94 (d, J=4.3 Hz, 1H), 8.76 (dd, J=4.8, 1.6 Hz, 1H), 8.02 (s, 1H), 7.81 (dd, J=8.0, 1.7 Hz, 1H), 7.63-7.53 (m, 1H), 7.38 (td, J=5.7, 2.7 Hz, 2H), 7.21 (d, J=4.3 Hz, 1H), 7.13 (dd, J=8.0, 1.8 Hz, 1H), 7.06 (dd, J=7.9, 1.8 Hz, 1H), 3.73 (t, J=4.7 Hz, 4H), 3.55 (s, 2H), 2.52-2.41 (m, 4H), 2.20 (d, J=1.0 Hz, 3H), 1.65 (s, 3H). LCMS (M+H)⁺: 435.33.

63

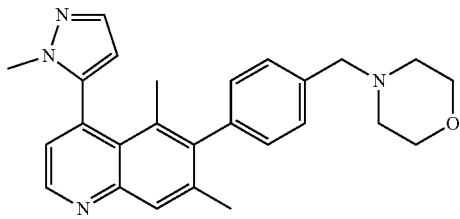

93% yield. ¹H NMR (300 MHz, Chloroform-d) δ 8.90 (d, J=4.3 Hz, 1H), 8.02-7.94 (m, 1H), 7.54 (d, J=1.9 Hz, 1H), 7.45-7.35 (m, 2H), 7.25 (d, J=4.3 Hz, 1H), 7.07 (ddd, J=8.5, 6.7, 2.2 Hz, 2H), 6.34 (d, J=1.9 Hz, 1H), 3.80-3.68 (m, 4H), 3.56 (s, 2H), 3.54 (s, 3H), 2.49 (dd, J=5.8, 3.6 Hz, 4H), 2.25-2.13 (m, 3H), 1.69 (s, 3H). LCMS (M+H)⁺: 413.26.

64

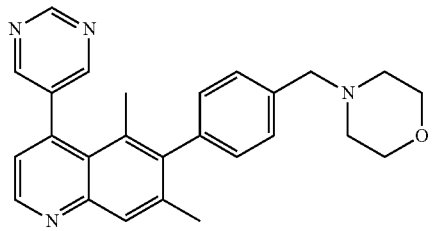 [SMILES: Cc1cc2nccc(-c3cccnc3)c2c(C)c1-c1ccc(CN2CCOCC2)cc1]

51% yield. ¹H NMR (400 MHz, Chloroform-d) δ 9.26 (s, 1H), 8.92 (d, J=4.3 Hz, 1H), 8.78 (s, 2H), 8.02 (d, J=1.2 Hz, 1H), 7.50-7.41 (m, 3H), 7.21 (d, J=4.3 Hz, 1H), 7.15-7.10 (m, 2H), 3.83 (t, J=4.7 Hz, 4H), 3.78 (s, 2H), 2.70 (s, 4H), 2.20 (d, J=1.0 Hz, 3H), 1.70 (s, 3H). LCMS (M+H)⁺: 411.60.

65

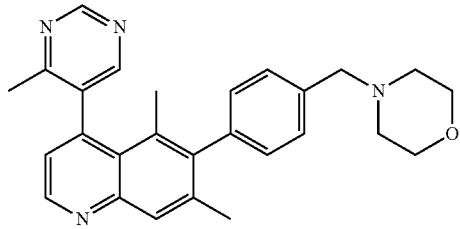

32% yield. ¹H NMR (300 MHz, Chloroform-d) δ 9.13 (s, 1H), 8.92 (d, J=4.3 Hz, 1H), 8.56 (s, 1H), 8.01 (s, 1H), 7.43-7.32 (m, 2H), 7.12 (d, J=4.3 Hz, 1H), 7.06 (ddd, J=6.8, 3.8, 1.5 Hz, 3H), 3.74 (t, J=4.7 Hz, 4H), 3.56 (s, 3H), 2.48 (t, J=4.7 Hz, 4H), 2.30 (s, 3H), 2.20 (d, J=0.9 Hz, 3H), 1.64 (s, 3H). LCMS (M+H)⁺: 424.99.

Example 10

Preparation of Compounds 66-71

Compounds 66-68 were prepared using similar method as compound 13 in example 1.

66

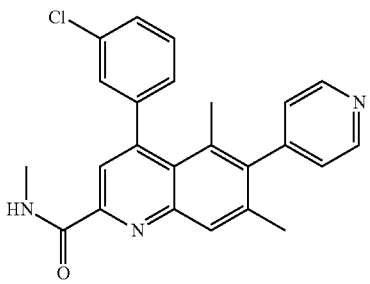

1H NMR (400 MHz, Chloroform-d) δ 8.82-8.67 (m, 2H), 8.26 (d, J=5.2 Hz, 1H), 8.11 (s, 1H), 8.04-7.94 (m, 1H), 7.43-7.34 (m, 3H), 7.25 (dt, J=7.0, 1.6 Hz, 1H), 7.19-7.11 (m, 2H), 3.14 (d, J=5.1 Hz, 3H), 2.20 (d, J=1.0 Hz, 3H), 1.75 (s, 3H). LCMS (M+H)+: 402.37.

67

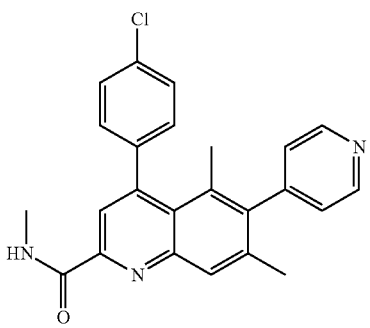

1H NMR (400 MHz, Chloroform-d) δ 8.78-8.67 (m, 2H), 8.26 (d, J=5.2 Hz, 1H), 8.11 (s, 1H), 8.01-7.95 (m, 1H), 7.47-7.38 (m, 2H), 7.32-7.29 (m, 2H), 7.21-7.10 (m, 2H), 3.14 (d, J=5.1 Hz, 3H), 2.20 (d, J=1.0 Hz, 3H), 1.74 (s, 3H). LCMS (M+H)+: 402.32.

68

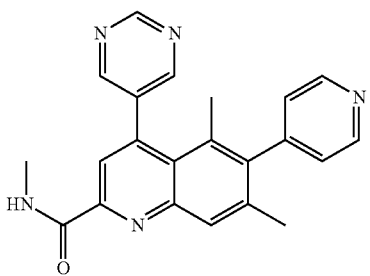

1H NMR (400 MHz, Chloroform-d) δ 9.30 (s, 1H), 8.80 (s, 2H), 8.77-8.70 (m, 2H), 8.25 (q, J=5.3 Hz, 1H), 8.14 (s, 1H), 8.06-8.01 (m, 1H), 7.16-7.09 (m, 2H), 3.15 (d, J=5.1 Hz, 3H), 2.22 (d, J=0.8 Hz, 3H), 1.74 (s, 3H). LCMS (M+H)+: 370.31.

Compounds 69-71 were also prepared similar to compound 13 showed in example 1, except the step 3 used S$_N$Ar substitution to install the cyclic amines as shown below.

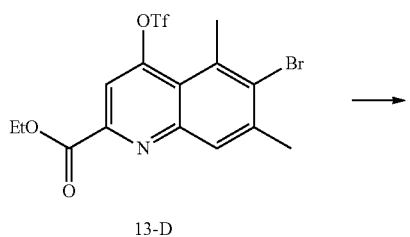

13-D

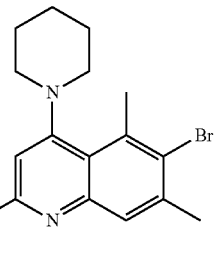

69-A

The solution of 13-D (160 mg, 0.35 mmol) and piperdine (0.10 mL, 1.05 mmol) in DMF (0.35 mL) was stirred for overnight at rt before it was directly purified by column (silica gel) to yield 69-A: 74 mg, 54% yield. LCMS (M+H)+: 391.22.

69

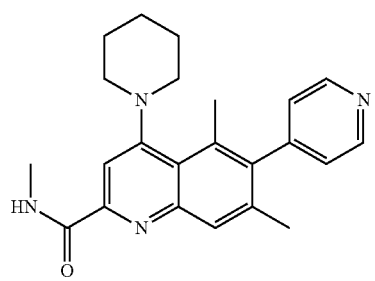

1H NMR (300 MHz, Chloroform-d) δ 8.79-8.71 (m, 2H), 8.35-8.20 (m, 1H), 7.81 (d, J=1.1 Hz, 1H), 7.78 (s, 1H), 7.17 (dt, J=4.3, 1.3 Hz, 2H), 3.51-3.37 (m, 2H), 3.09 (dd, J=5.1, 1.1 Hz, 3H), 2.78 (dt, J=13.1, 7.0 Hz, 2H), 2.58 (s, 3H), 2.12 (d, J=1.2 Hz, 3H), 1.79 (dtt, J=11.2, 7.5, 3.9 Hz, 5H), 1.48-1.32 (m, 1H). LCMS (M+H)+: 375.35.

70

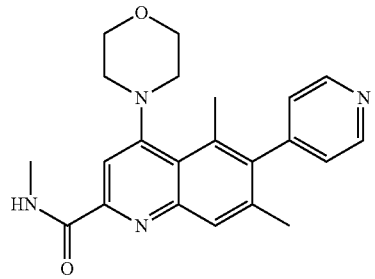

1H NMR (400 MHz, Chloroform-d) δ 8.80-8.73 (m, 2H), 8.28 (d, J=5.1 Hz, 1H), 7.83 (d, J=1.4 Hz, 2H), 7.19-7.13 (m, 2H), 3.98 (dt, J=11.4, 2.6 Hz, 2H), 3.87 (td, J=11.2, 2.2 Hz, 2H), 3.36-3.27 (m, 2H), 3.11 (d, J=5.1 Hz, 3H), 3.06-2.98 (m, 2H), 2.61 (s, 3H), 2.15 (s, 3H). LCMS (M+H)+: 377.35.

71

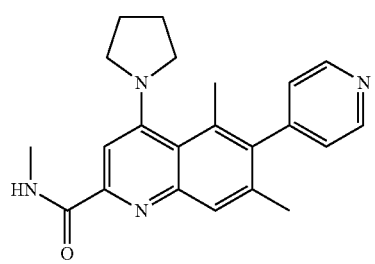

1H NMR (400 MHz, Chloroform-d) δ 8.79-8.73 (m, 2H), 7.77 (s, 1H), 7.63 (s, 1H), 7.21-7.15 (m, 2H), 3.51 (br s, 4H), 3.10 (d, J=5.0 Hz, 3H), 2.38 (s, 3H), 2.15 (s, 3H), 2.00 (m, 4H). LCMS (M+H)⁺:361.34.

Example 11

Preparation of Compounds 72-77

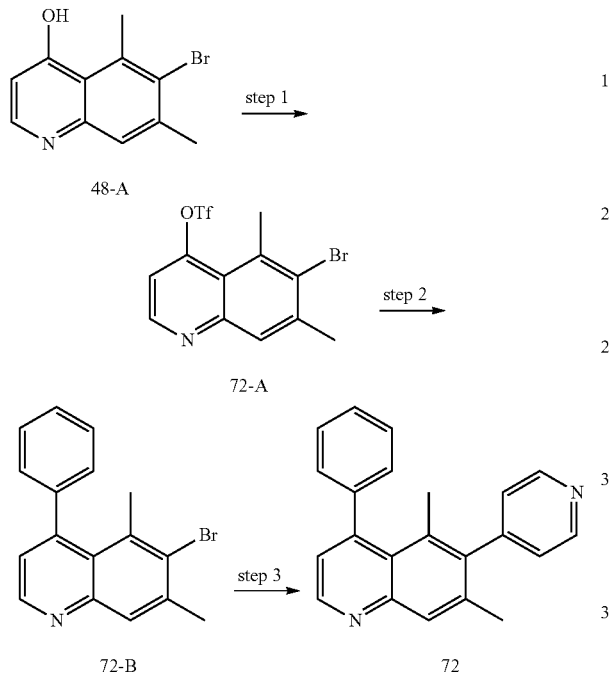

Step 1: To a solution of 48-A (300 mg, 1.19 mmol) in DCM (6 mL) was added Et₃N (0.69 mL, 4.76 mmol) followed by Tf₂O (0.40 mL, 2.38 mmol), and the reaction mixture was stirred for overnight at rt. After completion, the mixture was filtered through a short pad of silica gel to yield 72-A: 400 mg, 87% yield. LCMS (M+H)⁺:384.54.

Step 2: The solution of 72-A (400 mg, 1.04 mmol), phenylboronic acid (190 mg, 1.56 mmol) and Et₃N (0.60 mL, 4.16 mmol) was degassed with nitrogen for 5 min before Pd(PPh₃)₄ (241 mg, 0.21 mmol) was added. The reaction mixture was heated to 100° C. and stirred for 5 h. After completion, the mixture was directly purified by column (silica gel) to yield 72-B: 170 mg, 52% yield. LCMS (M+H)⁺:314.14.

Step 3: The solution of 72-B (22 mg, 0.07 mmol), 4-pyridylboronic acid (17 mg, 0.14 mmol), and Na₂CO₃ (30 mg, 0.28 mmol) was degassed with nitrogen for 5 min before XPhos-Pd-G3 (12 mg, 0.014 mmol) was added. The reaction mixture was heated to 90° C. and stirred for 2 h. After completion, the mixture was purified by column (silica gel) to yield 72: 11 mg, 50% yield. ¹H NMR (300 MHz, Chloroform-d) δ 8.88 (d, J=4.3 Hz, 1H), 8.73-8.65 (m, 2H), 8.00 (s, 1H), 7.45-7.38 (m, 3H), 7.34 (dq, J=7.9, 3.1, 2.5 Hz, 2H), 7.24 (d, J=4.3 Hz, 1H), 7.17-7.06 (m, 2H), 2.19 (d, J=1.0 Hz, 3H), 1.69 (s, 3H). LCMS (M+H)⁺:311.02.

73

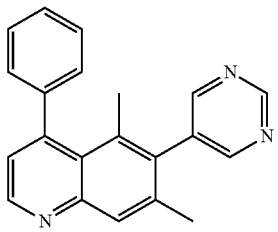

¹H NMR (300 MHz, Chloroform-d) δ 9.26 (s, 1H), 8.91 (d, J=4.4 Hz, 1H), 8.62 (s, 2H), 8.04 (d, J=1.3 Hz, 1H), 7.46-7.39 (m, 3H), 7.39-7.32 (m, 2H), 7.27 (s, 1H), 2.23 (d, J=1.0 Hz, 3H), 1.72 (s, 3H). LCMS (M+H)⁺:312.00.

74

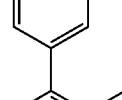

¹H NMR (300 MHz, Chloroform-d) δ 8.88 (d, J=4.4 Hz, 1H), 8.00 (s, 1H), 7.96 (s, 1H), 7.44 (dd, J=5.2, 1.9 Hz, 3H), 7.34 (dt, J=6.8, 2.3 Hz, 2H), 7.23 (d, J=4.3 Hz, 1H), 7.08 (s, 1H), 2.35 (d, J=1.0 Hz, 3H), 1.83 (s, 3H).
LCMS (M+H)⁺:300.76.

75

¹H NMR (300 MHz, Chloroform-d) δ 8.82 (d, J=4.4 Hz, 1H), 7.93 (s, 1H), 7.43-7.31 (m, 6H), 7.18 (d, J=4.3 Hz, 1H), 6.12 (d, J=2.1 Hz, 1H), 3.95 (s, 3H), 2.29 (d, J=1.0 Hz, 3H), 1.79 (s, 3H).

76

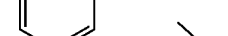

¹H NMR (300 MHz, Chloroform-d) δ 8.90 (d, J=4.4 Hz, 1H), 8.00 (s, 1H), 7.60-7.53 (m, 1H), 7.44 (dd, J=5.1, 1.8 Hz, 3H), 7.37-7.30 (m, 2H), 7.25 (d, J=4.3 Hz, 1H), 6.17 (d, J=1.9 Hz, 1H), 3.55 (s, 3H), 2.23 (d, J=1.0 Hz, 3H), 1.71 (s 3H).

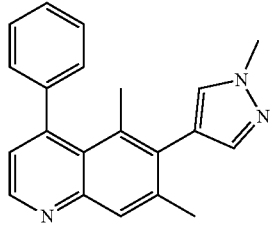

77

¹H NMR (300 MHz, Chloroform-d) δ 8.82 (d, J=4.4 Hz, 1H), 7.96 (s, 1H), 7.47-7.40 (m, 3H), 7.39-7.31 (m, 3H), 7.26 (m, 1H), 7.24-7.18 (m, 1H), 3.98 (s, 3H), 2.32 (d, J=1.0 Hz, 3H), 1.82 (s, 3H).

Example 12

Preparation of Compounds 78-86

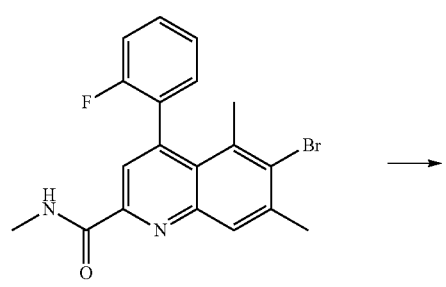

78-A

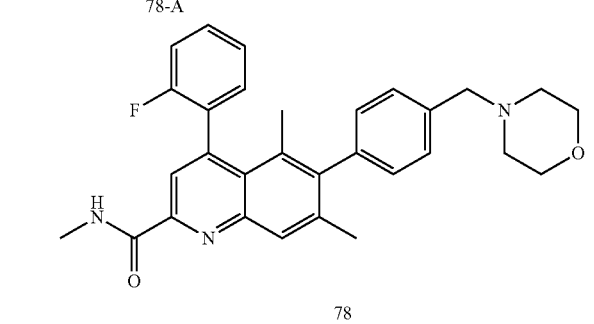

78

The solution of 78-A (17 mg, 0.044 mmol) and (4-(morpholinomethyl)phenyl)boronic acid pinacol ester (19 mg, 0.088 mmol), Na₂CO₃ (19 mg, 0.176 mmol) in dioxane (2 mL) and H₂O (0.2 mL) was degassed with nitrogen for 5 min before XPhos-Pd-G3 (4 mg, 0.004 mmol) was added. The reaction mixture was heated to 80° C. and stirred overnight. The mixture was directly purified by column (silica gel) to yield 78: 4.5 mg, 21% yield. 1H NMR (400 MHz, Chloroform-d) δ 8.26 (q, J=5.1 Hz, 1H), 8.09 (s, 1H), 7.94 (s, 1H), 7.36 (dtd, J=19.4, 7.5, 6.7, 2.7 Hz, 4H), 7.24-7.02 (m, 4H), 3.80-3.65 (m, 4H), 3.54 (s, 2H), 3.12 (d, J=5.1 Hz, 3H), 2.47 (dd, J=5.8, 3.4 Hz, 4H), 2.19 (d, J=0.9 Hz, 3H), 1.78 (s, 3H). LCMS (M+H)⁺: 484.52.

Compounds 79-85 were Prepared Similar to the Compound 78.

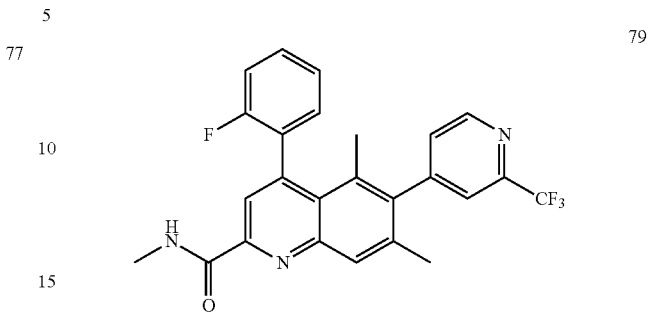

79

55% yield. 1H NMR (400 MHz, Chloroform-d) δ 8.82 (t, J=5.5 Hz, 1H), 8.24 (d, J=6.2 Hz, 1H), 8.14 (s, 1H), 8.00 (s, 1H), 7.53 (d, J=25.1 Hz, 1H), 7.46-7.29 (m, 3H), 7.26-7.19 (m, 1H), 7.19-7.07 (m, 1H), 3.13 (d, J=5.1 Hz, 3H), 2.17 (s, 3H), 1.78 (s, 3H). LCMS (M+H)⁺: 454.46.

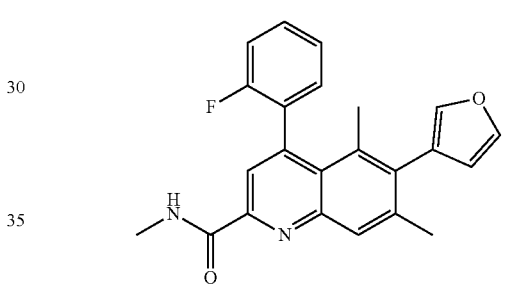

80

40% yield. 1H NMR (400 MHz, Chloroform-d) δ 8.35-8.17 (m, 1H), 8.08 (s, 1H), 7.93 (s, 1H), 7.54 (t, J=1.7 Hz, 1H), 7.44-7.29 (m, 3H), 7.25-7.07 (m, 2H), 6.31 (dd, J=1.7, 0.9 Hz, 1H), 3.11 (d, J=5.1 Hz, 3H), 2.33 (d, J=1.0 Hz, 3H), 1.94 (s, 3H). LCMS (M+H)⁺: 375.35.

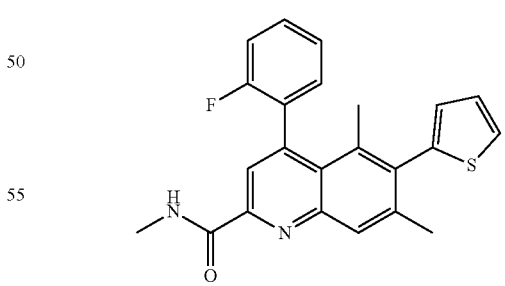

81

48% yield. 1H NMR (400 MHz, Chloroform-d) δ 8.39-8.16 (m, 1H), 8.09 (s, 1H), 7.94 (s, 1H), 7.48-7.30 (m, 3H), 7.22 (td, J=7.5, 1.1 Hz, 1H), 7.15-7.08 (m, 2H), 6.84 (dd, J=3.4, 1.2 Hz, 1H), 3.12 (d, J=5.1 Hz, 3H), 2.32 (s, 3H), 1.92 (s, 3H). LCMS (M+H)⁺: 391.36.

82

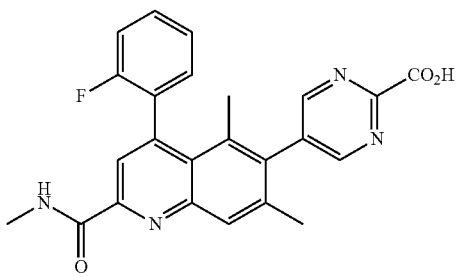

5% yield. 1H NMR (400 MHz, Methanol-d4) δ 8.70 (s, 2H), 8.12 (s, 1H), 7.96 (s, 1H), 7.51 (td, J=7.9, 4.0 Hz, 1H), 7.48-7.37 (m, 1H), 7.37-7.27 (m, 1H), 7.23 (t, J=9.1 Hz, 1H), 3.06 (s, 3H), 2.21 (s, 3H), 1.80 (s, 3H). LCMS (M+H)+: 431.45.

83

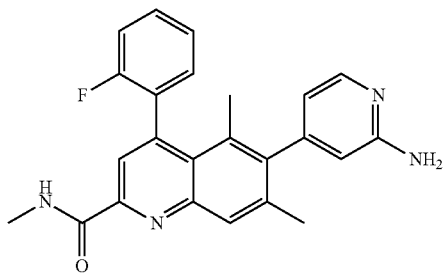

42% yield. 1H NMR (400 MHz, Chloroform-d) δ 8.25 (q, J=4.9, 4.1 Hz, 1H), 8.17-8.07 (m, 2H), 7.93 (s, 1H), 7.50-7.28 (m, 2H), 7.25-7.06 (m, 2H), 6.46 (ddd, J=26.0, 5.2, 1.4 Hz, 1H), 6.30 (d, J=25.4 Hz, 1H), 4.57 (d, J=9.2 Hz, 2H), 3.11 (d, J=5.1 Hz, 3H), 2.23 (s, 3H), 1.83 (d, J=1.6 Hz, 3H). LCMS (M+H)+: 401.44.

84

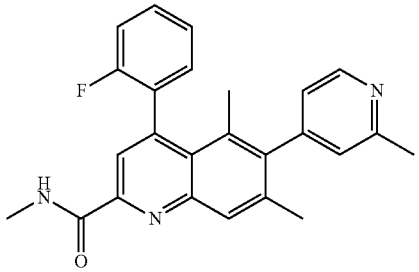

1H NMR (400 MHz, CDCl3): δ 8.57 (t, J=5.6 Hz, 1H), 8.55 (s, 1H), 8.10 (s, 1H), 7.95 (s, 1H), 7.41-7.33 (m, 2H), 7.26-7.22 (m, 1H), 7.11 (t, J=8.8 Hz, 1H), 7.00-6.88 (m, 2H), 3.11 (d, J=4.8 Hz, 3H), 2.59 (d, J=5.6 Hz, 3H), 2.17 (s, 3H), 1.64 (s, 3H). LCMS (M+H)+: 400.10.

85

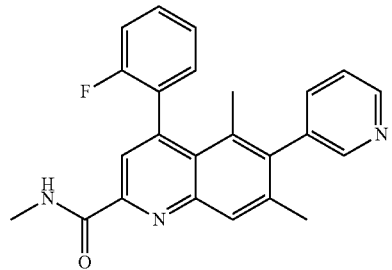

1H NMR (400 MHz, CDCl3): δ 8.71 (t, J=6.0 Hz, 1H), 8.45 (d, J=12.0 Hz, 1H), 8.24 (s, 1H), 8.18 (s, 1H), 7.93 (s, 1H), 7.53-7.43 (m, 1H), 7.39-7.32 (m, 3H), 7.23-7.18 (m, 1H), 7.12-7.08 (m, 1H), 3.10 (d, J=4.8 Hz, 3H), 2.17 (s, 3H), 1.78 (s, 3H). LCMS (M+H)+: 386.20.

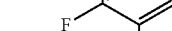

86

Step 1: The solution of 78-A (376 mg, 0.97 mmol) and tert-butyl 4-(4,4,5,5-tetramethyl-1,3,2-dioxaborolan-2-yl)-5,6-dihydropyridine-1(2H)-carboxylate (390 mg, 1.26 mmol), Na2CO3 (412 mg, 3.88 mmol) in dioxane (8 mL) and H2O (0.9 mL) was degassed with nitrogen for 5 min before XPhos-Pd-G3 (41 mg, 0.049 mmol) was added. The reaction mixture was heated to 70° C. and stirred overnight. The mixture was directly purified by column (silica gel) to yield 86-A: 450 mg, 94% yield. LCMS (M+H)+: 490.54.

Step 2: The solution of 86-A (450 mg, 0.92 mmol) and TFA (3.52 mL, 46 mmol) in DCM (3.5 mL) was stirred overnight at rt, and the solvent was removed under vacuum, and the residue was purified by column (silica gel with Et3N) to yield 86: 358 mg, 100% yield. 1H NMR (400 MHz, Chloroform-d) δ 8.22 (q, J=5.0 Hz, 1H), 8.07 (d, J=1.0 Hz, 1H), 7.90 (s, 1H), 7.46-7.38 (m, 1H), 7.31 (qd, J=7.6, 1.9 Hz, 1H), 7.26-7.20 (m, 1H), 7.12 (dddd, J=9.5, 8.3, 4.3, 1.1 Hz, 1H), 5.57 (ddt, J=26.9, 3.6, 1.7 Hz, 1H), 3.82 (dtt, J=12.1, 9.1, 6.1 Hz, 2H), 3.53-3.27 (m, 2H), 3.10 (d, J=5.0 Hz, 3H), 2.69-2.46 (m, 2H), 2.44 (s, 3H), 2.01 (d, J=6.5 Hz, 3H). LCMS (M+H)+: 390.52.

Example 13

Preparation of Compound 87

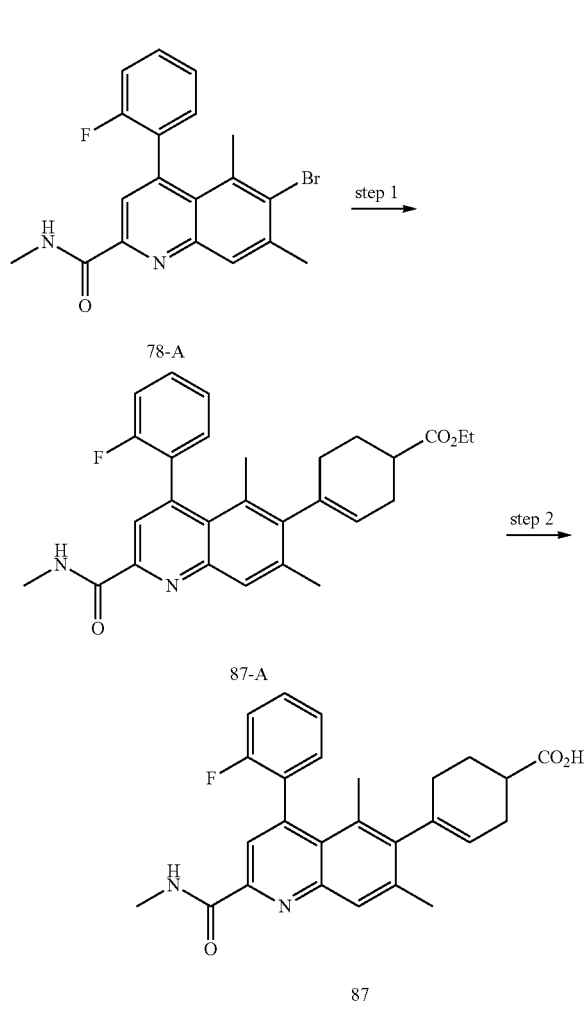

Step 1: The solution of 78-A (314 mg, 0.81 mmol) and ethyl 4-(4,4,5,5-tetramethyl-1,3,2-dioxaborolan-2-yl)cyclohex-3-enecarboxylate (250 mg, 0.89 mmol), $Na_2CO_3$ (344 mg, 3.884 mmol) in dioxane (7 mL) and $H_2O$ (0.8 mL) was degassed with nitrogen for 5 min before XPhos-Pd-G3 (41 mg, 0.049 mmol) was added. The reaction mixture was heated to 70° C. and stirred for 2 h. The mixture was directly purified by column (silica gel) to yield 87-A: 350 mg, 94% yield. LCMS $(M+H)^+$: 461.51.

Step 2: The solution of 87-A (160 mg, 0.35 mmol) in THF (2.5 mL) was added LiOH (1.04 mL, 1M, 1.04 mmol), and the mixture was stirred overnight at rt. The reaction mixture was then acidified with 1M HCl to pH=3, and extracted with DCM. The combined extracts were washed with $H_2O$, dried over $Na_2SO_4$, filtered, and concentrated. The residue was purified by column to yield 87: 88 mg, 59% yield. 1H NMR (400 MHz, Chloroform-d) δ 8.25 (q, J=5.1 Hz, 1H), 8.04 (t, J=1.8 Hz, 1H), 7.87 (s, 1H), 7.41 (ttd, J=7.3, 5.1, 1.8 Hz, 1H), 7.36-7.27 (m, 1H), 7.25-7.18 (m, 1H), 7.12 (dtd, J=9.4, 6.8, 3.2 Hz, 1H), 5.53 (dt, J=26.2, 3.0 Hz, 1H), 3.10 (d, J=5.1 Hz, 3H), 2.74 (ddtd, J=21.2, 8.5, 5.9, 2.8 Hz, 1H), 2.61-2.45 (m, 2H), 2.42 (d, J=19.0 Hz, 3H), 2.34-2.06 (m, 3H), 2.00 (dd, J=18.0, 6.7 Hz, 3H), 1.95-1.81 (m, 1H). LCMS $(M+H)^+$: 433.55.

Example 14

Preparation of Compound 88

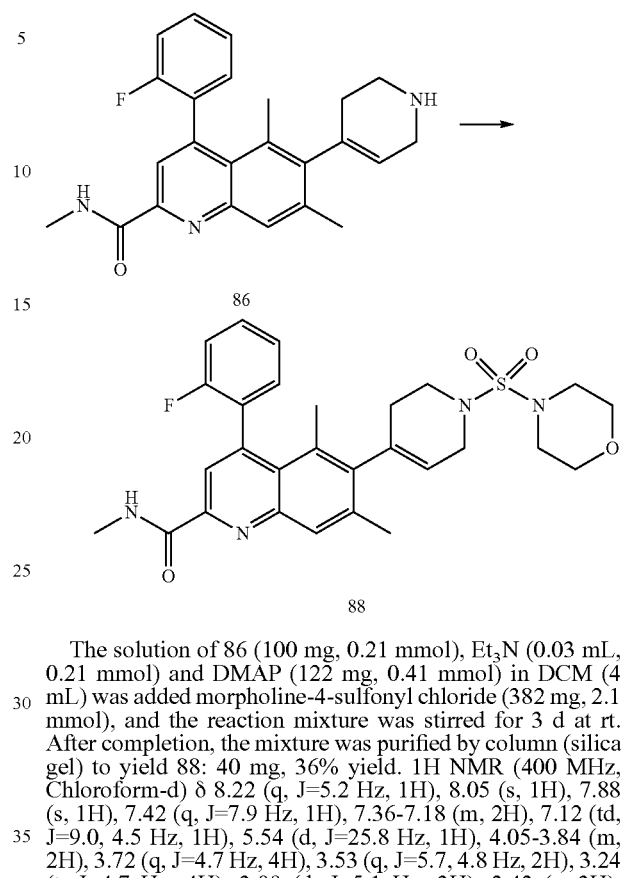

The solution of 86 (100 mg, 0.21 mmol), $Et_3N$ (0.03 mL, 0.21 mmol) and DMAP (122 mg, 0.41 mmol) in DCM (4 mL) was added morpholine-4-sulfonyl chloride (382 mg, 2.1 mmol), and the reaction mixture was stirred for 3 d at rt. After completion, the mixture was purified by column (silica gel) to yield 88: 40 mg, 36% yield. 1H NMR (400 MHz, Chloroform-d) δ 8.22 (q, J=5.2 Hz, 1H), 8.05 (s, 1H), 7.88 (s, 1H), 7.42 (q, J=7.9 Hz, 1H), 7.36-7.18 (m, 2H), 7.12 (td, J=9.0, 4.5 Hz, 1H), 5.54 (d, J=25.8 Hz, 1H), 4.05-3.84 (m, 2H), 3.72 (q, J=4.7 Hz, 4H), 3.53 (q, J=5.7, 4.8 Hz, 2H), 3.24 (t, J=4.7 Hz, 4H), 3.09 (d, J=5.1 Hz, 3H), 2.42 (s, 3H), 2.38-2.19 (m, 2H), 2.01 (d, J=6.0 Hz, 3H). LCMS $(M+H)^+$: 539.55.

Example 15

Preparation of Compound 89

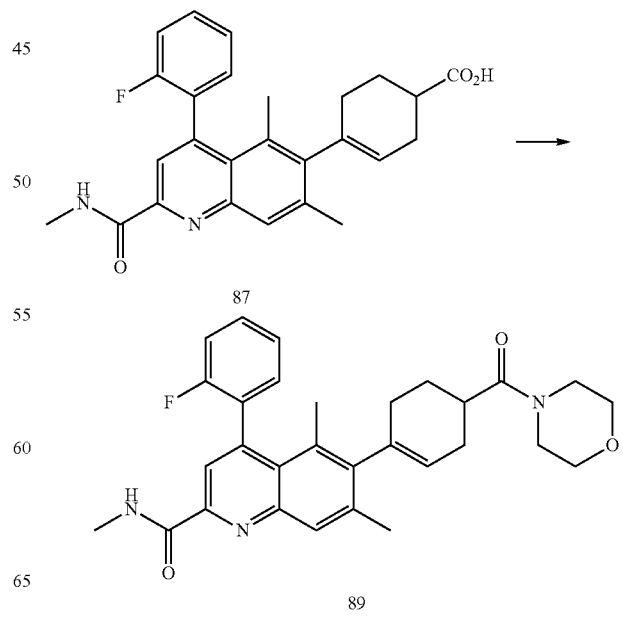

The solution of 87 (25 mg, 0.058 mmol) in DCM (2 mL) was added EDCI (17 mg, 0.087 mmol), DMAP (7 mg, 0.058 mmol) and morpholine (15 mg, 0.17 mmol), and the mixture was stirred overnight at rt. After completion, the mixture was directly purified by column (silica gel) to yield 89: 20 mg, 69% yield. 1H NMR (400 MHz, Chloroform-d) δ 8.25 (p, J=5.4 Hz, 1H), 8.06 (s, 1H), 7.89 (d, J=6.4 Hz, 1H), 7.43 (ddt, J=8.6, 6.1, 3.0 Hz, 1H), 7.33 (dq, J=12.3, 7.1, 6.3 Hz, 1H), 7.24 (td, J=7.3, 3.7 Hz, 1H), 7.14 (td, J=8.6, 4.1 Hz, 1H), 5.62-5.50 (m, 1H), 3.69 (d, J=5.2 Hz, 6H), 3.64-3.52 (m, 2H), 3.11 (d, J=5.0 Hz, 3H), 2.83 (dtt, J=20.7, 8.6, 4.3 Hz, 1H), 2.66-2.50 (m, 1H), 2.45 (d, J=19.6 Hz, 3H), 2.37-2.13 (m, 3H), 2.11-1.99 (m, 3H), 1.94 (tt, J=14.2, 5.0 Hz, 2H). LCMS (M+H)+: 502.58.

Example 16

Preparation of Compound 90

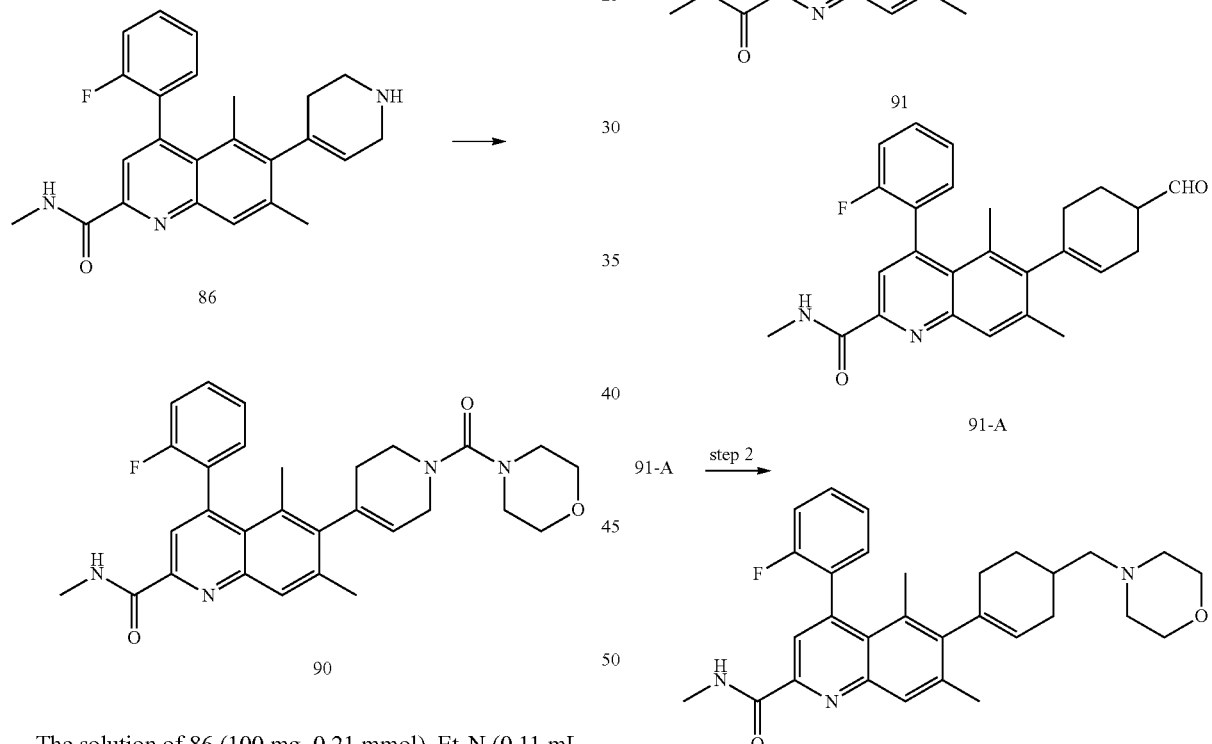

The solution of 86 (100 mg, 0.21 mmol), Et$_3$N (0.11 mL, 0.82 mmol) and morpholine-4-carbonyl chloride (307 mg, 2.1 mmol) in DCM (3 mL) was stirred overnight at rt. After completion, the mixture was purified by column (silica gel) to yield 90: 42 mg, 41% yield. 1H NMR (400 MHz, Chloroform-d) δ 8.25 (q, J=5.2 Hz, 1H), 8.06 (s, 1H), 7.89 (s, 1H), 7.42 (q, J=7.2 Hz, 1H), 7.37-7.27 (m, 1H), 7.23 (dt, J=7.6, 3.8 Hz, 1H), 7.13 (td, J=9.0, 3.6 Hz, 1H), 5.52 (d, J=22.2 Hz, 1H), 3.95 (d, J=6.9 Hz, 2H), 3.77-3.66 (m, 4H), 3.50 (q, J=4.6, 3.8 Hz, 2H), 3.28 (q, J=5.1 Hz, 4H), 3.10 (d, J=5.1 Hz, 3H), 2.43 (s, 3H), 2.28 (q, J=16.3, 11.2 Hz, 2H), 2.02 (d, J=6.8 Hz, 3H). LCMS (M+H)+: 503.56.

Example 17

Preparation of Compounds 91, 92

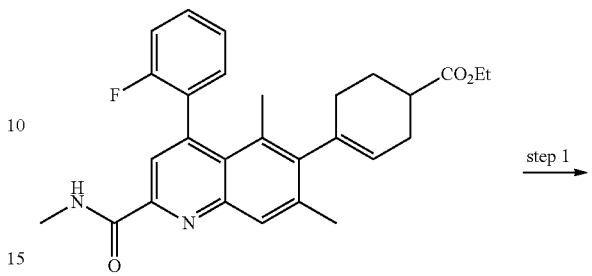

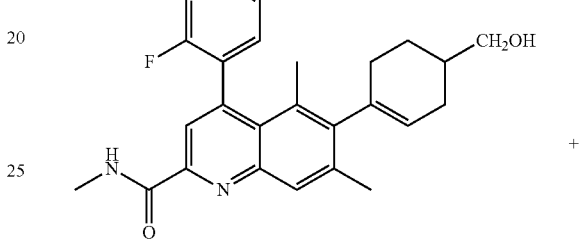

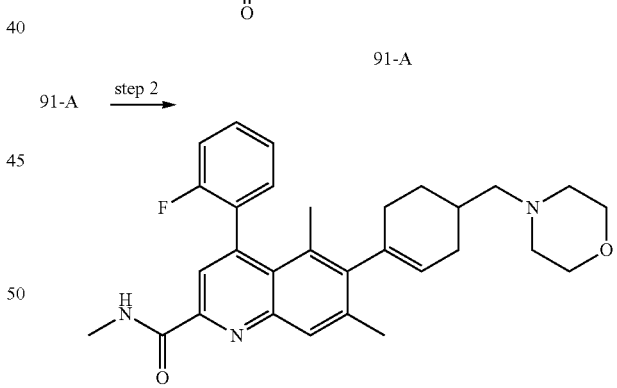

Step 1: The solution of 87-A (150 mg, 0.33 mmol) in DCM (10 mL) was added DIBAL-H (0.087 mL, 0.49 mmol) at −78° C. dropwisely, and the mixture was stirred for 2 h at −78° C. before it was quenched with MeOH. Saturated NH$_4$Cl solution was added, and the mixture was warmed to rt, and stirred for 30 min. The separated organic layer was then dried over Na$_2$SO$_4$, filtered, and concentrated. The residue was then purified by column (silica gel) to yield a mixture of two products: 91 (16 mg, 12% yield) and 91-A (60 mg, 44% yield).

Data for 91: 1H NMR (400 MHz, Chloroform-d) δ 8.24 (q, J=5.4 Hz, 1H), 8.03 (s, 1H), 7.86 (s, 1H), 7.40 (tdd, J=7.4, 5.1, 1.9 Hz, 1H), 7.36-7.27 (m, 1H), 7.22 (tdd, J=6.1, 3.6, 1.7 Hz, 1H), 7.12 (td, J=9.0, 4.1 Hz, 1H), 5.50 (ddd, J=24.8, 4.3, 2.2 Hz, 1H), 3.61 (dtt, J=9.7, 6.3, 3.9 Hz, 2H), 3.09 (d, J=5.1 Hz, 3H), 2.42 (d, J=16.8 Hz, 3H), 2.38-2.06 (m, 2H), 2.04-1.95 (m, 3H), 1.95-1.80 (m, 2H), 1.80-1.32 (m, 3H). LCMS (M+H)$^+$: 419.50.

Step 2: The solution of 91-A (35 mg, 0.084 mmol) and morpholine (8 mg, 0.092 mmol) in DCM (3 mL) was stirred for 30 min before NaBH(OAc)$_3$ (36 mg, 0.17 mmol) was added. The reaction mixture was stirred for 2 h at rt before it was quenched with 0.5 mL H$_2$O. The mixture was then purified by column (silica gel) to yield 92: 32 mg, 78% yield. 1H NMR (400 MHz, Chloroform-d) δ 8.25 (q, J=5.1 Hz, 1H), 8.03 (t, J=1.4 Hz, 1H), 7.85 (s, 1H), 7.40 (dtt, J=8.2, 5.0, 2.8 Hz, 1H), 7.35-7.27 (m, 1H), 7.21 (tt, J=7.6, 3.4 Hz, 1H), 7.12 (tt, J=8.3, 3.9 Hz, 1H), 5.48 (ddd, J=25.0, 4.6, 2.3 Hz, 1H), 3.72 (q, J=4.5 Hz, 4H), 3.09 (d, J=5.1 Hz, 3H), 2.47 (q, J=4.6 Hz, 4H), 2.42 (d, J=16.2 Hz, 3H), 2.37-2.25 (m, 3H), 2.25-2.05 (m, 1H), 2.05-1.96 (m, 4H), 1.96-1.75 (m, 3H), 1.47-1.33 (m, 1H). LCMS (M+H)$^+$: 488.67.

Example 18

Preparation of Compound 93

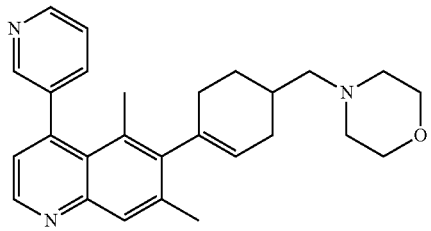

93

Compound 93 was prepared using method similar to compound 48 in Example 9. 1H NMR (400 MHz, Chloroform-d) δ 8.90 (d, J=4.3 Hz, 1H), 8.68-8.62 (m, 2H), 8.00 (s, 1H), 7.74-7.67 (m, 1H), 7.43-7.37 (m, 3H), 7.20 (d, J=4.3 Hz, 1H), 7.10 (dd, J=7.2, 5.0 Hz, 2H), 3.75 (t, J=4.7 Hz, 4H), 3.57 (s, 2H), 2.54-2.44 (m, 4H), 2.22 (d, J=1.0 Hz, 3H), 1.70 (s, 3H). LCMS (M+H)$^+$: 410.42.

Example 19

Preparation of Compounds 94-98

Compounds 94-98 were prepared using method similar to compound 13 in example 1.

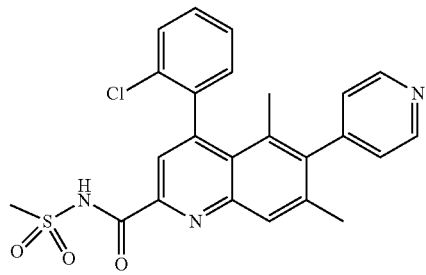 [SMILES: Cc1cc2nc(C(=O)NS(C)(=O)=O)cc(-c3ccccc3Cl)c2c(C)c1-c1ccncc1]

94

1H NMR (300 MHz, Methanol-d4) δ 8.70 (dd, J=5.8, 3.2 Hz, 2H), 8.19 (s, 1H), 7.91 (s, 1H), 7.61-7.33 (m, 6H), 3.43 (s, 3H), 2.22 (d, J=1.0 Hz, 3H), 1.76 (s, 3H). LCMS (M+H)$^+$: 466.22.

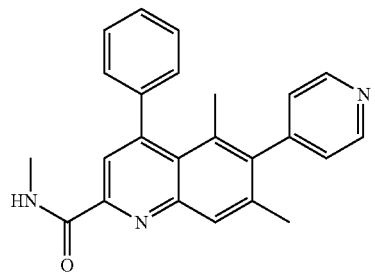 [SMILES: CNC(=O)c1cc(-c2ccccc2)c2c(C)c(-c3ccncc3)c(C)cc2n1]

95

1H NMR (400 MHz, Chloroform-d) δ 8.76-8.68 (m, 2H), 8.28 (d, J=5.0 Hz, 1H), 8.14 (s, 1H), 8.01-7.95 (m, 1H), 7.46-7.38 (m, 3H), 7.38-7.32 (m, 2H), 7.17-7.12 (m, 2H), 3.14 (d, J=5.1 Hz, 3H), 2.20 (d, J=1.0 Hz, 3H), 1.88 (s, 1H), 1.72 (s, 3H). LCMS (M+H)$^+$: 368.35.

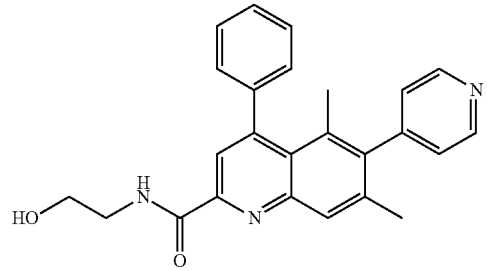 [SMILES: Cc1cc2nc(C(=O)NCCO)cc(-c3ccccc3)c2c(C)c1-c1ccncc1]

96

1H NMR (400 MHz, Chloroform-d) δ 8.75-8.70 (m, 2H), 8.68 (t, J=6.0 Hz, 1H), 8.13 (s, 1H), 8.04-7.97 (m, 1H), 7.47-7.37 (m, 3H), 7.37-7.30 (m, 2H), 7.18-7.07 (m, 2H), 3.95 (dd, J=5.6, 4.4 Hz, 2H), 3.76 (td, J=5.7, 4.3 Hz, 2H), 2.20 (d, J=1.0 Hz, 3H), 1.88 (s, 1H), 1.72 (s, 3H). LCMS (M+H)$^+$: 398.36.

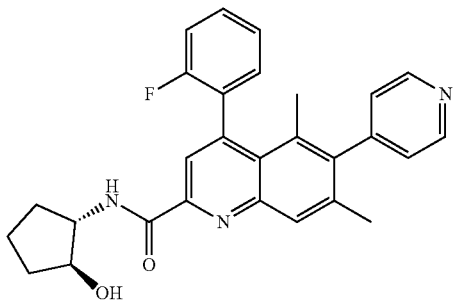 [SMILES: Cc1cc2nc(C(=O)N[C@H]3CCC[C@@H]3O)cc(-c3ccccc3F)c2c(C)c1-c1ccncc1]

97

1H NMR (400 MHz, Chloroform-d) δ 8.72 (t, J=5.6 Hz, 2H), 8.37 (d, J=4.8 Hz, 1H), 8.12 (s, 1H), 8.04-8.00 (m, 1H), 7.43 (dddd, J=8.3, 7.2, 5.2, 1.9 Hz, 1H), 7.36 (tt, J=7.5, 1.6 Hz, 1H), 7.25 (td, J=7.5, 1.1 Hz, 1H), 7.18 (dt, J=6.5, 1.9 Hz, 1H), 7.15-7.09 (m, 2H), 4.58-4.44 (m, 1H), 4.23 (q, J=6.7 Hz, 1H), 4.13 (ddd, J=9.6, 5.3, 2.4 Hz, 1H), 2.36 (dq, J=8.0, 4.0 Hz, 1H), 2.21 (d, J=1.0 Hz, 3H), 2.18-2.08 (m, 1H), 2.01-1.83 (m, 2H), 1.82 (m, 4H). LCMS (M+H)$^+$: 456.47.

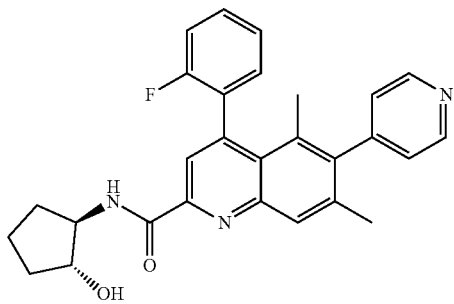 [SMILES: Cc1cc2nc(C(=O)N[C@@H]3CCC[C@H]3O)cc(-c3ccccc3F)c2c(C)c1-c1ccncc1]

98

1H NMR (400 MHz, Chloroform-d) δ 8.72 (t, J=5.5 Hz, 2H), 8.38 (d, J=4.8 Hz, 1H), 8.12 (s, 1H), 8.02 (d, J=1.1 Hz, 1H), 7.49-7.33 (m, 2H), 7.25 (td, J=7.5, 1.1 Hz, 1H), 7.20-7.06 (m, 3H), 4.51 (s, 1H), 4.23 (d, J=6.7 Hz, 1H), 4.16-4.04 (m, 1H), 2.37 (d, J=7.9 Hz, 1H), 2.21 (d, J=1.0 Hz, 3H), 2.18-2.10 (m, 1H), 2.00-1.85 (m, 2H), 1.85-1.79 (m, 4H). LCMS (M+H)⁺: 456.47.

Example 20

Preparation of Compounds 99-102

Compounds 99-106 were prepared using method similar to compound 69 in example 10.

99

[Structure of compound 99]

$^1$H NMR (400 MHz, CD$_3$OD): δ 8.69 (d, J=5.6 Hz, 2H), 8.26-8.25 (m, 1H), 8.01 (s, 1H), 7.88 (s, 1H), 7.35 (s, 2H), 5.78 (s, 1H), 4.58 (s, 2H), 4.31 (s, 2H), 4.00-3.93 (m, 2H), 3.03 (s, 3H), 2.43 (s, 3H), 2.18 (s, 3H). LCMS (M+H)⁺: 374.10

100

[Structure of compound 100]

$^1$H NMR (400 MHz, CDCl$_3$): δ 8.75-8.72 (m, 2H), 8.23 (s, 1H), 7.78 (d, J=5.2 Hz, 1H), 7.16-7.14 (m, 2H), 3.39 (d, J=12.4 Hz, 2H), 3.08 (d, J=3.2 Hz, 3H), 3.04-2.99 (m, 2H), 2.86 (d, J=11.6 Hz, 2H), 2.55 (s, 3H), 2.42 (t, J=11.2 Hz, 2H), 2.36 (s, 3H), 2.12 (s, 3H). LCMS (M+H)⁺: 390.25.

101

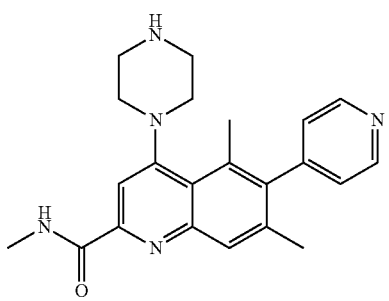 [SMILES: CNC(=O)c1cc(N2CCNCC2)c2c(C)c(-c3ccncc3)c(C)cc2n1]

$^1$H NMR (400 MHz, CD$_3$OD): δ 9.06 (d, J=6.0 Hz, 2H), 8.20 (d, 6.0 Hz, 2H), 8.07 (s, 1H), 7.95 (s, 1H), 4.07-3.95 (m, 4H), 3.48-3.45 (m, 4H), 3.07 (s, 3H), 2.46 (s, 3H), 2.26 (s, 3H). LCMS (M+H)⁺: 376.20.

102

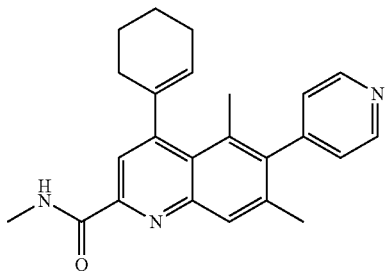 [SMILES: CNC(=O)c1cc(C2=CCCCC2)c2c(C)c(-c3ccncc3)c(C)cc2n1]

$^1$H NMR (400 MHz, CD$_3$OD): δ 8.67 (d, J=5.2 Hz, 2H), 7.97 (s, 1H), 7.82 (s, 1H), 7.32 (t, J=6.0 Hz, 1H), 5.67 (s, 1H), 3.03 (s, 3H), 2.40 (s, 3H), 2.35-2.16 (m, 4H), 2.15 (s, 3H), 1.73-1.68 (m, 4H). LCMS (M+H)⁺: 372.15.

Example 21

Preparation of Compound 103

[Structure of compound 103-A] →

103-A

-continued

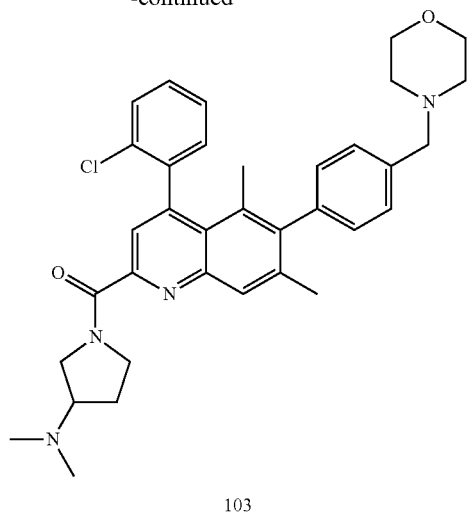

103

To a solution of compound 103-A (530 mg, 1.06 mmol), prepared using a similar method as described for compound 48-C in example 9, in methanol (5 mL) was added 1M NaOH solution (4 mL) and the mixture was stirred for 16 h at rt. The mixture was acidified to pH 3 with 1N HCl and extracted with $CH_2Cl_2$. The combined extracts were dried ($Na_2SO_4$), filtered, and concentrated to give the desired acid which was used for the next step without further purification (362 mg, 70% yield). LCMS (M+H)$^+$: 487.29. To a solution of the acid obtained above (24 mg, 0.049 mmol) and N,N-dimethylpyrrolidin-3-amine (11 mg, 0.098) was added BOP (33 mg, 0.074 mmol) and DIEA (26 µL, 0.15 mmol) and the mixture was stirred overnight. After evaporation of the solvent in vacuo, the crude residue was taken up in $CH_2Cl_2$ and washed with 1N—NaOH, and purified by a preparative LC/MS to afford 103: 21 mg, 74% yield. $^1$H NMR (400 MHz, Chloroform-d) δ 7.79 (s, 1H), 7.71 (d, J=3.6 Hz, 1H), 7.45-7.33 (m, 6H), 7.11 (m, 2H), 4.31 (t, J=11.8 Hz, 1H), 4.01 (t, J=11.4 Hz, 1H), 3.75 (br s, 4H), 3.57 (s, 2H), 3.31 (td, J=7.8, 1.84 Hz, 1H), 3.12 (t, J=7.4 Hz, 1H), 2.91 (m, 1H), 2.50 (s, 4H), 2.40 (br s, 6H), 2.21 (s, 3H), 1.74 (s, 3H), 1.44 (t, J=7.36 Hz, 1H), 1.16 (t, J=7.28 Hz, 1H). LCMS (M+H)$^+$: 583.35.

Preparation of Compound 104-106

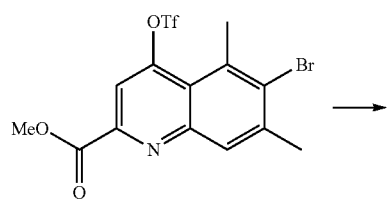

To a mixture of methyl 6-bromo-5,7-dimethyl-4-(trifluoromethylsulfonyloxy)quinoline-2-carboxylate (600 mg, 1.36 mmol), (2-methylpyrazol-3-yl)boronic acid (342 mg, 2.72 mmol), triethylamine (550 mg, 5.44 mmol) in dioxane (15 mL) was added Pd(PPh$_3$)$_4$ (157 mg, 136 µmol) under nitrogen atmosphere. The reaction mixture was stirred at 100° C. for 12 hrs. On completion, the reaction mixture was concentrated in vacuo to give the residue. The residue was purified by silica gel chromatography (petroleum ether:ethyl acetate=10:1) to give 104-A (280 mg, 53% yield) as white solid. LCMS (M+1)$^+$=374.0, 376.0.

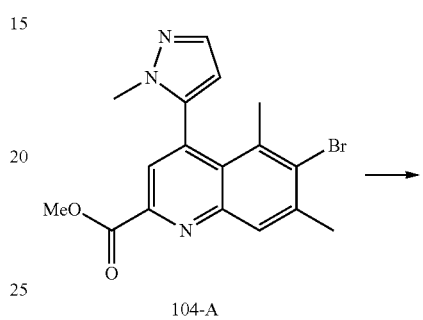

104-A

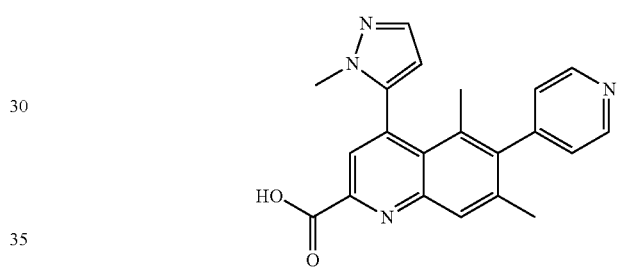

104-B

To a mixture of methyl 6-bromo-5,7-dimethyl-4-(2-methylpyrazol-3-yl)quinoline-2-carboxylate (350 mg, 935 µmol), 4-pyridylboronic acid (172 mg, 1.40 mmol) and sodium carbonate (198. mg, 1.87 mmol) in a mixture solvent of dioxane (40 mL) and water (4 mL) was added Xphos-Pd-G2 (73.3 mg, 93.5 µmol). The reaction mixture was stirred at 90° C. for 16 hrs under nitrogen atmosphere. On completion, the reaction mixture was acidified with 1N HCl solution to pH=5 and concentrated in vacuo to give 104-B (300 mg, 75% yield) as light yellow solid and the crude product was for the next step directly without any purification. LCMS (M+1)$^+$=359.1.

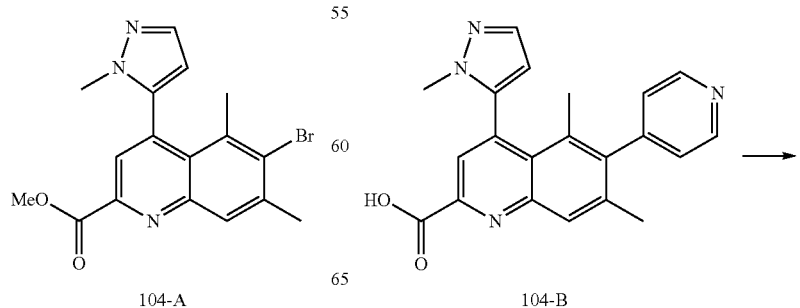

104-A                    104-B

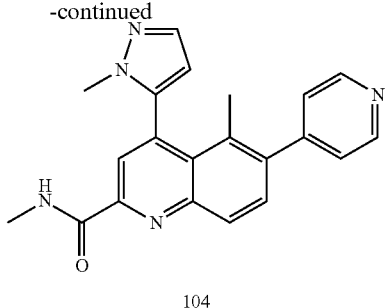

104

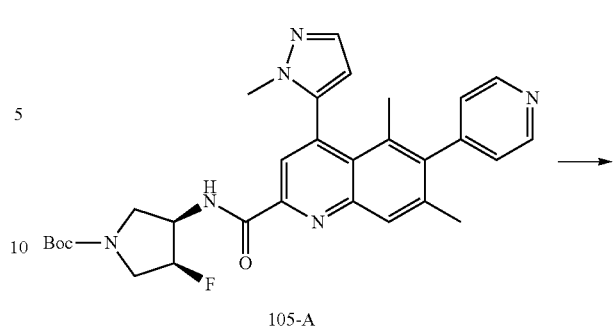

105-A

To a mixture of 5,7-dimethyl-4-(2-methylpyrazol-3-yl)-6-(4-pyridyl)quinoline-2-carboxylic acid (80.0 mg, 223 µmol), methylamine (46.4 mg, 446 µmol, HCl salt), HATU (169 mg, 446 mol) in DMF (5 mL) was added diisopropylethylamine (144 mg, 1.12 mmol). The reaction mixture was stirred at 20° C. for 16 hrs. On completion, the reaction mixture was concentrated in vacuo. The residue was purified by prep-HPLC (column: Phenomenex Synergi C18 150*25*10 µm; mobile phase: [water (0.05% HCl)-ACN]) to give 104 (42.0 mg, 40% yield, HCl salt) as yellow solid. LCMS (M+1)$^+$=372.0. 1H NMR (400 MHz, DMSO-d6) δ=9.07 (dd, J=5.6, 5.6 Hz, 2H), 9.04 (q, J=4.8 Hz, 1H), 8.12 (s, 1H), 8.08 (d, J=5.6 Hz, 1H), 8.02 (d, J=5.6 Hz, 1H), 7.94 (s, 1H), 7.59 (d, J=1.8 Hz, 1H), 6.51 (d, J=1.8 Hz, 1H), 3.50 (s, 3H), 2.92 (d, J=4.8 Hz, 3H), 2.20 (s, 3H), 1.64 (s, 3H).

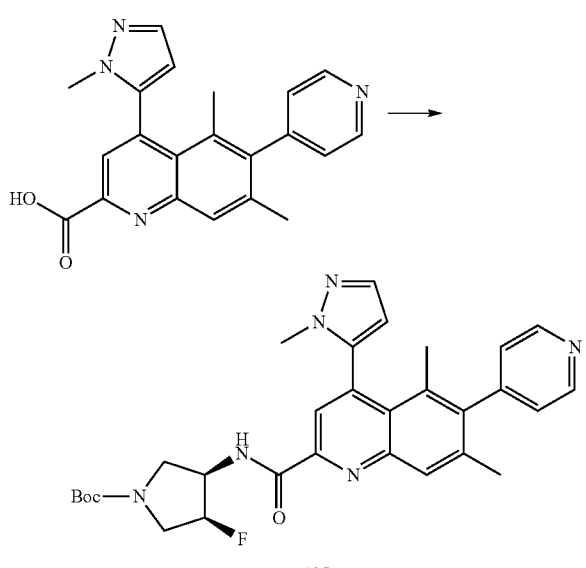

105-A

To a mixture of 5,7-dimethyl-4-(2-methylpyrazol-3-yl)-6-(4-pyridyl)quinoline-2-carboxylic acid (300 mg, 837 µmol), HATU (413 mg, 1.09 mmol) and diisopropylethylamine (649 mg, 5.02 mmol) in DMF (10 mL) was added tert-butyl (3R,4S and 3S,4R)-3-amino-4-fluoro-pyrrolidine-1-carboxylate (205 mg, 1.00 mmol). The reaction mixture was stirred at 25° C. for 1 hr. On completion, the reaction mixture was concentrated in vacuo. The residue was purified by silica gel chromatography (dichloromethane:methanol=50:1) to give 105-A (350 mg, 50% yield) as light yellow solid. LCMS (M+1)$^+$=545.2. LCMS (M−56)+=489.1.

105

To a solution of tert-butyl (3R,4S and 3S,4R)-3-[[5,7-dimethyl-4-(2-methylpyrazol-3-yl)-6-(4-pyridyl) quinoline-2-carbonyl]amino]-4-fluoro-pyrrolidine-1-carboxylate (300 mg, 550 mol) in dichloromethane (5 mL) was added HCl/dioxane (4 M, 5 mL) and the reaction mixture was stirred at 25° C. for 10 min. On completion, the reaction mixture was concentrated in vacuo. The residue was diluted with dichloromethane (20 mL) and basified with saturated sodium bicarbonate solution to pH=8. The aqueous phase was extracted with dichloromethane (3×20 mL), the organic layer was concentrated in vacuo to give the title compound (200 mg, 47% yield) as light yellow solid. LCMS (M+1)$^+$=445.2. 50 mg crude product was purified by prep-HPLC (column: Phenomenex Gemini 150*25 mm*10 µm; mobile phase: [water (0.05% ammonia hydroxide v/v)-ACN]) to give 105 (7.5 mg). LCMS (M+1)$^+$=445.2. $^1$H NMR (400 MHz, DMSO-d$_6$) δ=8.72-8.69 (m, 2H), 8.67 (d, J=7.6 Hz, 1H), 8.16 (s, 1H), 7.94 (s, 1H), 7.58 (d, J=2.0 Hz, 1H), 7.33 (d, J=4.4 Hz, 1H), 7.29 (d, J=4.4 Hz, 1H), 6.51 (s, 1H), 5.30-5.09 (m, 1H), 4.47-4.32 (m, 1H), 3.50 (s, 3H), 3.29-3.15 (m, 2H), 3.08-2.95 (m, 1H), 2.84-2.78 (m, 1H), 2.17 (s, 3H), 1.63 (s, 3H).

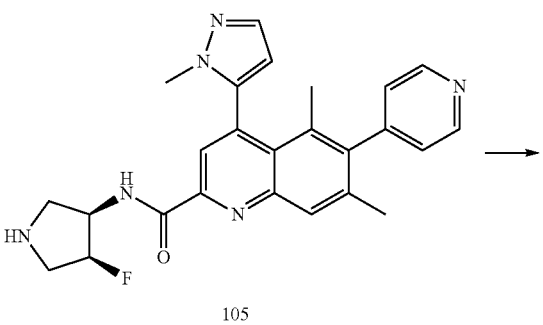

105

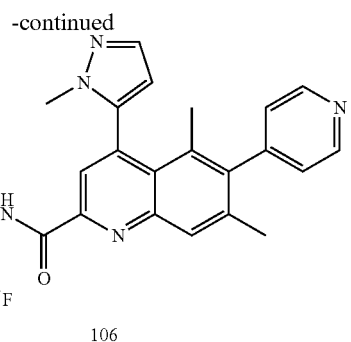

106

To a mixture of N-[(3R,4S and 3S,4R)-4-fluoropyrrolidin-3-yl]-5,7-dimethyl-4-(2-methylpyrazol-3-yl)-6-(4-pyridyl)quinoline-2-carboxamide (150 mg, 337 μmol) in formic acid (5 mL) was added formaldehyde (5 mL, 40% aqueous solution). The reaction mixture was stirred at 90° C. for 0.5 hr. On completion, the reaction mixture was concentrated in vacuo and dissolved in 10 mL MeOH. The mixture was basified with ammonia hydroxide to pH=8 and concentrated in vacuo. The residue was purified by prep-HPLC (column: Phenomenex Gemini 150*25 mm*10 μm; mobile phase: [water (0.05% ammonia hydroxide v/v)-ACN]) to give 106 (15.0 mg, 10% yield) as white solid. LCMS (M+1)$^+$=459.2. 1H NMR (400 MHz, DMSO-d6) δ=8.72 (d, J=7.6 Hz, 1H), 8.70 (d, J=5.6 Hz, 2H), 8.16 (s, 1H), 7.93 (s, 1H), 7.58 (d, J=1.6 Hz, 1H), 7.34 (d, J=4.8 Hz, 1H), 7.28 (d, J=4.8 Hz, 1H), 6.51 (s, 1H), 5.38-5.14 (m, 1H), 4.68-4.54 (m, 1H), 3.49 (s, 3H), 3.08-2.92 (m, 1H), 2.86-2.73 (m, 3H), 2.34 (s, 3H), 2.17 (s, 3H), 1.63 (s, 3H).

Preparation of Compound 107

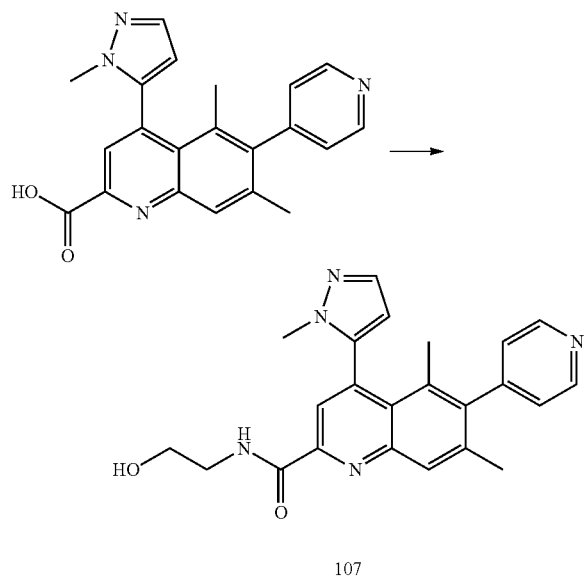

107

To a solution of 5,7-dimethyl-4-(2-methylpyrazol-3-yl)-6-(4-pyridyl)quinoline-2-carboxylic acid (80 mg, 223 μmol) in DMF (5 mL) was added 2-aminoethanol (21.8 mg, 357 μmol), HATU (169 mg, 446 μmol) and DIPEA (115 mg, 892 μmol) at 20° C. The reaction mixture was stirred at 20° C. for 18 hours. On completion, the reaction mixture was diluted with water (6 mL), extracted with DCM (3×20 mL). The combined organic layer was washed with brine (20 mL), dried over anhydrous sodium sulfate, filtered and concentrated in vacuo. The residue was dissolved in DCM (20 mL), and added thiourea (resin) (1.00 g). The mixture was stirred at 25° C. for 16 hours. Then the reaction mixture was filtrated and the filtrate was concentrated in vacuo to give a crude product. The crude product was purified by prep-HPLC (column: Phenomenex Gemini 150*25 mm*10 μm; mobile phase: [water (0.05% ammonia hydroxide v/v)-ACN]; B %: 27%-55%, 10 min) to give 107 (7.85 mg, 8% yield) as a white solid. LCMS (M+1)$^+$: 402.1. 1H NMR (400 MHz, DMSO-d6) δ=8.91 (t, J=5.6 Hz, 1H), 8.74-8.67 (m, 2H), 8.11 (s, 1H), 7.92 (s, 1H), 7.57 (d, J=2.0 Hz, 1H), 7.37-7.24 (m, 2H), 6.50 (d, J=2.0 Hz, 1H), 4.89 (t, J=5.6 Hz, 1H), 3.61 (q, J=5.6 Hz, 2H), 3.55-3.43 (m, 5H), 2.18 (s, 3H), 1.63 (s, 3H).

Example 22: Antitubercular Activity

The antitubercular activity was evaluated against *M. tuberculosis* strains. The Minimum Inhibitory Concentration (MIC$_{90}$) of the compounds is reported in Tables 1-6.

The measurement of the Minimum Inhibitory Concentration (MIC) against *M. tuberculosis* strains for each tested compound was performed in 96-well flat-bottom, polystyrene microtiter plates in a final volume of 100 □ polystyrene microtiter plates in a final volume of 100 of 100 against *M. tuberculosis* tions were added to Middlebrook 7H9 medium (Difco) and isoniazid (INH) (Sigma Aldrich) was used as a positive control with 2-fold dilutions of INH starting at 1600 □g/mL. The inoculum was standardized to approximately 1×107 cfu/ml and diluted 1 in 100 in Middlebrook 7H9 broth (Difco). This inoculum (1000 □L) was added to the entire plate but G-12 and H-12 wells were used as blank controls. All plates were placed in a sealed box to prevent drying out of the peripheral wells and incubated at 37° C. without shaking for six days. A Resazurin solution was prepared by dissolving one tablet of Resazurin (Resazurin Tablets for Milk Testing; Ref 330884Y' VWR International Ltd) in 30 mL of sterile PBS (phosphate buffered saline). Of this solution, 25 □L were added to each well. Fluorescence was measured (Spectramax M5 Molecular Devices, Excitation 530 nm, Emission 590 nm) after 48 hours to determine the MIC value.

TABLE 1

C2 SAR with chlorophenyl

| R$^4$ | Compound | MIC90/μM |
|---|---|---|
| H | 1 | 5 |
| ![](OEt ester) | 2 | 10 |
| | 3 | 3.75 |

TABLE 1-continued
C2 SAR with chlorophenyl
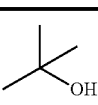
| R⁴ | Compound | MIC90/μM |
|---|---|---|
|  | 4 | >40 |
|  | 5 | 10 |
|  | 6 | 5 |
| NH₂ | 7 | 10 |
| NHMe | 8 | 6 |
|  | 9 | 3 |
|  | 10 | 20 |
| 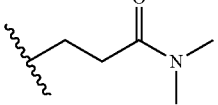 | 11 | 10 |
| 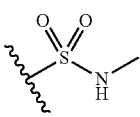 | 12 | 1.25 |
| 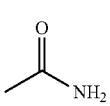 | 13 | 0.8 |
| 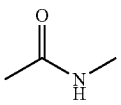 | 14 | 1.9 |
| 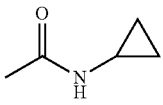 | 15 | 0.3 |
| 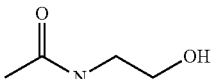 | 16 | 0.3 |
TABLE 1-continued
C2 SAR with chlorophenyl
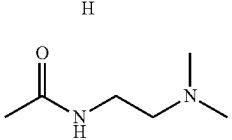
| R⁴ | Compound | MIC90/μM |
|---|---|---|
| 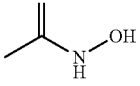 | 17 | 10 |
| 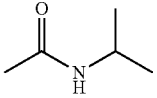 | 18 | 0.6 |
|  | 19 | 2.5 |
|  | 20 | 2.5 |
| 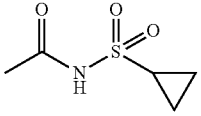 | 21 | 0.8 |
| 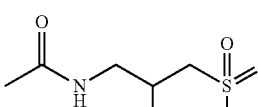 | 22 | 0.4 |
| 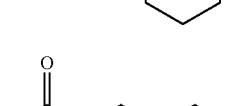 (racemic) | 23 | 1.25 |
| 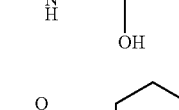 (racemic) | 24 | 0.6 |
| 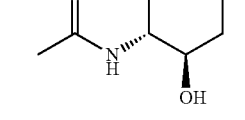 | 25 | 1.25 |

TABLE 1-continued
C2 SAR with chlorophenyl
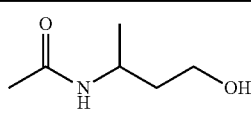
| R⁴ | Compound | MIC90/μM |
|---|---|---|
| 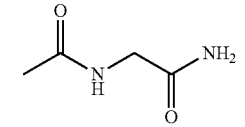 | 26 | 1.25 |
| 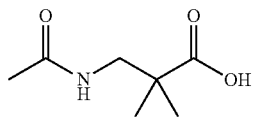 | 27 | 0.8 |
| 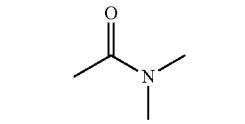 | 28 | 80 |
| 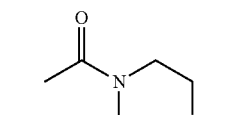 | 29 | 20 |
| 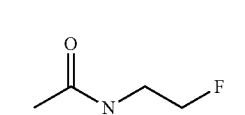 | 30 | 10 |
| 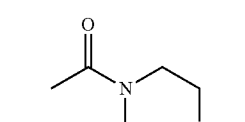 | 31 | 1.25 |
| 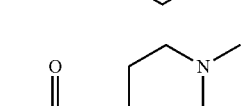 | 32 | 15 |
| 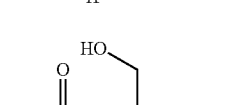 | 33 | 0.8 |
| 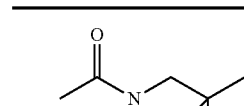 | 34 | 1.9 |
TABLE 1-continued
C2 SAR with chlorophenyl
| R⁴ | Compound | MIC90/μM |
|---|---|---|
|  | 35 | 1.6 |
TABLE 1A
C2 SAR with fluorophenyl
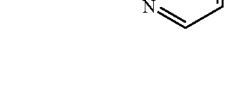
| R⁴ | Compound | MIC90/μM |
|---|---|---|
| H | 36 | 5 |
| 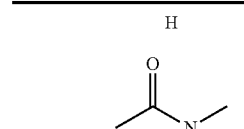 | 37 | 1.25 |
| 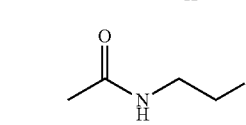 | 38 | 1.6 |
| 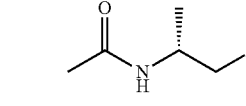 | 39 | 0.6 |
| 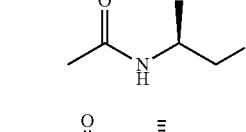 | 40 | 0.3 |
|  | 41 | 0.16 |
| 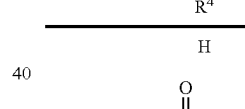 | 42 | 0.16 |

TABLE 1A-continued

C2 SAR with fluorophenyl

[Structure: 7-methyl-5-methyl-6-(pyridin-4-yl)-4-(2-fluorophenyl)quinoline with R⁴ at C2]

| R⁴ | Compound | MIC90/μM |
|---|---|---|
| CH₃C(O)NH-CH₂-CH(OH)-CH₂OH (S) | 43 | 0.8 |
| CH₃C(O)NH-CH₂-CH(OH)-CH₂OH (R) | 44 | 0.6 |
| CH₃C(O)NH-(1-methylpyrrolidin-3-yl) | 45 | 1.25 |
| CH₃C(O)NH-(1-methylpiperidin-4-yl) | 46 | 1.25 |

TABLE 2

C4 SAR

[Structure: quinoline with 7-methyl, 5-methyl, 6-(4-(morpholinomethyl)phenyl), 4-Cy²]

| Cy² | Compound | MIC90/μM |
|---|---|---|
| phenyl | 47 | 0.45 |
| 2-chlorophenyl | 48 | 0.3 |

TABLE 2-continued

C4 SAR

[Structure: quinoline with 7-methyl, 5-methyl, 6-(4-(morpholinomethyl)phenyl), 4-Cy²]

| Cy² | Compound | MIC90/μM |
|---|---|---|
| 3-chlorophenyl | 49 | 0.6 |
| 4-chlorophenyl | 50 | 80 |
| 2,3-dimethoxyphenyl | 51 | >40 |
| 2-cyanophenyl | 52 | 2.5 |
| 2-chloro-3-methoxyphenyl | 53 | 10 |
| 2-(diethylaminomethyl)phenyl | 54 | 2.5 |
| 2-(hydroxymethyl)phenyl | 55 | 2.5 |
| 2-carbamoylphenyl | 56 | 20 |

TABLE 2-continued

C4 SAR

[Structure: quinoline core with 7-methyl, 5-methyl, 6-(4-(morpholinomethyl)phenyl), 4-Cy² substituents]

| Cy² | Compound | MIC90/μM |
|---|---|---|
| 2-CO₂H-phenyl | 57 | 40 |
| 2,6-dimethylphenyl | 58 | 5 |
| 4-OMe-pyridin-3-yl | 59 | 2.5 |
| 2-OMe-pyridin-3-yl | 60 | 2.5 |
| 1,3-dimethyl-1H-pyrazol-5-yl | 61 | >40 |
| 2-CN-pyridin-3-yl | 62 | 7.5 |
| 1-methyl-1H-pyrazol-5-yl | 63 | 2.2 |
| pyrimidin-5-yl | 64 | 2.5 |
| 4-methylpyrimidin-5-yl | 65 | 5 |

TABLE 3

C4 SAR

[Structure: quinoline core with 7-methyl, 5-methyl, 6-(pyridin-4-yl), 2-(N-methylcarboxamide), 4-Cy₂ substituents]

| Cy² | Compound | MIC90/μM |
|---|---|---|
| 2-Cl-phenyl | 13 | 0.8 |
| 3-Cl-phenyl | 66 | 2.5 |
| 4-Cl-phenyl | 67 | 40 |
| pyrimidin-5-yl | 68 | 10 |
| 2-F-phenyl | 37 | 0.6 |

TABLE 3-continued

C4 SAR

[Structure: quinoline core with 7-methyl, 5-methyl, 6-(pyridin-4-yl), 2-(N-methylcarboxamide), and 4-Cy₂ substituents]

| Cy² | Compound | MIC90/μM |
|---|---|---|
| piperidin-1-yl | 69 | 5 |
| morpholin-4-yl | 70 | 20 |
| pyrrolidin-1-yl | 71 | >50 |

TABLE 4

C6 SAR

[Structure: quinoline core with 7-methyl, 5-methyl, 6-Cy¹, and 4-phenyl substituents]

| Cy¹ | Compound | MIC90/μM |
|---|---|---|
| 4-(morpholinomethyl)phenyl | 47 | 0.45 |
| pyridin-4-yl | 72 | 5 |
| pyrimidin-5-yl | 73 | 40 |

TABLE 4-continued

C6 SAR

| Cy¹ | Compound | MIC90/μM |
|---|---|---|
| oxazol-5-yl | 74 | 31 |
| 1-methyl-1H-pyrazol-3-yl | 75 | >125 |
| 1-methyl-1H-pyrazol-5-yl | 76 | 47 |
| 1-methyl-1H-pyrazol-4-yl | 77 | 47 |

[Structure: quinoline core with 7-methyl, 5-methyl, 6-Cy¹, 2-(N-methylcarboxamide), and 4-(2-fluorophenyl) substituents]

| Cy¹ | Compound | MIC90/μM |
|---|---|---|
| pyridin-4-yl | 37 | 1.25 |
| 4-(morpholinomethyl)phenyl | 78 | 0.6 |
| 2-(trifluoromethyl)pyridin-4-yl | 79 | 5 |
| furan-3-yl | 80 | 0.6 |

TABLE 4-continued
C6 SAR
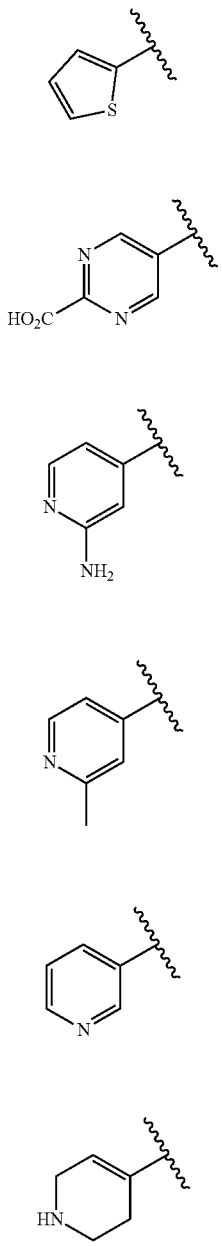
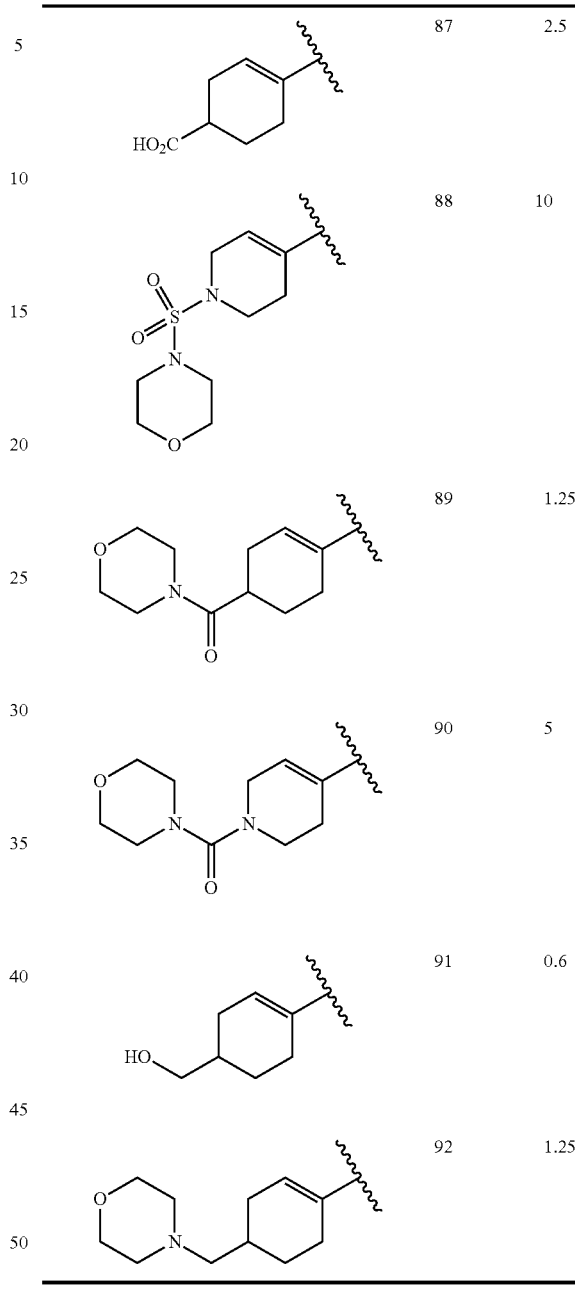
TABLE 5
| Compound | Compound | MIC90/μM |
|---|---|---|
| | 93 | 1.6 |

TABLE 5-continued

| Compound | Compound | MIC90/μM |
|---|---|---|
| (structure) | 94 | 5 |
| (structure) | 95 | 0.3 |
| (structure) | 96 | 0.3 |
| (structure) | 97 | <0.16 |
| (structure) | 98 | 0.6 |

TABLE 5-continued

| Compound | Compound | MIC90/μM |
|---|---|---|
| | 99 | 12.5 |
| | 100 | >50 |
| | 101 | >50 |
| | 102 | 3 |

TABLE 6

| Compound | Compound | MIC90/μM |
|---|---|---|
| | 103 | 0.8 |

TABLE 6-continued

| Compound | Compound | MIC90/μM |
|---|---|---|
| (structure) | 104 | 6 |
| (structure) | 105 | 3 |
| (structure) | 106 | 1.6 |
| (structure) | 107 | 1.6 |

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. A compound having a structure of Formula (I) or a pharmaceutically acceptable salt thereof:

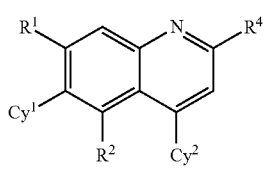

Formula (I)

wherein, independently for each occurrence,
$R^1$ is unsubstituted lower alkyl;
$R^2$ is unsubstituted lower alkyl;
$R^4$ is selected from —C(O)NR$^5$R$^6$ and —C(O)NHS(O$_2$)R$^7$;

R⁵ is hydrogen, substituted or unsubstituted alkyl, substituted or unsubstituted cycloalkyl, or substituted or unsubstituted heterocyclyl;

R⁶ is hydrogen, hydroxyl, substituted or unsubstituted alkyl or substituted or unsubstituted cycloalkyl; or R⁵ and R⁶ together with the nitrogen to which they are attached form a substituted or unsubstituted heterocyclyl;

R⁷ is substituted or unsubstituted alkyl, substituted or unsubstituted cycloalkyl, substituted or unsubstituted heterocyclyl, substituted or unsubstituted aryl or substituted or unsubstituted heteroaryl;

Cy¹ is selected from substituted or unsubstituted cycloalkyl, substituted or unsubstituted heterocyclyl, substituted or unsubstituted aryl, and substituted or unsubstituted heteroaryl; and Cy² is selected from substituted or unsubstituted cycloalkyl, substituted or unsubstituted heterocyclyl, substituted or unsubstituted aryl, and substituted or unsubstituted heteroaryl.

2. The compound of claim 1, wherein Cy¹ is selected from:

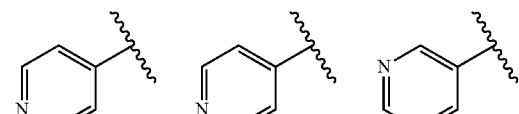
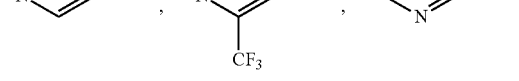
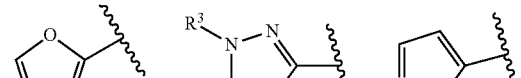
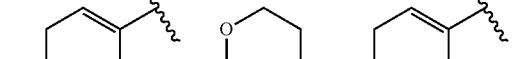
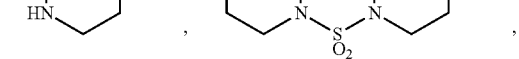
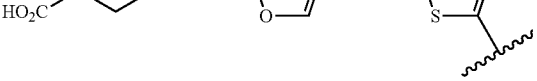
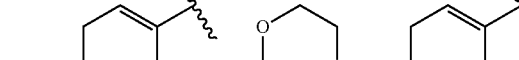
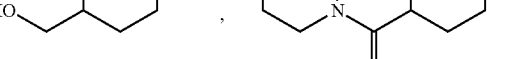

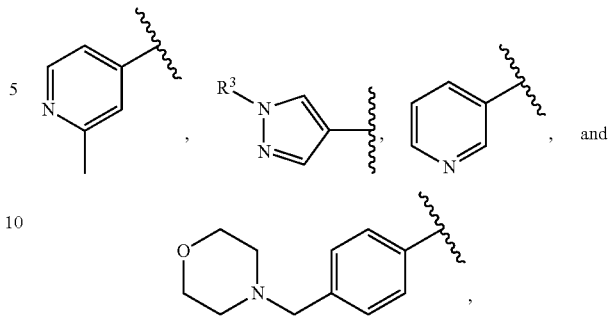

wherein R³ is H or methyl.

3. The compound of claim 1, wherein Cy¹ is selected from:

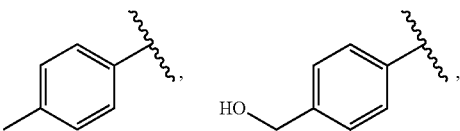
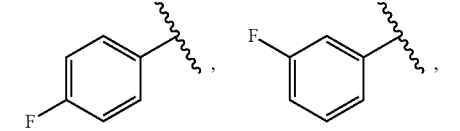
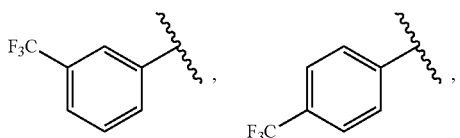
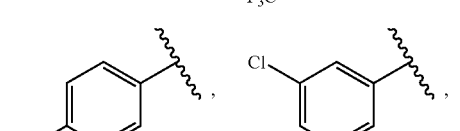
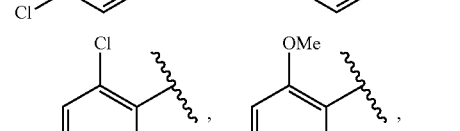
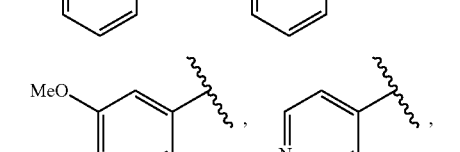
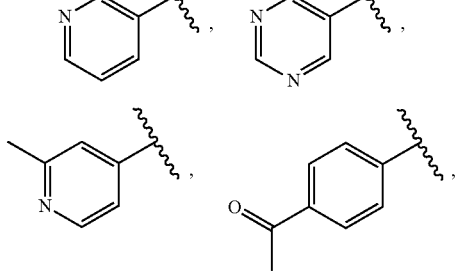

-continued

4. The compound of claim 1, wherein Cy¹ is selected from: substituted or unsubstituted phenyl, furyl, thienyl, pyridinyl, pyrimidinyl, naphthyl, oxazolyl, pyrazolyl, piperidinyl, heterocycloalkenyl, cycloalkenyl, and imidazolyl.

5. The compound of claim 1, wherein Cy² is selected from:

-continued

6. The compound of claim 1, wherein Cy² is selected from: substituted or unsubstituted phenyl, pyridinyl, pyrazolyl, pyrimidinyl, cycloalkenyl, piperidinyl, morpholino, heterocycloalkenyl, and pyrrolidinyl.

7. A compound of claim 1, wherein R⁴ is selected from:

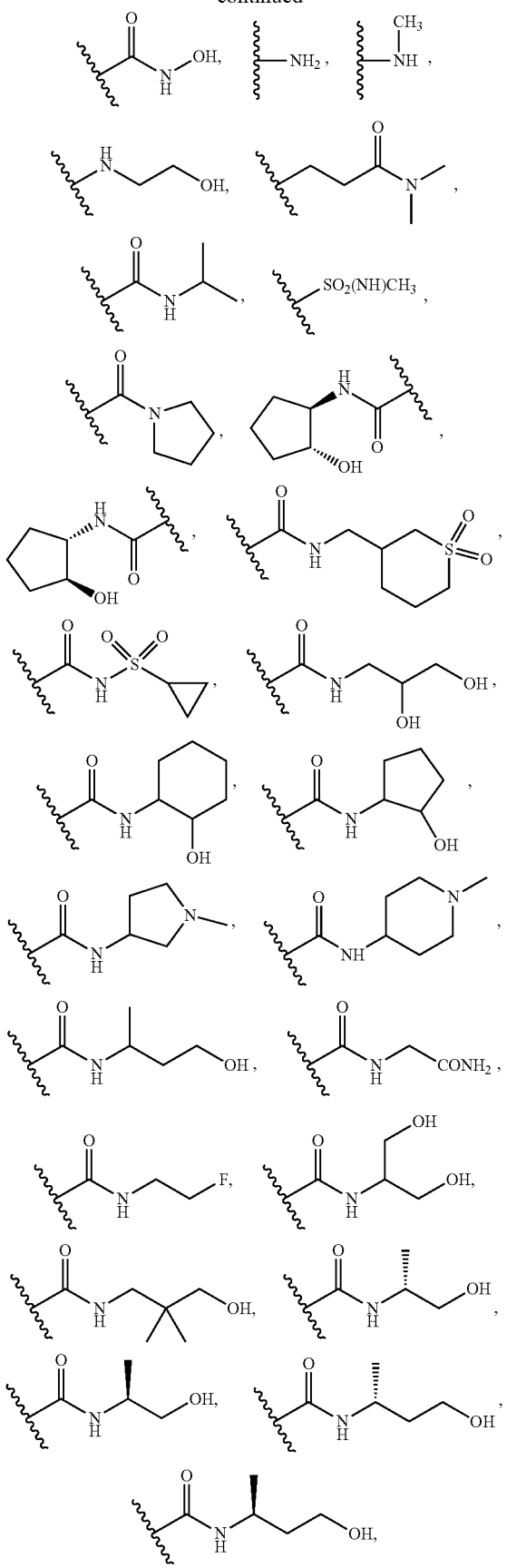

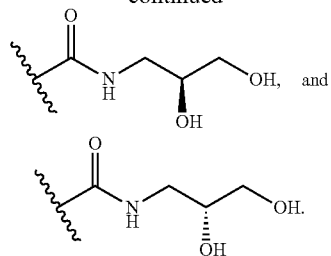

8. The compound of claim 1, wherein $Cy^1$ is

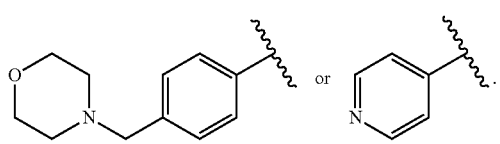 [SMILES: *c1ccc(CN2CCOCC2)cc1 ; *c1ccncc1]

9. The compound of claim 1, wherein $Cy^2$ is

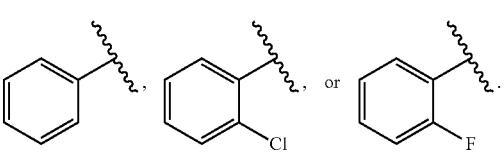

10. The compound of claim 1, wherein $R^4$ is

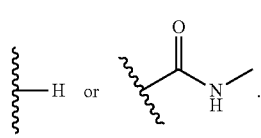

11. The compound of claim 1, wherein $R^4$ is not H.
12. The compound of claim 1, wherein $R^1$ and $R^2$ are methyl.
13. A pharmaceutical composition comprising a compound of claim 1.
14. A pharmaceutical composition according to claim 13, further comprising one or more pharmaceutically acceptable excipients.
15. A method of treating a mycobacterial infection in a subject, comprising administering to the subject a compound having a structure of Formula (I) or a pharmaceutically acceptable salt thereof:

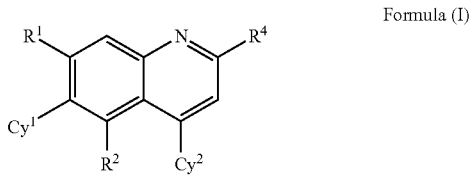

Formula (I)

wherein, independently for each occurrence,
$R^1$ is unsubstituted lower alkyl,
$R^2$ is unsubstituted lower alkyl,
$R^4$ is selected from hydrogen, substituted or unsubstituted acyl, substituted or unsubstituted alkyl, substituted or unsubstituted alkoxy, substituted or unsubstituted alkylamino, amino, substituted or unsubstituted dialkylamino, sulfonamido, —C(O)OR$^5$, —C(O)R$^7$, —C(O)NR$^5$R$^6$, —C(O)NHS(O$_2$)R$^7$ and —S(O$_2$)R$^7$;

R$^5$ is hydrogen, substituted or unsubstituted alkyl, substituted or unsubstituted cycloalkyl, or substituted or unsubstituted heterocyclyl;

R$^6$ is hydrogen, hydroxyl, substituted or unsubstituted alkyl or substituted or unsubstituted cycloalkyl; or R$^5$ and R$^6$ together with the nitrogen to which they are attached form a substituted or unsubstituted heterocyclyl;

R$^7$ is substituted or unsubstituted alkyl, substituted or unsubstituted cycloalkyl, substituted or unsubstituted heterocyclyl, substituted or unsubstituted aryl or substituted or unsubstituted heteroaryl;

Cy$^1$ is selected from substituted or unsubstituted cycloalkyl, substituted or unsubstituted heterocyclyl, substituted or unsubstituted aryl, and substituted or unsubstituted heteroaryl; and Cy$^2$ is selected from substituted or unsubstituted cycloalkyl, substituted or unsubstituted heterocyclyl, substituted or unsubstituted aryl, and substituted or unsubstituted heteroaryl.

16. The method of claim 15, wherein the subject is a mammal.

17. The method of claim 15, wherein the mycobacterial infection is caused by *Mycobacterium abscessus, Mycobacterium avium* complex, *Mycobacterium goodii, Mycobacterium leprae, Mycobacterium lepraemurium, Mycobacterium lepromatosis, Mycobacterium mucogenicum, Mycobacterium neoaurum, Mycobacterium triplex*, or *Mycobacterium tuberculosis* complex.

18. The method of claim 15, wherein the compound is administered orally, nasally, buccally, sublingually, intramuscularly, intravenously, transmucosally, rectally, topically, transdermally, subcutaneously, or by inhalation.

19. The method of claim 15, wherein R$^4$ is not H.

20. The method of claim 15, wherein R$^1$ and R$^2$ are both methyl.

* * * * *